US009149503B2

(12) United States Patent
Roden et al.

(10) Patent No.: US 9,149,503 B2
(45) Date of Patent: Oct. 6, 2015

(54) PAPILLOMAVIRUS-LIKE PARTICLES (VLP) AS BROAD SPECTRUM HUMAN PAPILLOMAVIRUS (HPV) VACCINES

(75) Inventors: Richard B. S. Roden, Baltimore, MD (US); Reinhard Kirnbauer, Vienna (AT); Christina Schellenbacher, Vienna (AT)

(73) Assignee: The Johns Hopkins University, Baltimore, MD (US)

( * ) Notice: Subject to any disclaimer, the term of this patent is extended or adjusted under 35 U.S.C. 154(b) by 329 days.

(21) Appl. No.: 13/263,563

(22) PCT Filed: Apr. 12, 2010

(86) PCT No.: PCT/US2010/030757
§ 371 (c)(1),
(2), (4) Date: Oct. 7, 2011

(87) PCT Pub. No.: WO2010/118424
PCT Pub. Date: Oct. 14, 2010

(65) Prior Publication Data
US 2012/0093821 A1     Apr. 19, 2012

Related U.S. Application Data

(60) Provisional application No. 61/168,445, filed on Apr. 10, 2009.

(51) Int. Cl.
*A61K 39/12* (2006.01)
*C12N 7/01* (2006.01)
*C07K 14/005* (2006.01)
*A61K 38/16* (2006.01)
*C12N 7/00* (2006.01)

(52) U.S. Cl.
CPC ............... *A61K 38/16* (2013.01); *A61K 39/12* (2013.01); *C07K 14/005* (2013.01); *C07K 2319/40* (2013.01); *C12N 7/00* (2013.01); *C12N 2710/20023* (2013.01); *C12N 2710/20034* (2013.01)

(58) Field of Classification Search
CPC ........... C12N 2710/20011; C12N 2710/20023; C12N 2710/20034; C12N 7/045
See application file for complete search history.

(56) References Cited

U.S. PATENT DOCUMENTS

| 2003/0207446 A1 | 11/2003 | Lowy et al. | |
|---|---|---|---|
| 2009/0047301 A1 | 2/2009 | Schiller et al. | |
| 2010/0183648 A1 | 7/2010 | Kanda et al. | |
| 2012/0087937 A1* | 4/2012 | Colau et al. | 424/186.1 |
| 2012/0171290 A1* | 7/2012 | Coursaget et al. | 424/489 |

FOREIGN PATENT DOCUMENTS

| KR | 10-0497289 B1 | 6/2005 | | |
|---|---|---|---|---|
| WO | WO-2007/018049 A1 | 2/2007 | | |
| WO | WO-2009/001867 A1 | 12/2008 | | |
| WO | WO 2012/177970 | * 12/2012 | ............ | A61K 39/00 |

OTHER PUBLICATIONS

Kondo et al (Journal of Medical Virology 80:841-846, 2008; published online Mar. 21, 2008).*
Kondo et al (Journal of Medical Virology 80:841-846, published online Mar. 21, 2008).*
Slupetzky et al (Vaccine 25:2001-2010, 2007).*
Gambhira R., et al. Protection of rabbits against challenge with rabbit papillomaviruses by immunization with the N termins of human papillomavirus type 16 minor capsid antigen L2, J. Virol., vol. 81(21), pp. 11585-11592 (Epub Aug. 22, 2007).
International Search Report (PCT/ISA/210), Mar. 29, 2011.
Written Opinion (PCT/ISA/237), Mar. 29, 2011.
Kirnbauer et al, "Efficient self-assembly of human papillomavirus type 16 L1 and L1-L2 into virus-like particles," J. Virol. 1993, 67(12):6929.
Rubio et al, "Potent anti-HPV immune responses induced by tandem repeats of the HPV16 L2 (20-38) peptide displayed on bacterial thioredoxin," Vaccine 27 (2009) pp. 1949-1955.
Tumban et al, "VLPs Displaying a Single L2 Epitope Induce Broadly Cross-Neutralizing Antibodies against Human Papillomavirus," PLOS ONE, Nov. 2012, vol. 7, Iss. 11, pp. 1-11.
Notification of the First Office Action issued May 10, 2013 in Chinese Patent Application No. 201080025772.0.
Varsani et al., "Chimeric Human Papillomavirus Type 16 (HPV-16) L1 Particles Presenting the Common Neutralizing Epitope for the L2 Minor Capsid Protein of HPV-6 and HPV-16," Journal of Virology, vol. 77, No. 15, pp. 8386-8393.
Extended European Search Report issued Dec. 11, 2012 in European Patent Application No. 10762572.5.
Office Action issued Sep. 9, 2014 in European Patent Application No. 10762572.5.
Office Action issued Feb. 17, 2014 in European Patent Application No. 10762572.5.
Kondo et al., "Neutralization of HPV 16, 18, 31, and 58 pseudovirions with antisera induced by immunizing rabbits with synthetic peptids representing segments of the HPV 16 minor capsid protein L2 surface region," Virology Academic Press, Orlando, Florida, US, vol. 358, No. 2, pp. 266-272.

(Continued)

*Primary Examiner* — Mary E Mosher
(74) *Attorney, Agent, or Firm* — Venable LLP; Stefan J. Kirchanski; Miguel A. Lopez

(57) ABSTRACT

This invention relates, e.g., to a virus-like particle (VLP) composition assembled from a chimeric polypeptide comprising a papilloma virus (e.g., human papillomavirus, or HPV) L1 major capsid protein, into which is inserted a surface-displayed peptide comprising a neutralizing epitope of a papillomavirus L2 protein. Vaccine compositions comprising the VLP are described, as well as methods for inducing an immune response (e.g., vaccinating) a subject against papilloma virus, using the VLP, and kits comprising the VLP, for carrying out a method of the invention.

43 Claims, 6 Drawing Sheets

(56) References Cited

OTHER PUBLICATIONS

Bishop et al., "Crystal structures of four types of human papillomavirus L1 capsid proteins: Understating the specificity of neutralizing monoclonal antibodies," Journal of Biological Chemistry, American Society for Biochemistry and Moleculart Biology, US, vol. 282, No. 43, Oct. 26, 2007, pp. 31803-31811.

Roth et al., "Characterization of neutralizing epitopes within the major capsid protein of human papillomavirus type 33," Virology Joural, Biomed Central, London, United Kingdom, vol. 3, No. 1, Oct. 2, 2006, p. 83.

Chen et al., "Structure of small virus-like particles assembled from the L1 protein of human papillomavirus 16," Molecular Cell, vol. 5, Mar. 2000, Cell Press, pp. 557-567.

* cited by examiner

```
SEQUENCE LISTING

<160> NUMBER OF SEQ ID NOS: 98

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Gln, His or Glu
<220> FEATURE:
<221> NAME/KEY: MOD_RES
<222> LOCATION: (2)..(2)
<223> OTHER INFORMATION: Leu or Ile
<220> FEATURE:
<221> NAME/KEY: MOD_RES
<222> LOCATION: (4)..(4)
<223> OTHER INFORMATION: Lys, Pro, Arg, Gln or Ser
<220> FEATURE:
<221> NAME/KEY: MOD_RES
<222> LOCATION: (5)..(5)
<223> OTHER INFORMATION: Thr, Ser, Ala or Gly
<220> FEATURE:
<221> NAME/KEY: MOD_RES
<222> LOCATION: (8)..(8)
<223> OTHER INFORMATION: Gln, Ile, Val, Leu or Ala
<220> FEATURE:
<221> NAME/KEY: MOD_RES
<222> LOCATION: (9)..(9)
<223> OTHER INFORMATION: Ala, Ser or Thr
<220> FEATURE:
<221> NAME/KEY: MOD_RES
<222> LOCATION: (10)..(10)
<223> OTHER INFORMATION: Gly or Asn
```

```
<220> FEATURE:
<221> NAME/KEY: MOD_RES
<222> LOCATION: (11)..(11)
<223> OTHER INFORMATION: Thr or Asn
<220> FEATURE:
<221> NAME/KEY: MOD_RES
<222> LOCATION: (16)..(16)
<223> OTHER INFORMATION: Ile or Val
<220> FEATURE:
<221> NAME/KEY: MOD_RES
<222> LOCATION: (17)..(17)
<223> OTHER INFORMATION: Ile, Val or Gln
<220> FEATURE:
<221> NAME/KEY: MOD_RES
<222> LOCATION: (18)..(18)
<223> OTHER INFORMATION: Pro, Asn or Asp
<220> FEATURE:
<221> NAME/KEY: MOD_RES
<222> LOCATION: (19)..(19)
<223> OTHER INFORMATION: Lys or Arg
<220> FEATURE:
<221> NAME/KEY: MOD_RES
<222> LOCATION: (20)..(20)
<223> OTHER INFORMATION: Val, Ile or Leu

<400> SEQUENCE: 1

Xaa Xaa Tyr Xaa Xaa Cys Lys Xaa Xaa Xaa Xaa Cys Pro Pro Asp Xaa
1               5                   10                  15

Xaa Xaa Xaa Xaa
        20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Gln, His or Glu
<220> FEATURE:
<221> NAME/KEY: MOD_RES
<222> LOCATION: (2)..(2)
<223> OTHER INFORMATION: Leu or Ile
<220> FEATURE:
<221> NAME/KEY: MOD_RES
<222> LOCATION: (4)..(4)
<223> OTHER INFORMATION: Lys, Pro, Arg, Gln or Ser
<220> FEATURE:
<221> NAME/KEY: MOD_RES
<222> LOCATION: (5)..(5)
<223> OTHER INFORMATION: Thr, Ser, Ala or Gly
<220> FEATURE:
<221> NAME/KEY: MOD_RES
<222> LOCATION: (8)..(8)
<223> OTHER INFORMATION: Gln, Ile, Val, Leu or Ala
<220> FEATURE:
<221> NAME/KEY: MOD_RES
<222> LOCATION: (9)..(9)
<223> OTHER INFORMATION: Ala, Ser or Thr
<220> FEATURE:
<221> NAME/KEY: MOD_RES
<222> LOCATION: (10)..(10)
<223> OTHER INFORMATION: Gly or Asn
<220> FEATURE:
<221> NAME/KEY: MOD_RES
<222> LOCATION: (11)..(11)
<223> OTHER INFORMATION: Thr or Asn
<220> FEATURE:
<221> NAME/KEY: MOD_RES
<222> LOCATION: (16)..(16)
<223> OTHER INFORMATION: Ile or Val
<220> FEATURE:
<221> NAME/KEY: MOD_RES
```

```
<222> LOCATION: (17)..(17)
<223> OTHER INFORMATION: Ile, Val or Gln
<220> FEATURE:
<221> NAME/KEY: MOD_RES
<222> LOCATION: (18)..(18)
<223> OTHER INFORMATION: Pro, Asn or Asp
<220> FEATURE:
<221> NAME/KEY: MOD_RES
<222> LOCATION: (19)..(19)
<223> OTHER INFORMATION: Lys or Arg
<220> FEATURE:
<221> NAME/KEY: MOD_RES
<222> LOCATION: (20)..(20)
<223> OTHER INFORMATION: Val, Ile or Leu

<400> SEQUENCE: 2

Xaa Xaa Tyr Xaa Xaa Cys Lys Xaa Xaa Xaa Xaa Cys Pro Pro Asp Xaa
1               5                   10                  15

Xaa Xaa Xaa Xaa
            20

<210> SEQ ID NO 3
<211> LENGTH: 20
<212> TYPE: PRT
<213> ORGANISM: Human papillomavirus

<400> SEQUENCE: 3

Asp Ile Tyr Pro Ser Cys Lys Ile Ser Asn Thr Cys Pro Pro Asp Ile
1               5                   10                  15

Gln Asn Lys Ile
            20

<210> SEQ ID NO 4
<211> LENGTH: 20
<212> TYPE: PRT
<213> ORGANISM: Human papillomavirus

<400> SEQUENCE: 4

Asp Leu Tyr Arg Thr Cys Lys Gln Ala Gly Thr Cys Pro Pro Asp Ile
1               5                   10                  15

Ile Pro Arg Val
            20

<210> SEQ ID NO 5
<211> LENGTH: 20
<212> TYPE: PRT
<213> ORGANISM: Human papillomavirus

<400> SEQUENCE: 5

His Ile Tyr Gln Thr Cys Lys Gln Ala Gly Thr Cys Pro Pro Asp Val
1               5                   10                  15

Ile Asn Lys Val
            20

<210> SEQ ID NO 6
<211> LENGTH: 20
<212> TYPE: PRT
<213> ORGANISM: Human papillomavirus

<400> SEQUENCE: 6

His Ile Tyr Gln Thr Cys Lys Gln Ala Gly Thr Cys Pro Pro Asp Val
1               5                   10                  15

Ile Asn Lys Val
            20
```

<210> SEQ ID NO 7
<211> LENGTH: 20
<212> TYPE: PRT
<213> ORGANISM: Human papillomavirus

<400> SEQUENCE: 7

Gln Leu Tyr Gln Thr Cys Lys Leu Thr Gly Thr Cys Pro Pro Asp Val
1               5                   10                  15

Ile Pro Lys Val
            20

<210> SEQ ID NO 8
<211> LENGTH: 20
<212> TYPE: PRT
<213> ORGANISM: Human papillomavirus

<400> SEQUENCE: 8

Gln Leu Tyr Gln Thr Cys Lys Ala Thr Gly Thr Cys Pro Pro Asp Val
1               5                   10                  15

Ile Pro Lys Val
            20

<210> SEQ ID NO 9
<211> LENGTH: 20
<212> TYPE: PRT
<213> ORGANISM: Human papillomavirus

<400> SEQUENCE: 9

Gln Leu Tyr Lys Thr Cys Lys Gln Ala Gly Thr Cys Pro Pro Asp Ile
1               5                   10                  15

Ile Pro Lys Val
            20

<210> SEQ ID NO 10
<211> LENGTH: 20
<212> TYPE: PRT
<213> ORGANISM: Human papillomavirus

<400> SEQUENCE: 10

Asp Leu Tyr Lys Thr Cys Lys Gln Ser Gly Thr Cys Pro Pro Asp Val
1               5                   10                  15

Val Pro Lys Val
            20

<210> SEQ ID NO 11
<211> LENGTH: 20
<212> TYPE: PRT
<213> ORGANISM: Human papillomavirus

<400> SEQUENCE: 11

Asp Leu Tyr Arg Thr Cys Lys Gln Ser Gly Thr Cys Pro Pro Asp Val
1               5                   10                  15

Ile Asn Lys Val
            20

<210> SEQ ID NO 12
<211> LENGTH: 20
<212> TYPE: PRT
<213> ORGANISM: Human papillomavirus

<400> SEQUENCE: 12

Gln Leu Tyr Gln Thr Cys Lys Ala Ala Gly Thr Cys Pro Ser Asp Val

```
1               5                   10                  15

Ile Pro Lys Ile
            20

<210> SEQ ID NO 13
<211> LENGTH: 20
<212> TYPE: PRT
<213> ORGANISM: Human papillomavirus

<400> SEQUENCE: 13

Gln Leu Tyr Gln Thr Cys Lys Ala Thr Gly Thr Cys Pro Pro Asp Val
1               5                   10                  15

Ile Pro Lys Val
            20

<210> SEQ ID NO 14
<211> LENGTH: 20
<212> TYPE: PRT
<213> ORGANISM: Human papillomavirus

<400> SEQUENCE: 14

Gln Leu Tyr Gln Thr Cys Lys Ala Ser Gly Thr Cys Pro Pro Asp Val
1               5                   10                  15

Ile Pro Lys Val
            20

<210> SEQ ID NO 15
<211> LENGTH: 20
<212> TYPE: PRT
<213> ORGANISM: Human papillomavirus

<400> SEQUENCE: 15

Gln Leu Tyr Gln Thr Cys Lys Ala Ser Gly Thr Cys Pro Pro Asp Val
1               5                   10                  15

Ile Pro Lys Val
            20

<210> SEQ ID NO 16
<211> LENGTH: 20
<212> TYPE: PRT
<213> ORGANISM: Human papillomavirus

<400> SEQUENCE: 16

Gln Leu Tyr Arg Thr Cys Lys Ala Ala Gly Thr Cys Pro Pro Asp Val
1               5                   10                  15

Ile Pro Lys Val
            20

<210> SEQ ID NO 17
<211> LENGTH: 20
<212> TYPE: PRT
<213> ORGANISM: Human papillomavirus

<400> SEQUENCE: 17

Asp Leu Tyr Lys Thr Cys Lys Gln Ala Gly Thr Cys Pro Ser Asp Val
1               5                   10                  15

Ile Asn Lys Val
            20

<210> SEQ ID NO 18
<211> LENGTH: 20
<212> TYPE: PRT
```

<210> SEQ ID NO 18
<211> LENGTH: 20
<212> TYPE: PRT
<213> ORGANISM: Human papillomavirus

<400> SEQUENCE: 18

Gln Leu Tyr Lys Thr Cys Lys Leu Ser Gly Thr Cys Pro Glu Asp Val
1               5                   10                  15

Val Asn Lys Ile
            20

<210> SEQ ID NO 19
<211> LENGTH: 20
<212> TYPE: PRT
<213> ORGANISM: Human papillomavirus

<400> SEQUENCE: 19

Asp Leu Tyr Arg Thr Cys Lys Gln Ser Gly Thr Cys Pro Pro Asp Val
1               5                   10                  15

Val Asp Lys Val
            20

<210> SEQ ID NO 20
<211> LENGTH: 20
<212> TYPE: PRT
<213> ORGANISM: Human papillomavirus

<400> SEQUENCE: 20

Gln Leu Tyr Ser Thr Cys Lys Ala Ala Gly Thr Cys Pro Pro Asp Val
1               5                   10                  15

Val Asn Lys Val
            20

<210> SEQ ID NO 21
<211> LENGTH: 20
<212> TYPE: PRT
<213> ORGANISM: Cottontail rabbit papillomavirus

<400> SEQUENCE: 21

Asp Ile Tyr Pro Thr Cys Lys Ile Ala Gly Asn Cys Pro Ala Asp Ile
1               5                   10                  15

Gln Asn Lys Phe
            20

<210> SEQ ID NO 22
<211> LENGTH: 20
<212> TYPE: PRT
<213> ORGANISM: Bovine papillomavirus

<400> SEQUENCE: 22

Asp Leu Tyr Arg Thr Cys Lys Gln Ala Gly Thr Cys Pro Pro Asp Val
1               5                   10                  15

Ile Pro Lys Val
            20

<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (1)..(1)
<223> OTHER INFORMATION: Asp, His or Gln
<220> FEATURE:

```
<221> NAME/KEY: MOD_RES
<222> LOCATION: (4)..(4)
<223> OTHER INFORMATION: Pro, Arg, Gln, Lys, or Ser
<220> FEATURE:
<221> NAME/KEY: MOD_RES
<222> LOCATION: (8)..(8)
<223> OTHER INFORMATION: Ile, Gln, Leu or Ala
<220> FEATURE:
<221> NAME/KEY: MOD_RES
<222> LOCATION: (9)..(9)
<223> OTHER INFORMATION: Ser, Ala or Thr

<400> SEQUENCE: 23

Xaa Leu Tyr Xaa Thr Cys Lys Xaa Xaa Gly Thr Cys Pro Pro Asp Val
1               5                   10                  15

Ile Pro Lys Val
            20

<210> SEQ ID NO 24
<211> LENGTH: 20
<212> TYPE: PRT
<213> ORGANISM: Human papillomavirus

<400> SEQUENCE: 24

Gln Leu Tyr Lys Thr Cys Lys Gln Ala Gly Thr Cys Pro Pro Asp Val
1               5                   10                  15

Ile Pro Lys Val
            20

<210> SEQ ID NO 25
<211> LENGTH: 20
<212> TYPE: PRT
<213> ORGANISM: Human papillomavirus

<400> SEQUENCE: 25

Gln Leu Tyr Lys Thr Cys Lys Gln Ser Gly Thr Cys Pro Pro Asp Ile
1               5                   10                  15

Ile Pro Lys Val
            20

<210> SEQ ID NO 26
<211> LENGTH: 20
<212> TYPE: PRT
<213> ORGANISM: Ursus maritimus

<400> SEQUENCE: 26

Gln Leu Tyr Lys Thr Cys Lys Gln Ala Gly Thr Cys Pro Pro Asp Val
1               5                   10                  15

Ile Pro Lys Ile
            20

<210> SEQ ID NO 27
<211> LENGTH: 20
<212> TYPE: PRT
<213> ORGANISM: Human papillomavirus

<400> SEQUENCE: 27

Asp Leu Tyr Arg Thr Cys Lys Gln Ala Gly Thr Cys Pro Pro Asp Val
1               5                   10                  15

Ile Pro Lys Val
            20

<210> SEQ ID NO 28
<211> LENGTH: 20
```

```
<212> TYPE: PRT
<213> ORGANISM: Human papillomavirus

<400> SEQUENCE: 28

Asp Leu Tyr Arg Thr Cys Lys Gln Ala Gly Thr Cys Pro Pro Asp Ile
1               5                   10                  15

Ile Pro Arg Val
            20

<210> SEQ ID NO 29
<211> LENGTH: 20
<212> TYPE: PRT
<213> ORGANISM: Human papillomavirus

<400> SEQUENCE: 29

Asp Leu Tyr Arg Thr Cys Lys Gln Ala Gly Thr Cys Pro Pro Asp Ile
1               5                   10                  15

Ile Pro Arg Leu
            20

<210> SEQ ID NO 30
<211> LENGTH: 20
<212> TYPE: PRT
<213> ORGANISM: Human papillomavirus

<400> SEQUENCE: 30

Asp Leu Tyr Arg Thr Cys Lys Gln Ala Gly Thr Cys Pro Pro Asp Ile
1               5                   10                  15

Ile Pro Arg Val
            20

<210> SEQ ID NO 31
<211> LENGTH: 20
<212> TYPE: PRT
<213> ORGANISM: Human papillomavirus

<400> SEQUENCE: 31

Glu Leu Tyr Lys Thr Cys Lys Ala Ala Gly Thr Cys Pro Pro Asp Val
1               5                   10                  15

Ile Pro Lys Val
            20

<210> SEQ ID NO 32
<211> LENGTH: 20
<212> TYPE: PRT
<213> ORGANISM: Human papillomavirus

<400> SEQUENCE: 32

Gln Leu Tyr Gln Thr Cys Lys Ala Ala Gly Thr Cys Pro Pro Asp Val
1               5                   10                  15

Ile Pro Lys Val
            20

<210> SEQ ID NO 33
<211> LENGTH: 20
<212> TYPE: PRT
<213> ORGANISM: Human papillomavirus

<400> SEQUENCE: 33

Gln Leu Tyr Arg Thr Cys Lys Ala Ala Gly Thr Cys Pro Pro Asp Val
1               5                   10                  15

Ile Pro Lys Val
```

<210> SEQ ID NO 34
<211> LENGTH: 20
<212> TYPE: PRT
<213> ORGANISM: Human papillomavirus

<400> SEQUENCE: 34

Gln Leu Tyr Arg Thr Cys Lys Ala Ala Gly Thr Cys Pro Pro Asp Val
1               5                   10                  15

Ile Pro Lys Val
            20

<210> SEQ ID NO 35
<211> LENGTH: 20
<212> TYPE: PRT
<213> ORGANISM: Human papillomavirus

<400> SEQUENCE: 35

Glu Leu Tyr Lys Thr Cys Lys Val Ala Gly Thr Cys Pro Pro Asp Val
1               5                   10                  15

Ile Pro Lys Val
            20

<210> SEQ ID NO 36
<211> LENGTH: 20
<212> TYPE: PRT
<213> ORGANISM: Human papillomavirus

<400> SEQUENCE: 36

Gln Leu Tyr Ser Thr Cys Lys Ala Ala Gly Thr Cys Pro Pro Asp Val
1               5                   10                  15

Ile Pro Lys Val
            20

<210> SEQ ID NO 37
<211> LENGTH: 20
<212> TYPE: PRT
<213> ORGANISM: Human papillomavirus

<400> SEQUENCE: 37

Gln Leu Tyr Gln Thr Cys Lys Ala Ala Gly Thr Cys Pro Ser Asp Ile
1               5                   10                  15

Ile Pro Lys Val
            20

<210> SEQ ID NO 38
<211> LENGTH: 20
<212> TYPE: PRT
<213> ORGANISM: Human papillomavirus

<400> SEQUENCE: 38

Gln Leu Tyr Gln Thr Cys Lys Ala Ala Gly Thr Cys Pro Ser Asp Ile
1               5                   10                  15

Ile Pro Lys Val
            20

<210> SEQ ID NO 39
<211> LENGTH: 20
<212> TYPE: PRT
<213> ORGANISM: Human papillomavirus

<400> SEQUENCE: 39

Gln Leu Tyr Gln Thr Cys Lys Ala Ala Gly Thr Cys Pro Pro Asp Val
1               5                   10                  15

Val Asn Lys Val
            20

<210> SEQ ID NO 40
<211> LENGTH: 20
<212> TYPE: PRT
<213> ORGANISM: Human papillomavirus

<400> SEQUENCE: 40

Gln Leu Tyr Arg Thr Cys Lys Ala Ser Gly Thr Cys Pro Pro Asp Val
1               5                   10                  15

Ile Pro Lys Val
            20

<210> SEQ ID NO 41
<211> LENGTH: 20
<212> TYPE: PRT
<213> ORGANISM: Human papillomavirus

<400> SEQUENCE: 41

Gln Leu Tyr Arg Thr Cys Lys Ala Ser Gly Thr Cys Pro Pro Asp Val
1               5                   10                  15

Ile Pro Lys Val
            20

<210> SEQ ID NO 42
<211> LENGTH: 20
<212> TYPE: PRT
<213> ORGANISM: Human papillomavirus

<400> SEQUENCE: 42

Gln Leu Tyr Arg Thr Cys Lys Ala Ser Gly Thr Cys Pro Pro Asp Val
1               5                   10                  15

Ile Pro Lys Val
            20

<210> SEQ ID NO 43
<211> LENGTH: 20
<212> TYPE: PRT
<213> ORGANISM: Human papillomavirus

<400> SEQUENCE: 43

Glu Leu Tyr Lys Thr Cys Lys Gln Ser Gly Thr Cys Pro Pro Asp Val
1               5                   10                  15

Ile Asn Lys Val
            20

<210> SEQ ID NO 44
<211> LENGTH: 20
<212> TYPE: PRT
<213> ORGANISM: Human papillomavirus

<400> SEQUENCE: 44

Asp Leu Tyr Arg Thr Cys Lys Ala Ala Gly Thr Cys Pro Pro Asp Val
1               5                   10                  15

Ile Pro Lys Val
            20

<210> SEQ ID NO 45

```
<211> LENGTH: 20
<212> TYPE: PRT
<213> ORGANISM: Human papillomavirus

<400> SEQUENCE: 45

Asp Leu Tyr Lys Thr Cys Lys Ala Ala Gly Thr Cys Pro Pro Asp Val
1               5                   10                  15

Ile Pro Lys Ile
            20

<210> SEQ ID NO 46
<211> LENGTH: 20
<212> TYPE: PRT
<213> ORGANISM: Human papillomavirus

<400> SEQUENCE: 46

Asp Leu Tyr Lys Thr Cys Lys Ala Ala Gly Thr Cys Pro Pro Asp Val
1               5                   10                  15

Ile Pro Lys Ile
            20

<210> SEQ ID NO 47
<211> LENGTH: 20
<212> TYPE: PRT
<213> ORGANISM: Human papillomavirus

<400> SEQUENCE: 47

Gln Leu Tyr Gln Thr Cys Lys Ala Ser Gly Thr Cys Pro Pro Asp Val
1               5                   10                  15

Ile Pro Lys Val
            20

<210> SEQ ID NO 48
<211> LENGTH: 20
<212> TYPE: PRT
<213> ORGANISM: Human papillomavirus

<400> SEQUENCE: 48

Gln Leu Tyr Gln Thr Cys Lys Ala Ser Gly Thr Cys Pro Pro Asp Val
1               5                   10                  15

Ile Pro Lys Val
            20

<210> SEQ ID NO 49
<211> LENGTH: 20
<212> TYPE: PRT
<213> ORGANISM: Human papillomavirus

<400> SEQUENCE: 49

Asp Leu Tyr Arg Thr Cys Lys Gln Ser Gly Thr Cys Pro Pro Asp Val
1               5                   10                  15

Val Pro Lys Val
            20

<210> SEQ ID NO 50
<211> LENGTH: 20
<212> TYPE: PRT
<213> ORGANISM: Human papillomavirus

<400> SEQUENCE: 50

Gln Leu Tyr Gln Thr Cys Lys Ala Ser Gly Thr Cys Pro Pro Asp Val
1               5                   10                  15
```

```
Ile Pro Lys Ile
            20

<210> SEQ ID NO 51
<211> LENGTH: 20
<212> TYPE: PRT
<213> ORGANISM: Human papillomavirus

<400> SEQUENCE: 51

His Ile Tyr Gln Ser Cys Lys Ala Ala Gly Thr Cys Pro Pro Asp Val
1               5                   10                  15

Leu Asn Lys Val
            20

<210> SEQ ID NO 52
<211> LENGTH: 20
<212> TYPE: PRT
<213> ORGANISM: Human papillomavirus

<400> SEQUENCE: 52

Asp Ile Tyr Arg Gly Cys Lys Ala Ser Asn Thr Cys Pro Pro Asp Val
1               5                   10                  15

Ile Asn Lys Val
            20

<210> SEQ ID NO 53
<211> LENGTH: 20
<212> TYPE: PRT
<213> ORGANISM: Human papillomavirus

<400> SEQUENCE: 53

Asn Leu Tyr Ala Lys Cys Gln Leu Ser Gly Asn Cys Leu Pro Asp Val
1               5                   10                  15

Lys Asn Lys Val
            20

<210> SEQ ID NO 54
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Gln, His or Glu
<220> FEATURE:
<221> NAME/KEY: MOD_RES
<222> LOCATION: (2)..(2)
<223> OTHER INFORMATION: Leu or Ile
<220> FEATURE:
<221> NAME/KEY: MOD_RES
<222> LOCATION: (4)..(4)
<223> OTHER INFORMATION: Lys, Pro, Arg, Gln or Ser
<220> FEATURE:
<221> NAME/KEY: MOD_RES
<222> LOCATION: (5)..(5)
<223> OTHER INFORMATION: Thr, Ser, Ala or Gly
<220> FEATURE:
<221> NAME/KEY: MOD_RES
<222> LOCATION: (8)..(8)
<223> OTHER INFORMATION: Gln, Ile, Val, Leu or Ala
<220> FEATURE:
<221> NAME/KEY: MOD_RES
<222> LOCATION: (9)..(9)
<223> OTHER INFORMATION: Ala, Ser or Thr
<220> FEATURE:
<221> NAME/KEY: MOD_RES
```

<222> LOCATION: (10)..(10)
<223> OTHER INFORMATION: Gly or Asn
<220> FEATURE:
<221> NAME/KEY: MOD_RES
<222> LOCATION: (11)..(11)
<223> OTHER INFORMATION: Thr or Asn
<220> FEATURE:
<221> NAME/KEY: MOD_RES
<222> LOCATION: (16)..(16)
<223> OTHER INFORMATION: Ile or Val
<220> FEATURE:
<221> NAME/KEY: MOD_RES
<222> LOCATION: (17)..(17)
<223> OTHER INFORMATION: Ile, Val or Gln
<220> FEATURE:
<221> NAME/KEY: MOD_RES
<222> LOCATION: (18)..(18)
<223> OTHER INFORMATION: Pro, Asn or Asp
<220> FEATURE:
<221> NAME/KEY: MOD_RES
<222> LOCATION: (19)..(19)
<223> OTHER INFORMATION: Lys or Arg
<220> FEATURE:
<221> NAME/KEY: MOD_RES
<222> LOCATION: (20)..(20)
<223> OTHER INFORMATION: Val, Ile or Leu

<400> SEQUENCE: 54

Xaa Xaa Tyr Xaa Xaa Cys Lys Xaa Xaa Xaa Xaa Cys Pro Pro Asp Xaa
1               5                   10                  15

Xaa Xaa Xaa Xaa Glu Gly
            20

<210> SEQ ID NO 55
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Gln, His or Glu
<220> FEATURE:
<221> NAME/KEY: MOD_RES
<222> LOCATION: (2)..(2)
<223> OTHER INFORMATION: Leu or Ile
<220> FEATURE:
<221> NAME/KEY: MOD_RES
<222> LOCATION: (4)..(4)
<223> OTHER INFORMATION: Lys, Pro, Arg, Gln or Ser
<220> FEATURE:
<221> NAME/KEY: MOD_RES
<222> LOCATION: (5)..(5)
<223> OTHER INFORMATION: Thr, Ser, Ala or Gly
<220> FEATURE:
<221> NAME/KEY: MOD_RES
<222> LOCATION: (8)..(8)
<223> OTHER INFORMATION: Gln, Ile, Val, Leu or Ala
<220> FEATURE:
<221> NAME/KEY: MOD_RES
<222> LOCATION: (9)..(9)
<223> OTHER INFORMATION: Ala, Ser or Thr
<220> FEATURE:
<221> NAME/KEY: MOD_RES
<222> LOCATION: (10)..(10)
<223> OTHER INFORMATION: Gly or Asn
<220> FEATURE:
<221> NAME/KEY: MOD_RES
<222> LOCATION: (11)..(11)
<223> OTHER INFORMATION: Thr or Asn
<220> FEATURE:
<221> NAME/KEY: MOD_RES
<222> LOCATION: (16)..(16)
<223> OTHER INFORMATION: Ile or Val

```
<220> FEATURE:
<221> NAME/KEY: MOD_RES
<222> LOCATION: (17)..(17)
<223> OTHER INFORMATION: Ile, Val or Gln
<220> FEATURE:
<221> NAME/KEY: MOD_RES
<222> LOCATION: (18)..(18)
<223> OTHER INFORMATION: Pro, Asn or Asp
<220> FEATURE:
<221> NAME/KEY: MOD_RES
<222> LOCATION: (19)..(19)
<223> OTHER INFORMATION: Lys or Arg
<220> FEATURE:
<221> NAME/KEY: MOD_RES
<222> LOCATION: (20)..(20)
<223> OTHER INFORMATION: Val, Ile or Leu

<400> SEQUENCE: 55

Xaa Xaa Tyr Xaa Xaa Cys Lys Xaa Xaa Xaa Xaa Cys Pro Pro Asp Xaa
1               5                   10                  15

Xaa Xaa Xaa Xaa Glu Gly
            20

<210> SEQ ID NO 56
<211> LENGTH: 22
<212> TYPE: PRT
<213> ORGANISM: Human papillomavirus

<400> SEQUENCE: 56

Gln Leu Tyr Lys Thr Cys Lys Gln Ala Gly Thr Cys Pro Pro Asp Ile
1               5                   10                  15

Ile Pro Lys Val Glu Gly
            20

<210> SEQ ID NO 57
<211> LENGTH: 21
<212> TYPE: PRT
<213> ORGANISM: Human papillomavirus

<400> SEQUENCE: 57

Leu Tyr Lys Thr Cys Lys Gln Ala Gly Thr Cys Pro Pro Asp Ile Ile
1               5                   10                  15

Pro Lys Val Glu Gly
            20

<210> SEQ ID NO 58
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ctgtttgcat gttttataaa gggtgacttt tctattcaca ttttctgc                 48

<210> SEQ ID NO 59
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gcaggtacat gtccacctga cacccaaaca acagatgaca gg                       42
```

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
ccgctgaatt caatatggcg ttgtggcaac aag                                33

<210> SEQ ID NO 61
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
gcatgaggta ccgcttttat ttcttttttct tttttgcagg c                      41

<210> SEQ ID NO 62
<211> LENGTH: 70
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
gtataatgtc aggtggacat gtacctgcct gtttgcatgt tttataaagt tgggtgactt   60
ttctattcac                                                          70

<210> SEQ ID NO 63
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
ctaaggttac ccaaacaaca gatgacagga aacaaacagg cc                      42

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
cggccgcggg gtgactttc tattc                                          25

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
cggccgcgga cccaaacaac agatg                                         25

<210> SEQ ID NO 66
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ggcgacacaa acgttctgca aaacgcacaa aacgtgcatc ggctacccaa ctttataaaa      60
catgcccgc      69

<210> SEQ ID NO 67
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gggcatgttt tataaagttg ggtagccgat gcacgttttg tgcgttttgc agaacgtttg      60
tgtcgccgc      69

<210> SEQ ID NO 68
<211> LENGTH: 129
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ggaaggttga aggcaaaact attgctgatc aaatattaca atatggaagt atgggtgtat      60
tttttggtgg gttaggaatt ggaacagggt cgggtacagg cggacgcact gggtatattc     120
cattgccgc     129

<210> SEQ ID NO 69
<211> LENGTH: 129
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ggcaatggaa tatacccagt gcgtccgcct gtacccgacc ctgttccaat tcctaaccca      60
ccaaaaaata cacccatact tccatattgt aatatttgat cagcaatagt tttgccttca     120
accttccgc     129

<210> SEQ ID NO 70
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gcatgaccgc ggttgggaac aaggcctccc acagctac      38

```
<210> SEQ ID NO 71
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gcatgaccgc ggagtttctt ccactaaaga aac                                33

<210> SEQ ID NO 72
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gcatgaccgc ggattgatgc tggtgcacca ac                                 32

<210> SEQ ID NO 73
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gcatgaccgc ggagtagtaa cagtattatt aatatc                             36

<210> SEQ ID NO 74
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gcatgaccgc ggaataatac tgttactact gttactac                           38

<210> SEQ ID NO 75
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gcatgaccgc ggttctgcag gtgttggagg ctgcaatac                          39

<210> SEQ ID NO 76
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gcatgaccgc ggccaacacc tgcagaaact ggag                               34

<210> SEQ ID NO 77
```

```
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gcatgaccgc ggtgtatcca taggaatttc ttcataatta tg                            42

<210> SEQ ID NO 78
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gcatgaccgc gggcatcggc tacccaactt tataaaac                                 38

<210> SEQ ID NO 79
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gcatgaccgc ggagaaacta tagaaggatc agaagggc                                 38

<210> SEQ ID NO 80
<211> LENGTH: 1416
<212> TYPE: DNA
<213> ORGANISM: Human papillomavirus

<400> SEQUENCE: 80
atgcgacaca acgttctgc aaaacgcaca aaacgtgcat cggctaccca actttataaa          60
acatgcaaac aggcaggtac atgtccacct gacattatac ctaaggttga aggcaaaact        120
attgctgatc aaatattaca atatggaagt atgggtgtat ttttggtgg gttaggaatt         180 ggaacagggt cgggtacagg cggacgcact gggtatattc cattgggaac aaggcctccc        240
acagctacag atacacttgc tcctgtaaga ccccctttaa cagtagatcc tgtgggccct        300
tctgatcctt ctatagtttc tttagtggaa gaaactagtt ttattgatgc tggtgcacca        360
acatctgtac cttccattcc cccagatgta tcaggattta gtattactac ttcaactgat        420
accacacctg ctatattaga tattaataat actgttacta ctgttactac acataataat        480
cccactttca ctgacccatc tgtattgcag cctccaacac ctgcagaaac tggagggcat        540
tttacacttt catcatccac tattagtaca cataattatg aagaaattcc tatggataca        600
tttattgtta gcacaaaccc taacacagta actagtagca cacccatacc agggtctcgc        660
ccagtggcac gcctaggatt atatagtcgc acaacacaac aagttaaagt tgtagaccct        720
gcttttgtaa ccactcccac taaacttatt acatatgata atcctgcata tgaaggtata        780
gatgtggata atacattata tttttctagt aatgataata gtattaatat agctccagat        840
cctgactttt tggatatagt tgctttacat aggccagcat taacctctag gcgtactggc        900
ataaggtaca gtagaattgg taataaacaa acactacgta ctcgtagtgg aaaatctata        960
ggtgctaagg tacattatta ttatgatttt agtaccattg atcctgcaga agaaatagaa       1020
```

-continued

```
ttacaaacta taacaccttc tacatatact accacttcac atgcagcctc acctacttct    1080
attaataatg gattatatga tatttatgca gatgacttta ttacagatac ttctacaacc    1140
ccggtaccat ctgtaccctc tacatcttta tcaggttata ttcctgcaaa tacaacaatt    1200
ccttttggtg gtgcatacaa tattccttta gtatcaggtc ctgatatacc cattaatata    1260
actgaccaag ctccttcatt aattcctata gttccagggt ctccacaata tacaattatt    1320
gctgatgcag gtgactttta tttacatcct agtattaca tgttacgaaa acgacgtaaa    1380
cgtttaccat attttttttc agatgtctct ttggct                              1416

<210> SEQ ID NO 81
<211> LENGTH: 473
<212> TYPE: PRT
<213> ORGANISM: Human papillomavirus

<400> SEQUENCE: 81

Met Arg His Lys Arg Ser Ala Lys Arg Thr Lys Arg Ala Ser Ala Thr
  1               5                  10                  15

Gln Leu Tyr Lys Thr Cys Lys Gln Ala Gly Thr Cys Pro Pro Asp Ile
                 20                  25                  30

Ile Pro Lys Val Glu Gly Lys Thr Ile Ala Asp Gln Ile Leu Gln Tyr
             35                  40                  45

Gly Ser Met Gly Val Phe Phe Gly Gly Leu Gly Ile Gly Thr Gly Ser
         50                  55                  60

Gly Thr Gly Gly Arg Thr Gly Tyr Ile Pro Leu Gly Thr Arg Pro Pro
 65                  70                  75                  80

Thr Ala Thr Asp Thr Leu Ala Pro Val Arg Pro Pro Leu Thr Val Asp
                 85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Ser Val Pro Ser Ile Pro Pro
        115                 120                 125

Asp Val Ser Gly Phe Ser Ile Thr Thr Ser Thr Asp Thr Thr Pro Ala
    130                 135                 140

Ile Leu Asp Ile Asn Asn Thr Val Thr Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190

Tyr Glu Glu Ile Pro Met Asp Thr Phe Ile Val Ser Thr Asn Pro Asn
        195                 200                 205

Thr Val Thr Ser Ser Thr Pro Ile Pro Gly Ser Arg Pro Val Ala Arg
    210                 215                 220

Leu Gly Leu Tyr Ser Arg Thr Thr Gln Gln Val Lys Val Val Asp Pro
225                 230                 235                 240

Ala Phe Val Thr Thr Pro Thr Lys Leu Ile Thr Tyr Asp Asn Pro Ala
                245                 250                 255

Tyr Glu Gly Ile Asp Val Asp Asn Thr Leu Tyr Phe Ser Ser Asn Asp
            260                 265                 270

Asn Ser Ile Asn Ile Ala Pro Asp Pro Asp Phe Leu Asp Ile Val Ala
        275                 280                 285

Leu His Arg Pro Ala Leu Thr Ser Arg Arg Thr Gly Ile Arg Tyr Ser
    290                 295                 300
```

```
Arg Ile Gly Asn Lys Gln Thr Leu Arg Thr Arg Ser Gly Lys Ser Ile
305                 310                 315                 320

Gly Ala Lys Val His Tyr Tyr Tyr Asp Phe Ser Thr Ile Asp Pro Ala
                325                 330                 335

Glu Glu Ile Glu Leu Gln Thr Ile Thr Pro Ser Thr Tyr Thr Thr Thr
            340                 345                 350

Ser His Ala Ala Ser Pro Thr Ser Ile Asn Asn Gly Leu Tyr Asp Ile
        355                 360                 365

Tyr Ala Asp Asp Phe Ile Thr Asp Thr Ser Thr Thr Pro Val Pro Ser
370                 375                 380

Val Pro Ser Thr Ser Leu Ser Gly Tyr Ile Pro Ala Asn Thr Thr Ile
385                 390                 395                 400

Pro Phe Gly Gly Ala Tyr Asn Ile Pro Leu Val Ser Gly Pro Asp Ile
                405                 410                 415

Pro Ile Asn Ile Thr Asp Gln Ala Pro Ser Leu Ile Pro Ile Val Pro
            420                 425                 430

Gly Ser Pro Gln Tyr Thr Ile Ile Ala Asp Ala Gly Asp Phe Tyr Leu
        435                 440                 445

His Pro Ser Tyr Tyr Met Leu Arg Lys Arg Arg Lys Arg Leu Pro Tyr
    450                 455                 460

Phe Phe Ser Asp Val Ser Leu Ala Ala
465                 470

<210> SEQ ID NO 82
<211> LENGTH: 1488
<212> TYPE: DNA
<213> ORGANISM: Bovine papillomavirus

<400> SEQUENCE: 82
atggcgttgt ggcaacaagg ccagaagctg tatctccctc aaccccctgt aagcaaggtg      60
ctttgcagtg aaacctatgt gcaaagaaaa agcattttt  atcatgcaga aacggagcgc     120
ctgctaacta taggacatcc atattaccca gtgtctatcg gggccaaaac tgttcctaag     180
gtctctgcaa atcagtatag ggtatttaaa atacaactac ctgatcccaa tcaatttgca     240
ctacctgaca ggactgttca aacccaagt  aaagagcggc tggtgtgggc agtcataggt     300
gtgcaggtgt ccagagggca gcctcttgga ggtactgtaa ctgggcaccc cacttttaat     360
gctttgcttg atgcagaaaa tgtgaataga aagtcacca  cccaaacaac agatgacagg     420
aaacaaacag gcctagatgc taagcaacaa cagattctgt tgctaggctg tacccctgct     480
gaaggggaat attggacaac agcccgtcca tgtgttactg atcgtctaga aaatggcgcc     540
tgccctcctc ttgaattaaa aaacaagcac atagaagatg gggatatgat ggaaattggg     600
tttggtgcag ccaacttcaa agaaattaat gcaagtaaat cagatctacc tcttgacatt     660
caaaatgaga tctgcttgta cccagactac ctcaaaatgg ctgaggacgc tgctggtaat     720
agcatgttct tttttgcaag gaagaacag  gtgtatgtta cacacatctg gaccagaggg     780
ggctcggaga agaagccccc taccacagat ttttatttaa agaataataa aggggatgcc     840
acccttaaaa tacccagtgt gcattttggt agtcccagtg gctcactagt ctcaactgat     900
aatcaaattt ttaatcggcc ctactggcta ttccgtgccc agggcatgaa caatggaatt     960
gcatggaata atttattgtt tttaacagtg ggggacaata cacgtggtac taatcttacc    1020
ataagtgtag cctcagatgg aacccactca acagagtata tagctcaaa  attcaatgta    1080 taccatagac atatggaaga atataagcta gcctttatat tagagctatg ctctgtggaa    1140
```

-continued

```
atcacagctc aaactgtgtc acatctgcaa ggacttatgc cctctgtgct tgaaaattgg    1200
gaaataggtg tgcagcctcc tacctcatcg atattagagg acacctatcg ctatatagag    1260
tctcctgcaa ctaaatgtgc aagcaatgta attcctgcaa aagaagaccc ttatgcaggg    1320
tttaagtttt ggaacataga tcttaaagaa aagctttctt tggacttaga tcaatttccc    1380
ttgggaagaa gattttagc acagcaaggg gcaggatgtt caactgtgag aaaacgaaga     1440
attagccaaa aaacttccag taagcctgca aaaaaaaaaa aaaaataa                 1488
```

<210> SEQ ID NO 83
<211> LENGTH: 495
<212> TYPE: PRT
<213> ORGANISM: Bovine papillomavirus

<400> SEQUENCE: 83

```
Met Ala Leu Trp Gln Gln Gly Gln Lys Leu Tyr Leu Pro Pro Thr Pro
 1               5                  10                  15

Val Ser Lys Val Leu Cys Ser Glu Thr Tyr Val Gln Arg Lys Ser Ile
            20                  25                  30

Phe Tyr His Ala Glu Thr Glu Arg Leu Leu Thr Ile Gly His Pro Tyr
        35                  40                  45

Tyr Pro Val Ser Ile Gly Ala Lys Thr Val Pro Lys Val Ser Ala Asn
    50                  55                  60

Gln Tyr Arg Val Phe Lys Ile Gln Leu Pro Asp Pro Asn Gln Phe Ala
65                  70                  75                  80

Leu Pro Asp Arg Thr Val His Asn Pro Ser Lys Glu Arg Leu Val Trp
                85                  90                  95

Ala Val Ile Gly Val Gln Val Ser Arg Gly Gln Pro Leu Gly Gly Thr
            100                 105                 110

Val Thr Gly His Pro Thr Phe Asn Ala Leu Leu Asp Ala Glu Asn Val
        115                 120                 125

Asn Arg Lys Val Thr Thr Gln Thr Thr Asp Asp Arg Lys Gln Thr Gly
    130                 135                 140

Leu Asp Ala Lys Gln Gln Gln Ile Leu Leu Leu Gly Cys Thr Pro Ala
145                 150                 155                 160

Glu Gly Glu Tyr Trp Thr Thr Ala Arg Pro Cys Val Thr Asp Arg Leu
                165                 170                 175

Glu Asn Gly Ala Cys Pro Pro Leu Glu Leu Lys Asn Lys His Ile Glu
            180                 185                 190

Asp Gly Asp Met Met Glu Ile Gly Phe Gly Ala Ala Asn Phe Lys Glu
        195                 200                 205

Ile Asn Ala Ser Lys Ser Asp Leu Pro Leu Asp Ile Gln Asn Glu Ile
    210                 215                 220

Cys Leu Tyr Pro Asp Tyr Leu Lys Met Ala Glu Asp Ala Ala Gly Asn
225                 230                 235                 240

Ser Met Phe Phe Phe Ala Arg Lys Glu Gln Val Tyr Val Arg His Ile
                245                 250                 255

Trp Thr Arg Gly Gly Ser Glu Lys Glu Ala Pro Thr Thr Asp Phe Tyr
            260                 265                 270

Leu Lys Asn Asn Lys Gly Asp Ala Thr Leu Lys Ile Pro Ser Val His
        275                 280                 285

Phe Gly Ser Pro Ser Gly Ser Leu Val Ser Thr Asp Asn Gln Ile Phe
    290                 295                 300

Asn Arg Pro Tyr Trp Leu Phe Arg Ala Gln Gly Met Asn Asn Gly Ile
305                 310                 315                 320
```

```
Ala Trp Asn Asn Leu Leu Phe Leu Thr Val Gly Asp Asn Thr Arg Gly
            325                 330                 335

Thr Asn Leu Thr Ile Ser Val Ala Ser Asp Gly Thr Pro Leu Thr Glu
        340                 345                 350

Tyr Asp Ser Ser Lys Phe Asn Val Tyr His Arg His Met Glu Glu Tyr
            355                 360                 365

Lys Leu Ala Phe Ile Leu Glu Leu Cys Ser Val Glu Ile Thr Ala Gln
        370                 375                 380

Thr Val Ser His Leu Gln Gly Leu Met Pro Ser Val Leu Glu Asn Trp
385                 390                 395                 400

Glu Ile Gly Val Gln Pro Pro Thr Ser Ser Ile Leu Glu Asp Thr Tyr
            405                 410                 415

Arg Tyr Ile Glu Ser Pro Ala Thr Lys Cys Ala Ser Asn Val Ile Pro
        420                 425                 430

Ala Lys Glu Asp Pro Tyr Ala Gly Phe Lys Phe Trp Asn Ile Asp Leu
            435                 440                 445

Lys Glu Lys Leu Ser Leu Asp Leu Asp Gln Phe Pro Leu Gly Arg Arg
        450                 455                 460

Phe Leu Ala Gln Gln Gly Ala Gly Cys Ser Thr Val Arg Lys Arg Arg
465                 470                 475                 480

Ile Ser Gln Lys Thr Ser Ser Lys Pro Ala Lys Lys Lys Lys
            485                 490                 495

<210> SEQ ID NO 84
<211> LENGTH: 1518
<212> TYPE: DNA
<213> ORGANISM: Human papillomavirus

<400> SEQUENCE: 84
atgtctcttt ggctgcctag tgaggccact gtctacttgc ctcctgtccc agtatctaag      60
gttgtaagca cggatgaata tgttgcacgc acaaacatat attatcatgc aggaacatcc     120
agactacttg cagttggaca tccctatttt cctattaaaa aacctaacaa taacaaaata     180
ttagttccta agtatcagg attacaatac agggtattta gaatacattt acctgacccc     240
aataagtttg gttttcctga cacctcattt tataatccag atacacagcg gctggtttgg     300
gcctgtgtag gtgttgaggt aggtcgtggt cagccattag tgtgggcat tagtggccat     360 cctttattaa ataaattgga tgacacagaa aatgctagtg cttatgcagc aaatgcaggt     420
gtggataata gagaatgtat atctatggat tacaaacaaa cacaattgtg tttaattggt     480
tgcaaaccac ctatagggga acactggggc aaaggatccc catgtaccaa tgttgcagta     540
aatccaggtg attgtccacc attagagtta ataaacacag ttattcagga tggtgatatg     600
gttgatactg gctttggtgc tatggacttt actacattac aggctaacaa agtgaagtt     660 ccactggata tttgtacatc tatttgcaaa tatccagatt atattaaaat ggtgtcagaa     720
ccatatggcg acagcttatt ttttatttta cgaagggaac aaatgtttgt tagacattta     780
tttaataggg ctggtactgt tggtgaaaat gtaccagacg atttatacat taaaggctct     840
gggtctactg caatttagc cagttcaat tatttttccta cacctagtgg ttctatggtt     900
acctctgatg cccaaatatt caataaacct tattggttac aacgagcaca gggccacaat     960
aatggcattt gtgggtgta ccaactattt gttactgttg ttgatactac acgcagtaca    1020
aatatgtcat tatgtgctgc catatctact tcagaaacta catataaaaa tactaacttt    1080
aaggagtacc tacgacatgg ggaggaatat gatttacagt ttatttttca actgtgcaaa    1140
```

```
ataaccttaa ctgcagacgt tatgacatac atacattcta tgaattccac tattttggag   1200
gactggaatt ttggtctaca acctccccca ggaggcacac tagaagatac ttataggttt   1260
gtaacatccc aggcaattgc ttgtcaaaaa catacacctc cagcacctaa agaagatccc   1320
cttaaaaaat acacttttgg gaagtaaatt ttaaaggaaa agtttctgc agacctagat    1380 cagtttcctt taggacgcaa attttactaa caagcaggat tgaaggccaa accaaaattt   1440
acattaggaa aacgaaaagc tacacccacc acctcatcta cctctacaac tgctaaacgc   1500
aaaaaacgta agctgtaa                                                 1518
```

<210> SEQ ID NO 85
<211> LENGTH: 505
<212> TYPE: PRT
<213> ORGANISM: Human papillomavirus

<400> SEQUENCE: 85

```
Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
                20                  25                  30

Ile Tyr Tyr His Ala Gly Thr Ser Arg Leu Leu Ala Val Gly His Pro
            35                  40                  45

Tyr Phe Pro Ile Lys Lys Pro Asn Asn Asn Lys Ile Leu Val Pro Lys
        50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Thr Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300
```

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Asp Thr
            325                 330                 335

Thr Arg Ser Thr Asn Met Ser Leu Cys Ala Ala Ile Thr Ser Glu
        340                 345                 350

Thr Thr Tyr Lys Asn Thr Asn Phe Lys Glu Tyr Leu Arg His Gly Glu
            355                 360                 365

Glu Tyr Asp Leu Gln Phe Ile Phe Gln Leu Cys Lys Ile Thr Leu Thr
        370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Leu Glu Asp
            405                 410                 415

Thr Tyr Arg Phe Val Thr Ser Gln Ala Ile Ala Cys Gln Lys His Thr
        420                 425                 430

Pro Pro Ala Pro Lys Glu Asp Pro Leu Lys Lys Tyr Thr Phe Trp Glu
            435                 440                 445

Val Asn Leu Lys Glu Lys Phe Ser Ala Asp Leu Asp Gln Phe Pro Leu
450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
            485                 490                 495

Thr Ala Lys Arg Lys Lys Arg Lys Leu
            500                 505

<210> SEQ ID NO 86
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
aacaatgtgt agacattata aacgagc                                            27

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
atggtacart gggcatwtga                                                    20

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gaggytgcaa ccaaaamtgr ct                                                 22

```
<210> SEQ ID NO 89
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gggtggtaac tacctgctg                                                  19

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ctcttgtcag gaactctgta cg                                              22

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
cagaaccgtc cggctggtgg                                                 20

<210> SEQ ID NO 92
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
cccacccgcc cagtgccac                                                  19

<210> SEQ ID NO 93
<211> LENGTH: 6
<212> TYPE: PRT
<213> ORGANISM: Bovine papillomavirus

<400> SEQUENCE: 93

Asp Thr Tyr Arg Tyr Ile
1               5

<210> SEQ ID NO 94
<211> LENGTH: 14
<212> TYPE: PRT
<213> ORGANISM: Human papillomavirus

<400> SEQUENCE: 94

Leu Tyr Lys Thr Cys Lys Gln Ala Gly Thr Cys Pro Pro Asp
1               5                   10

<210> SEQ ID NO 95
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Gln or His
<220> FEATURE:
<221> NAME/KEY: MOD_RES
<222> LOCATION: (2)..(2)
<223> OTHER INFORMATION: Leu or Ile
<220> FEATURE:
<221> NAME/KEY: MOD_RES
<222> LOCATION: (4)..(4)
<223> OTHER INFORMATION: Lys, Pro, Arg, Gln or Ser
<220> FEATURE:
<221> NAME/KEY: MOD_RES
<222> LOCATION: (5)..(5)
<223> OTHER INFORMATION: Thr, Ser or Ala
<220> FEATURE:
<221> NAME/KEY: MOD_RES
<222> LOCATION: (8)..(8)
<223> OTHER INFORMATION: Gln, Ile, Val, Leu or Ala
<220> FEATURE:
<221> NAME/KEY: MOD_RES
<222> LOCATION: (9)..(9)
<223> OTHER INFORMATION: Ala, Ser or Thr
<220> FEATURE:
<221> NAME/KEY: MOD_RES
<222> LOCATION: (10)..(10)
<223> OTHER INFORMATION: Gly or Asn
<220> FEATURE:
<221> NAME/KEY: MOD_RES
<222> LOCATION: (11)..(11)
<223> OTHER INFORMATION: Thr or Asn
<220> FEATURE:
<221> NAME/KEY: MOD_RES
<222> LOCATION: (16)..(16)
<223> OTHER INFORMATION: Ile or Val
<220> FEATURE:
<221> NAME/KEY: MOD_RES
<222> LOCATION: (17)..(17)
<223> OTHER INFORMATION: Ile, Val or Gln
<220> FEATURE:
<221> NAME/KEY: MOD_RES
<222> LOCATION: (18)..(18)
<223> OTHER INFORMATION: Pro, Asn or Asp
<220> FEATURE:
<221> NAME/KEY: MOD_RES
<222> LOCATION: (19)..(19)
<223> OTHER INFORMATION: Lys or Arg
<220> FEATURE:
<221> NAME/KEY: MOD_RES
<222> LOCATION: (20)..(20)
<223> OTHER INFORMATION: Val or Ile

<400> SEQUENCE: 95

Xaa Xaa Tyr Xaa Xaa Cys Lys Xaa Xaa Xaa Xaa Cys Pro Pro Asp Xaa
1               5                   10                  15

Xaa Xaa Xaa Xaa
            20

<210> SEQ ID NO 96
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Gln or His
<220> FEATURE:
<221> NAME/KEY: MOD_RES
<222> LOCATION: (2)..(2)
```

```
<223> OTHER INFORMATION: Leu or Ile
<220> FEATURE:
<221> NAME/KEY: MOD_RES
<222> LOCATION: (4)..(4)
<223> OTHER INFORMATION: Lys, Pro, Arg, Gln or Ser
<220> FEATURE:
<221> NAME/KEY: MOD_RES
<222> LOCATION: (5)..(5)
<223> OTHER INFORMATION: Thr, Ser or Ala
<220> FEATURE:
<221> NAME/KEY: MOD_RES
<222> LOCATION: (8)..(8)
<223> OTHER INFORMATION: Gln, Ile, Val, Leu or Ala
<220> FEATURE:
<221> NAME/KEY: MOD_RES
<222> LOCATION: (9)..(9)
<223> OTHER INFORMATION: Ala, Ser or Thr
<220> FEATURE:
<221> NAME/KEY: MOD_RES
<222> LOCATION: (10)..(10)
<223> OTHER INFORMATION: Gly or Asn
<220> FEATURE:
<221> NAME/KEY: MOD_RES
<222> LOCATION: (11)..(11)
<223> OTHER INFORMATION: Thr or Asn
<220> FEATURE:
<221> NAME/KEY: MOD_RES
<222> LOCATION: (16)..(16)
<223> OTHER INFORMATION: Ile or Val
<220> FEATURE:
<221> NAME/KEY: MOD_RES
<222> LOCATION: (17)..(17)
<223> OTHER INFORMATION: Ile, Val or Gln
<220> FEATURE:
<221> NAME/KEY: MOD_RES
<222> LOCATION: (18)..(18)
<223> OTHER INFORMATION: Pro, Asn or Asp
<220> FEATURE:
<221> NAME/KEY: MOD_RES
<222> LOCATION: (19)..(19)
<223> OTHER INFORMATION: Lys or Arg
<220> FEATURE:
<221> NAME/KEY: MOD_RES
<222> LOCATION: (20)..(20)
<223> OTHER INFORMATION: Val or Ile

<400> SEQUENCE: 96

Xaa Xaa Tyr Xaa Xaa Cys Lys Xaa Xaa Xaa Xaa Cys Pro Pro Asp Xaa
1               5                   10                  15

Xaa Xaa Xaa Xaa
            20

<210> SEQ ID NO 97
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Gln or His
<220> FEATURE:
<221> NAME/KEY: MOD_RES
<222> LOCATION: (2)..(2)
<223> OTHER INFORMATION: Leu or Ile
<220> FEATURE:
<221> NAME/KEY: MOD_RES
<222> LOCATION: (4)..(4)
<223> OTHER INFORMATION: Lys, Pro, Arg, Gln or Ser
<220> FEATURE:
<221> NAME/KEY: MOD_RES
<222> LOCATION: (5)..(5)
<223> OTHER INFORMATION: Thr, Ser or Ala
<220> FEATURE:
```

```
<221> NAME/KEY: MOD_RES
<222> LOCATION: (8)..(8)
<223> OTHER INFORMATION: Gln, Ile, Val, Leu or Ala
<220> FEATURE:
<221> NAME/KEY: MOD_RES
<222> LOCATION: (9)..(9)
<223> OTHER INFORMATION: Ala, Ser or Thr
<220> FEATURE:
<221> NAME/KEY: MOD_RES
<222> LOCATION: (10)..(10)
<223> OTHER INFORMATION: Gly or Asn
<220> FEATURE:
<221> NAME/KEY: MOD_RES
<222> LOCATION: (11)..(11)
<223> OTHER INFORMATION: Thr or Asn
<220> FEATURE:
<221> NAME/KEY: MOD_RES
<222> LOCATION: (16)..(16)
<223> OTHER INFORMATION: Ile or Val
<220> FEATURE:
<221> NAME/KEY: MOD_RES
<222> LOCATION: (17)..(17)
<223> OTHER INFORMATION: Ile, Val or Gln
<220> FEATURE:
<221> NAME/KEY: MOD_RES
<222> LOCATION: (18)..(18)
<223> OTHER INFORMATION: Pro, Asn or Asp
<220> FEATURE:
<221> NAME/KEY: MOD_RES
<222> LOCATION: (19)..(19)
<223> OTHER INFORMATION: Lys or Arg
<220> FEATURE:
<221> NAME/KEY: MOD_RES
<222> LOCATION: (20)..(20)
<223> OTHER INFORMATION: Val or Ile

<400> SEQUENCE: 97

Xaa Xaa Tyr Xaa Xaa Cys Lys Xaa Xaa Xaa Xaa Cys Pro Pro Asp Xaa
1               5                   10                  15

Xaa Xaa Xaa Xaa Glu Gly
            20

<210> SEQ ID NO 98
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Gln or His
<220> FEATURE:
<221> NAME/KEY: MOD_RES
<222> LOCATION: (2)..(2)
<223> OTHER INFORMATION: Leu or Ile
<220> FEATURE:
<221> NAME/KEY: MOD_RES
<222> LOCATION: (4)..(4)
<223> OTHER INFORMATION: Lys, Pro, Arg, Gln or Ser
<220> FEATURE:
<221> NAME/KEY: MOD_RES
<222> LOCATION: (5)..(5)
<223> OTHER INFORMATION: Thr, Ser or Ala
<220> FEATURE:
<221> NAME/KEY: MOD_RES
<222> LOCATION: (8)..(8)
<223> OTHER INFORMATION: Gln, Ile, Val, Leu or Ala
<220> FEATURE:
<221> NAME/KEY: MOD_RES
<222> LOCATION: (9)..(9)
<223> OTHER INFORMATION: Ala, Ser or Thr
<220> FEATURE:
<221> NAME/KEY: MOD_RES
<222> LOCATION: (10)..(10)
```

```
<223> OTHER INFORMATION: Gly or Asn
<220> FEATURE:
<221> NAME/KEY: MOD_RES
<222> LOCATION: (11)..(11)
<223> OTHER INFORMATION: Thr or Asn
<220> FEATURE:
<221> NAME/KEY: MOD_RES
<222> LOCATION: (16)..(16)
<223> OTHER INFORMATION: Ile or Val
<220> FEATURE:
<221> NAME/KEY: MOD_RES
<222> LOCATION: (17)..(17)
<223> OTHER INFORMATION: Ile, Val or Gln
<220> FEATURE:
<221> NAME/KEY: MOD_RES
<222> LOCATION: (18)..(18)
<223> OTHER INFORMATION: Pro, Asn or Asp
<220> FEATURE:
<221> NAME/KEY: MOD_RES
<222> LOCATION: (19)..(19)
<223> OTHER INFORMATION: Lys or Arg
<220> FEATURE:
<221> NAME/KEY: MOD_RES
<222> LOCATION: (20)..(20)
<223> OTHER INFORMATION: Val or Ile

<400> SEQUENCE: 98

Xaa Xaa Tyr Xaa Xaa Cys Lys Xaa Xaa Xaa Xaa Cys Pro Pro Asp Xaa
1               5                   10                  15

Xaa Xaa Xaa Xaa Glu Gly
            20
```

PAPILLOMAVIRUS-LIKE PARTICLES (VLP) AS BROAD SPECTRUM HUMAN PAPILLOMAVIRUS (HPV) VACCINES

This application is a National Stage Application of International Application No. PCT/US2010/030757, filed Apr. 12, 2010, which claims priority to U.S. Provisional application 61/168,445, filed Apr. 10, 2009, both of which are incorporated by reference herein in their entirety.

This application claims the benefit of the filing date of U.S. Provisional Patent Application 61/168,445, filed Apr. 10, 2009, which is incorporated by reference in its entirety herein.

This invention was made with government support under grant number P50 CA098252 awarded by the National Cancer Institute. The government has certain rights in the invention.

SEQUENCE LISTING

The instant application contains a Sequence Listing which has been submitted in ASCII format via EFS-WEB and is hereby incorporated by reference in its entirety. Said ASCII copy, created on Feb. 17, 2011, is named "22402860.text" and is 49,480 bytes in size.

BACKGROUND INFORMATION

The more than one hundred types of human papillomaviruses (HPV) identified to date (de Villiers et al. (2004) *Virology* 22, 670-80) are the etiological agents of skin and mucosal papillomas or warts. Persistent infection with high-risk mucosal types, most often HPV16 and HPV18, cause cervical cancer, which constitutes the second leading fatal cancer in women worldwide, causing 274,000 deaths per year. Substantial morbidity results from other non-cervical HPV-related conditions, such as anogenital warts, vulval, vaginal, penile, anal or oropharyngeal cancer.

The development of current prophylactic papillomavirus vaccines was launched by observations that recombinantly expressed major capsid protein L1 self-assembles into virus-like particles (VLP). These empty viral capsids are composed of 360 L1 molecules and resemble native virions in both structure and immunogenicity, yet are non-oncogenic and non-infectious. Moreover, VLP cannot replicate because the cells in which VLP are made contain only L1 and no other papillomavirus genes. Subunit VLP vaccines induce high-titer and type-restricted antibody responses to conformational L1 epitopes (Christensen et al. (1990) *J Virol* 64, 3151-3156); Kirnbauer et al. (1992) *Proc Natl Acad Sci USA* 89, 12180-12184; Rose et al. (1994) *J Gen Virol* 75, 2445-9; Suzich et al. (1995) *Proc Natl Acad Sci USA* 92, 11553-11557). When applied to women prior to infection, available vaccines targeting the most prevalent high-risk types, HPV16 and HPV18, have demonstrated up to 100% efficacy against persistent infection and associated disease caused by the included types, and thus are potentially able to prevent about 70% of cervical high grade dysplasias and probably cancers. Therefore, use of currently licensed L1 vaccines necessitates continuation of cytological cervical screening of women. The prevention of 96% of cervical cancer would require immunity to 7 high-risk HPV types (16/18/31/33/45/52/58) (Munoz et al. (2004) *Int J Cancer* 111, 278-85) and the development of more highly multivalent (and presumably costly) L1 VLP vaccines.

The search for alternative broader-spectrum immunogens drew attention to the minor capsid protein L2, which is immunogenically subdominant in the context of co-expressed L1 plus L2 capsids (Roden et al. (2000) *Virology* 270, 254-257) Immunization of animals with amino (N)-terminal peptide of L2 demonstrated its ability to elicit low-titer neutralizing antibodies that protect against challenge with cognate papillomavirus (PV) types in vivo (Embers et al. (2002) *J Virol* 76, 9798-805; Gaukroger et al. (1996) *J Gen Virol* 77 (Pt 7), 1577-83), cross-neutralize heterologous PV types in vitro (Kawana et al. (1999) *J Virol* 73, 6188-90; Pastrana et al. (2005a) *Virology* 337, 365-72; Roden et al. (2000) (supra)), and confer cross-protection in vivo (Gambhira et al. (2007a) *J Virol* 81, 11585-92).

There is a need to develop immunogens or vaccinogens that exhibit high titer neutralizing antibodies against a broad spectrum of HPV types.

DESCRIPTION

The present inventors demonstrate herein that several L2 peptides (epitopes) from the N-terminus of the L2 protein, e.g., the peptide of about amino acid residues 17-36 of HPV16 L2, or comparable (equivalent) sequences from other types of papillomaviruses (PV), when incorporated into the DE-surface loop of papillomavirus (PV) L1 protein, form recombinant fusion (chimeric) proteins that assemble into VLP; and that these chimeric L1-L2 VLP, when introduced into animals, induce broad-spectrum neutralizing antibody responses to a wide range of mucosal high-risk, low-risk, cutaneous and beta papillomaviruses. The strong and enduring immune responses are considerably higher than that to the linear fusion protein. Without wishing to be bound by any particular mechanism, it is suggested that these strong immune responses result from the display of the epitope on the dense repetitive array of the VLP.

The inventors also suggest that the peptide of amino acid residues 17-36 of HPV16 L2, or comparable (equivalent) sequences from other strains of papillomaviruses (PV), when introduced into other sites of L1, such that the L2 peptide is exposed on the surface of the VLP that is formed, also assemble into chimeric L1-L2 VLP which, when introduced into animals, induce broad-spectrum neutralizing antibody responses to a wide range of mucosal high-risk, low-risk, cutaneous and beta papillomaviruses.

Thus, the particular sequence of the L2 peptide, and/or the L1 site into which the L2 peptide is introduced, are factors which contribute to the induction of strong, broad-spectrum cross-reactivity/neutralization of VLPs of the invention.

In aspects of the invention, one or more of the VLP compositions of the invention are used as an immunogenic or a vaccine composition. In embodiments of the invention, a VLP composition can be used for prophylaxis (e.g., prevention) or treatment of papillomavirus infection and associated disease, and/or can be combined with a pharmaceutical carrier. In certain aspects, a composition is administered to an individual prior to, after, and/or during virus exposure to minimize or prevent virus infection or to reduce the severity of infection and retard or halt progression of the disease, or to prevent transmission of a virus from the infected host to another individual who does not have such a virus infection by vaccination of the infected host or the uninfected individual.

Advantages of the VLP compositions of the invention, and methods of using them to immunize subjects, include that the L2 moiety elicits neutralizing antibody responses against a broad spectrum of HPV, without interfering with the ability of the VLP to induce high-titer anti-L1 antibody levels. The VLP L1 vaccine carrier is well-tolerated and provides long-term immunogenicity (at least 6 years to date). Thus, vaccines based on HPV16 L1 VLP as carrier for L2 epitopes offer the advantage of inducing, with a single construct, both type-restricted antibodies to HPV16 L1, as well as cross-reactive neutralizing anti-L2 antibodies. The broad cross-reactivity reduces the need for screeing tests to determine HPV infection and/or intraepithelial neoplasia, and it reduces the need for making highly multivalent formulations of L1 VLP vaccines to cover all disease causing HPV types, thereby reducing costs. Compositions of the invention provide a low-cost, broadly protective vaccine that is stable, can be produced in a large scale, and can be delivered without needles. The low cost allows for use in developing countries, where 80% of the global cervical cancer burden occurs.

This invention relates, e.g., to a virus-like particle (VLP) composition assembled from (comprising, consisting of) a chimeric polypeptide comprising a papillomavirus (PV) L1 protein, into which is inserted a surface-displayed peptide consisting of the following sequence from a papillomavirus L2 protein:

a)(D/Q/H/E)(L/I)Y(K/P/R/Q/S)(T/S/A/G)CK(Q/I/V/L/A)(A/S/T)(G/N)(T/N)CPPD(I/V)(I/V/Q)(P/N/D)(K/R)(V/I/L) (SEQ ID NO:1), or b) abYcdCKefghCPPDijklm (SEQ ID NO:2), where a=(D/Q/H/E); b=(L/I); c=(K/P/R/Q/S); d=(T/S/A/G); e=(Q/I/V/L/A); f=(A/S/T); g=(G/N); h=(T/N); i=(I/V); j=(I/V/Q); k=(P/N/D); l=(K/R); m=(V/I/L), or c) a sequence that is at least 50, 60, 70, 75, 80, 85, 90 or 95% identical to SEQ ID NO:1 or SEQ ID NO:2.

As used herein, the singular forms "a," "an" and "the" include plural referents unless the context clearly dictates otherwise. Thus, for example, the term "assembled from a chimeric polypeptide," as used above, encompasses more than one chimeric polypeptide.

A consensus sequence for this portion of L2 was first established by one of the present inventors and collaborators in Gambhira et al. (2007b) *J Virol* 81, 13927-31, by aligning the highly conserved sequences in this portion of the L2 protein from a variety of PV species. This original alignment is shown in FIG. 6 herein, and is published in color as FIG. 1A in the Gambhira (2007b) paper, which is incorporated by reference herein, specifically with reference to that figure and the consensus sequence derived therefrom. Subsequently, the present inventors have extended the alignment to include additional varieties of PV species, as is shown in Table 1 below, and have modified the consensus sequences accordingly. The modified consensus sequences are represented by SEQ ID NO:1 and SEQ ID NO:2.

TABLE 1

The HPV16 L2 Epitope RG1 (L2 17-26) is highly conserved among mucosal (high-risk types underlined) and skin type HPV and induces cross-neutralization (√)

| SEQ ID | | | |
|---|---|---|---|
| (NO: 9) | QLYKTCKQAGTCPPDIIPKV | HPV16-RG1 (L2 17-36) | √ |
| (NO: 24) | QLYKTCKQAGTCPPDVIPKV | HPV73 (95%) | |

TABLE 1-continued

The HPV16 L2 Epitope RG1 (L2 17-26) is highly conserved among mucosal (high

TABLE 1-continued

The HPV16 L2 Epitope RG1 (L2 17-26) is highly conserved among mucosal (high-risk types underlined) and skin type HPV and induces cross-neutralization (√)

| SEQ ID | | | |
|---|---|---|---|
| (NO: 12) QLYQTCKAAGTCPSDVIPKI | HPV31 (75%) | √ | |
| (NO: 11) LYRTCKQSGTCPPDVIKV | HPV45 (75%) | √ | |
| (NO: 50) QLYQTCKASGTCPPDVIPKI | HPV32 (75%) | √ | |
| (NO: 51) IYQSCKAAGTCPPDVLNKV | HPV76 (60%) | √ | |
| (NO: 52) IYRGCKASNTCPPDVINKV | HPV38 (55%) | ø | |
| (NO: 3) IYPSCKISNTCPPDIQNKI | HPV1 (50%) | | |
| (NO: 53) NLYAKCQSGNCLPDVKNKV | HPV4 (50%) | | |
| (NO: 21) IYPTCKIAGNCPADIQNKF | CRPV (55%) | ø | |

Figure 6:
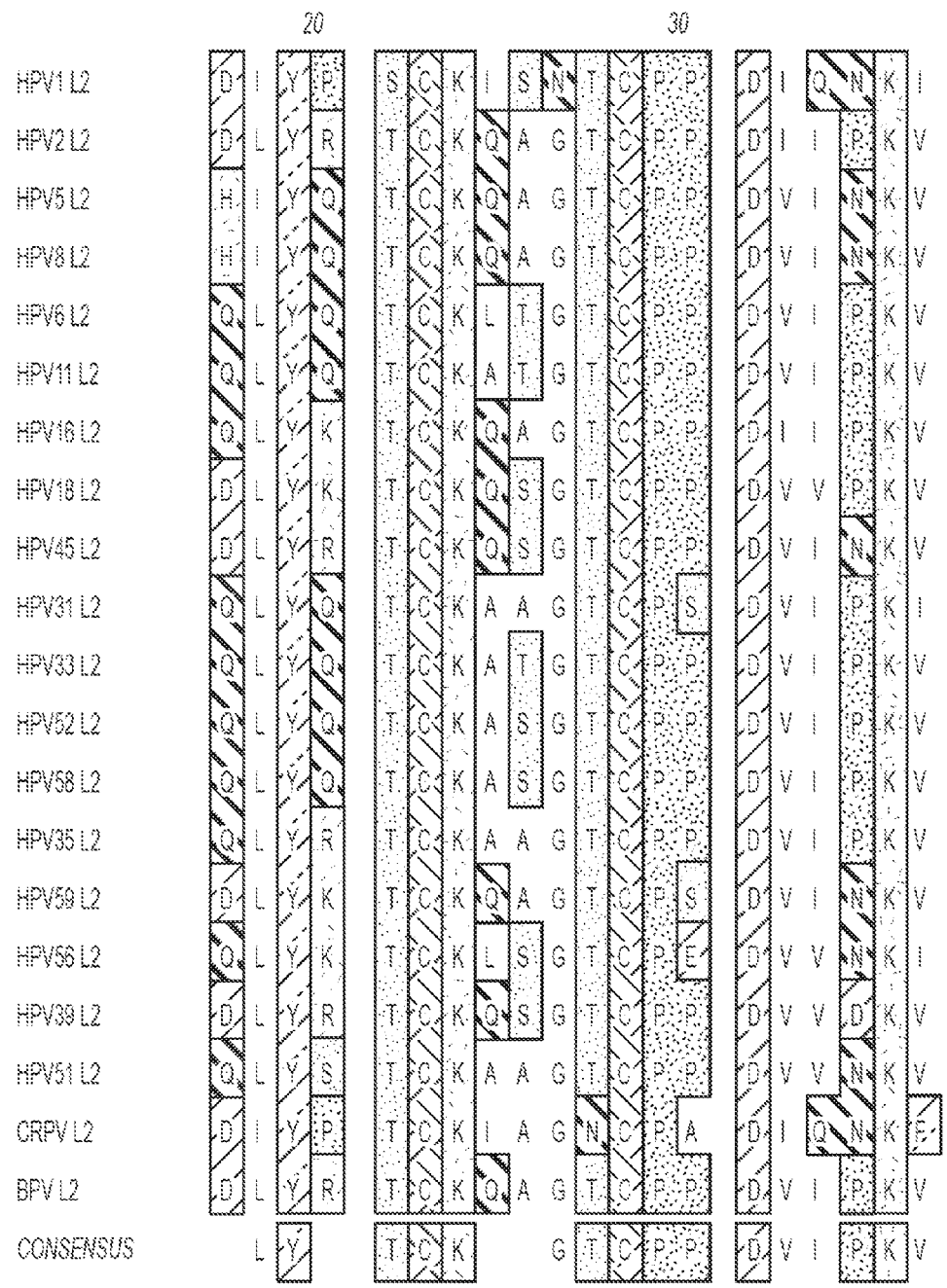
FIG. 6 shows an alignment of sequences of L2 peptides from multiple (not all) human and animal papillomavirus types corresponding to amino acids 17-36 of HPV 16 L2. The sequences in the Table, running from top to bottom, are represented by SEQ ID NOs: 3 to 23.

The L2 sequence can come from any of a variety of PV species. Typical L2 peptides that are suitable include, e.g., those listed in FIG. 6 and in Table 1. In one embodiment of the invention, the L2 peptides are selected from peptides that are shown herein to be cross-reactive (cross-neutralizing). In other embodiments of the invention, the L2 peptides are selected from the mucosal high-risk types (e.g., the most common types that cause cervical cancer: HPV 16, 18, 31, 33, 45, 52 or 58), or from skin type HPV. For example, suitable L2 peptides include:

the peptide from amino acids 17-36 of the HPV16 L2 protein, having the amino acid sequence QLYKTCK-QAGTCPPDIIPKV (SEQ ID NO:9);

the peptide from corresponding amino acids of the HPV18 L2 protein, having the amino acid sequence DLYKTCKQS-GTCPPDVVPKV (SEQ ID NO:10);

the peptide from corresponding amino acids of the BPV1 L2 protein, having the amino acid sequence DLYRTCK-QAGTCPPDVIPKV (SEQ ID NO:22);

the peptide from corresponding amino acids of the HPV38 L2 protein, having the amino acid sequence DIYRGCK-ASNTCPPDVINKV (SEQ ID NO:52);

the peptide from corresponding amino acids of the HPV1 L2 protein, having the amino acid sequence DIYPSCK-ISNTCPPDIQNKI (SEQ ID NO:3); or the peptide from corresponding amino acids of the HPV4 L2 protein, having the amino acid sequence NLYAKCQLS-GNCLPDVKNKV (SEQ ID NO:53).

In embodiments of this aspect of the invention, the L2 peptide is inserted into a loop of the L1 protein such that the L2 peptide will be displayed on the surface of the VLP that forms. For example, the L2 peptide can be inserted into the DE loop or into the helix b4 loop of the L1 protein.

In embodiments of the invention, the L1 protein is from HPV16 (including an HPV16 variant other than the 114K variant, which is exemplified herein), and the L2 peptide is inserted between amino acids 136 and 137 in the DE loop of the L1 protein (the sequence of the HPV16 L1 protein is SEQ ID NO:85); or the L1 protein is from BPV1, and the L2 peptide is inserted between amino acids 133 and 134 in the DE loop of the L1 protein (the sequence of the BPV16 L1 protein is SEQ ID NO:83).

Another aspect of the invention is a virus-like particle (VLP) composition assembled from (comprising, consisting of) a chimeric polypeptide comprising an HPV16 L1 protein, into which is inserted, in the DE loop, a peptide consisting of a) (D/Q/H/E)(L/I)Y(K/P/R/Q/S)(T/S/A/G)CK(Q/I/V/L/A)(A/S/T)(G/N)(T/N)CPPD (I/V)(I/V/Q)(P/N/D)(K/R)(V/I/L)EG (SEQ ID NO:54), or b) abYcdCKefghCPPDijklmEG (SEQ ID NO:55), where a=(D/Q/H/E); b=(L/I); c=(K/P/R/Q/S); d=(T/S/A/G); e=(Q/I/V/L/A); f=(A/S/T); g=(G/N); h=(T/N); i=(I/V); j=(I/V/Q); k=(P/N/D); l=(K/R); m=(V/I/L), or c) a variant of SEQ ID NO:54 or SEQ ID NO:55 which is lacking one amino acid from the N-terminus and/or one or two amino acids from the C-terminus, or d) a sequence that is at least 50, 60, 70, 75, 80, 85, 90 or 95% identical to SEQ ID NO:54 or SEQ ID NO:55, or e) a peptide that reacts with an antiserum (e.g., a rabbit antiserum) to HPV16 L2 (17-36) (SEQ ID NO:9), or with a monoclonal antibody to the peptide HPV16 L2 (17-36) (SEQ ID NO:9).

In embodiments of the invention, the peptide inserted into the DE loop consists of the following sequence from the HPV16 L2 protein (amino acid 17-38): QLYKTCK-QAGTCPPDIIPKVEG (SEQ ID NO:56); or a variant of SEQ ID NO:56 which is lacking one amino acid from the N-terminus and/or one or two amino acids from the C-terminus. Examples of such variant peptides include the HPV16 L2 peptide (17-36) having the sequence QLYKTCKQAGTCP-PDIIPKV (SEQ ID NO:9), and the HPV16 L2 peptide (18-38) having the sequence LYKTCKQAGTCPPDIIPKVEG (SEQ ID NO:57).

In embodiments of this aspect of the invention, in which the L2 peptide is inserted into the DE loop of L1, the L1 protein is from HPV16, and the L2 peptide is inserted between amino acids 136 and 137 in the DE loop of the L1 protein. For reference purposes, the complete amino acid sequence of HPV16 L1 is provided elsewhere herein, as SEQ ID NO:85; or the L1 protein is from BPV1, and the L2 peptide is inserted between amino acids 133 and 134 in the DE loop of the L1 protein. For reference purposes, the complete amino acid sequence of BPV1 L1 is provided elsewhere herein, as SEQ ID NO:83.

For any of the VLP compositions of the invention, a variety of combinations of L1 and L2 proteins/peptides can be used. For example, the L1 and L2 proteins can be from a human papilloma virus (HPV);

the L1 protein can be from a BPV, such as BPV1, the very closely related BPV2, or another one of the at least 10 BPV types that have been identified (e.g., BPV4); or the L1 protein and/or the L2 protein can be from a PV other than an HPV.

In aspects of the invention, the L1 protein is a variant of the L1 exemplified herein. Some such variants are discussed elsewhere herein. These include, e.g., chimeras of L1 genes derived from different HPV types as the scaffold, as well as truncated versions of L1 that assemble into VLP or capsomers.

In aspects of the invention, a VLP of the invention is an immunogenic composition, which, e.g., induces a humoral or a cellular immune response, antigen-specific or innate. A VLP of the invention can be immunogenic against 1, 2, 3, 4, 5, or more of mucosal high-risk types (e.g., HPV 16, 18, 31, 33, 45, 52, 58, 68, or 76), mucosal low-risk types (e.g. HPV 6 and 11), HPV13, 32 causing Heck's disease (focal epithelial hyperplasia of othe oral mucosa), cutaneous low risk types (skin-tropic types) causing skin warts (e.g., HPV1, 2, 3, 4, 7, 10, 27, 57, etc.) and/or cutaneous beta-types (e.g. beta-type HPV5, 8, 9, 12, 14, 15, 38, etc.) of papillomaviruses, or animal papillomavirus types. With regard to the nomenclature of PV, all beta PV are cutaneous types. However, cutaneous types are usually referred to as those that induce common, palmar, plantar, or plane skin warts (these are found in the alpa, gamma, mu, nu genus). The beta types generally only induce skin warts (or skin cancer) in EV patients or immunosuppressed patients.

Another aspect of the invention is a VLP or capsomere composition of the invention that further comprises an adjuvant, or a vaccine comprising a VLP composition of the invention and an adjuvant. A vaccine of the invention can be effective against human papillomaviruses (e.g., against mucosal high-risk, low-risk, cutaneous and beta (e.g. beta-type HPV 5) papillomaviruses). A vaccine of the invention can be formulated in a variety of manners, including a lyophilized or powdered form, a formulation for administration by inhalation, ingestion (e.g., as a pill), in a viral or bacterial vector, or as a component of a sexual lubricant. One mode of administration is similar to that of the currently existing HPV vaccines, for i.m. inoculation with adjuvant (e.g., alum or alum-MPL). For administration in developing countries, which may lack adequate refrigeration, formulations for lyophilized, inhalation, ingestion, or viral or bacterial vectors may be more suitable.

Another aspect of the invention is a chimeric polypeptide, comprising a papillomavirus (PV) L1 protein (e.g., an HPV16 L1 protein), into which is inserted a surface-displayed peptide consisting of one of the following sequences from a papillomavirus L2 protein:

a) (D/Q/H/E)(L/I)Y(K/P/R/Q/S)(T/S/A/G)CK(Q/I/V/L/A)(A/S/T)(G/N)(T/N)CPPD (I/V)(I/V/Q)(P/N/D)(K/R)(V/I/L) (SEQ ID NO:1), or b) abYcdCKefghCPPDijklm (SEQ ID NO:2), where a=(D/Q/H/E); b=(L/I); c=(K/P/R/Q/S); d=(T/S/A/G); e=(Q/I/V/L/A); f=(A/S/T); g=(G/N); h=(T/N); i=(I/V); j=(I/V/Q); k=(P/N/D); l=(K/R); m=(V/I/L), or c) a sequence that is at least 50, 60, 70, 75, 80, 85, 90 or 95% identical to SEQ ID NO:1 or SEQ ID NO:2, or a chimeric polypeptide assembled from (comprising, consisting of) a papillomavirus (PV) L1 protein, into which is inserted, in the DE loop, a peptide consisting of d) (D/Q/H/E)(L/I)Y(K/P/R/Q/S)(T/S/A/G)CK(Q/I/V/L/A)(A/S/T)(G/N)(T/N)CPPD (I/V)(I/V/Q)(P/N/D)(K/R)(V/I/L)EG (SEQ ID NO:54), or e) abYcdCKefghCPPDijklmEG (SEQ ID NO:55), where a=(D/Q/H/E); b=(L/I); c=(K/P/R/Q/S); d=(T/S/A/G); e=(Q/I/V/L/A); f=(A/S/T); g=(G/N); h=(T/N); i=(I/V); j=(I/V/Q); k=(P/N/D); l=(K/R); m=(V/I/L), or f) a variant of SEQ ID NO:54 or SEQ ID NO:55 which is lacking one amino acid from the N-terminus and/or one or two amino acids from the C-terminus, or g) a sequence that is at least 50, 60, 70, 75, 80, 85, 90 or 95% identical to SEQ ID NO:54 or SEQ ID NO:55, or h) a peptide that reacts with an antiserum (e.g., a rabbit antiserum) to HPV16 L2 (17-36) (SEQ ID NO:9), or with a monoclonal antibody to the peptide HPV16 L2 (17-36) (SEQ ID NO:9).

Other aspects of the invention are a nucleic acid (e.g., a DNA, an RNA, or other forms of nucleic acid) that encodes a polypeptide of the invention; an expression vector (e.g., derived from viral or bacterial regulatory sequences) comprising such a nucleic acid, which is operably linked to an expression control sequence; and a host cell comprising such a polypeptide, nucleic acid or expression vector.

Another aspect of the invention is a method for making a VLP or capsomer composition, comprising incubating a chimeric polypeptide as above under suitable conditions for self-assembly.

Another aspect of the invention is a method for immunizing or vaccinating a subject against a PV (e.g., HPV), comprising administering to the subject an effective amount of a VLP or capsomere composition of the invention.

Another aspect of the invention is a method for inducing an immune response against HPV in a subject, comprising administering to the subject an effective amount of a VLP or capsomere composition (e.g., an immunogenic composition or a vaccine) of the invention. The immune response can be a humoral or a cellular immune response, antigen-specific or innate.

Another aspect of the invention is a method for treating a PV infection in a subject having a PV infection or at risk of being exposed to PV, comprising administering to the subject an effective amount of a VLP or a capsomer composition of the invention (e.g., an immunogenic composition or a vaccine).

Another aspect of the invention is a method for preventing cervical, anogenital, or oropharyngeal cancer, or a precancer, in a subject, comprising administering to the subject an effective amount of a VLP composition of the invention. "Precancer," as used herein, refers to precursors of cervical and other anogenital cancers, such as high-grade and low-grade intraepithelial lesion, HSIL, LSIL (or CIN, VIN, AIN etc., with regard to the anatomical regions cervix, vulva and anal, respectively). These conditions are already known to be prevented by current L1 VLP vaccines, and would be expected to be prevented by VLP compositions of the present invention.

Another aspect of the invention is a kit comprising a VLP or capsomere composition of the invention, or comprising antibodies that bind a VLP composition of the invention.

Another aspect of the invention is a prophylactic or therapeutic antibody or immune serum generated by vaccination with a VLP composition of the invention, which can be administered to a healthy or diseased subject, respectively, to prevent or treat a PV infection.

Another aspect of the invention is a capsomere composition, comprising an L1/L2 chimeric polypeptide of the invention that has self-assembled into a capsomere (capsomer, pentameric L1 structural subunit) rather than into a VLP.

Methods for generating such capsomers are conventional in the art. See, e.g., *J Virol* 1998 January; 72(1):32-41; *J Virol* 1998 March; 72(3):2160-7; Thones et al. (2007) *Virology* 369, 375-388; or Bishop et al. (2007), The *Journal of Bioogical Chemistry* 282, 31803-31811, all of which are incorporated by reference, particularly for their descriptions of methods to generate capsomers. One way of generating capsomeres is to truncate a L1 protein, or to use a mutated L1 gene (e.g., carrying the mutations C175A abd C428A), which inhibit its ability to form a VLP. See, e.g., *J Mol Bio* 2001 Mar. 16; 307(1):173-82; *J Virol* 1997 April; 71(4):2988-95, both of which are incorporated by reference, particularly with regard to such methods.

Another aspect of the invention is a method for inducing an immunological reaction to (protecting against infection with) alpha-skin type HPVs (e.g., HPV2, 3) in a subject, comprising administering to the subject an effective amount of a VLP composition of the invention. HPV2 is closely related to the types HPV27 and 57, which together with HPV1 are the types most commonly found in skin warts. HPV3, and the closely related type HPV10, are low risk cutaneous alpha types which are commonly found in flat skin warts, both in immuncompent patients, or in immunocompromised (e.g. renal transplant) or EV patients.

A chimeric "virus-like particle (VLP)" of the invention, as used herein, refers to an empty viral capsid which is composed of papillomavirus L1 protein molecules, into which are inserted a peptide of the minor viral capsid, L2. The inserted peptides are inserted into a suitable region of the L1 protein so that they are displayed on the surface of the VLP. In one embodiment of the invention, the L2 peptide is inserted in the DE loop of L1, e.g. between amino acids 133 and 134 of BPV1, between amino acids 136 and 137 of HPV16 L1, or between equivalent sites of L1 molecules from other papillomaviruses. The inserted peptide comprises one or more epitopes (e.g., neutralizing epitopes) that are cross-reactive with a broad spectrum of PV types. In one embodiment, the L2 peptide comprises amino acids 17-36 of the HPV16 L2 protein, or an equivalent sequence of amino acids from another papillomavirus. The chimeric L1 proteins assemble spontaneously into VLP and resemble native virions in both structure and immunogenicity, yet lack nucleic acid and thus are non-oncogenic and non-infectious.

The L1 protein into which an L2 peptide is inserted can be from any of a variety of types (strains) of papillomavirus (PV). For example, VLPs can be used to protect any of a variety of animals against PV infection, including, e.g., cattle and canines; for such VLPs, the L1 can be from PV strains that are known to infect those animals, e.g. BPV1, BPV2, BPV4, BPV6, or canine oral PV (COPV). In one embodiment, the VLPs are used to protect humans against HPV infection; for such VLPs, the L1 can be from any type of HPV (e.g, HPV 16, 18, 45, 6, 11, 1, 2, 4, 5 or 8.) Alternativley, BPV could be a suitable vaccine carrier for use in humans, particularly in patients who have had a prior exposure to the HPV strain typically used to form the VLP composition. VLP in which the L1 protein is derived from BPV and HPV 16 are exemplified herein; constructs comprising other sources of the L1 protein will be evident to a skilled worker.

In the Examples herein, the L1 protein is essentially the wild type version, except for the insertion of the L2 peptide. However, a skilled worker will recognize that variants of the L1 protein can also be used, provided that the protein can tolerate the insertion of a suitable L2 peptide, without losing its antigenicity, and that it can assemble into a VLP, or at least a pentamer (capsomer). Several examples of such variants have been described. For example, one can use a truncated L1, lacking up to 10 amino acids from its N-terminus or lacking up to 30 amino acids from its C-terminus. (See, e.g., *J Mol Bio* 2001 Mar. 16; 307(1):173-82, or Bishoop et al. (2007) *The Journal of Biological Chemistry* 282, 31803-31811, both of which are incorporated by reference for their disclosure of making and using such truncated L1 proteins). In another embodiment, a small fusion to a peptide of about 60 amino acids can be used. (See, e.g., *Virology* 1997 Jul. 21; 234(1):93-111, which is incorporated by reference for its disclosure of such fusion peptides.) In another embodiment, hybrid L1 molecules can be used, in which one portion of the molecule from a first strain of PV is swapped into an L1 molecule from a second strain of PV. For example, certain functional portions of the L1 molecule, such as externally exposed "loops" of the protein, can be swapped between molecules from different strains of PV. For examples of such hybrid L1 proteins, see, e.g., *Virology* 2001 Dec. 20: 291(2): 324-34 or Oroczo et al. (2005) *J Virol* 79, 9503-9514, both of which are incorporated by reference for their disclosues of such hybrid L1 proteins. Other types of variants will be evident to a skilled worker. See, e.g., *J Virol* 2006 May; 80(10): 4664-72; White et al. (1999) *J Virology* 73, 4882-4889; or Roden et al. (1997) *J Virol* 71, 6247-52, all of which are incorporated by reference herein for their disclosures of other types of suitable variants of L1.

An L2 peptide can be engineered into an L1 protein at any of a variety of sites of the L1 protein, provided that the insert is displayed on the surface of the VLP and that the insertion does not interfere with the antigenicity of the L1 protein or the ability of the protein to assemble into a VLP. Crystallization of L1 HPV16 VLP has revealed the atomic structure of the viral capsid, in particular the hypervariable surface loops that contain the immunodominant and conformation-dependent epitopes that are recognized by neutralizing antibodies and determine the viral serotype (Chen et al. (2000) *Molecular Cell* 5, 557-567). Accordingly, suitable sites for insertion of an L2 peptide into the L1 protein will be evident to a skilled worker. These include, e.g., the helix b4 loop (e.g. between amino acids 430 and 433 of HPV16 L1). In one embodiment of the invention, the L2 peptide is inserted into the DE loop (e.g. between amino acids 133/134 of BPV, or the equivalent amino acids 136/137 of HPV, which is exemplified herein. Equivalent insertion sites of other PVs can also be used.

Any of a variety of L2 peptides can be inserted into an L1 protein to form a VLP of the invention. In one embodiment, the peptide extends from amino acid 17-36 of HPV16 L2, and has the sequence QLYKTCKQAGTCPPDIIPKV (SEQ ID NO:9). A skilled worker will recognize that this sequence is highly conserved among a variety of strains of PV, and that comparable peptides can be selected from the equivalent region of any of a variety of L2 proteins to be inserted into an L1 protein.

For example, the HPV L2 epitope can comprise equivalent sequences from a papillomavirus within the a genus, or the genera β, γ, δ, ε, ζ, η, θ, ι, κ, λ, μ, ν, ξ, ο, π (See, e.g., de Villiers et al. (2004) *Virology* 324, 17-27); and/or from human papillomaviruses: HPV1, HPV2, HPV3, HPV4, HPV5, HPV6, HPV7, HPV8, HPV9, HPV10, HPV11, HPV12, HPV13, HPV14, HPV15, HPV16, HPV17, HPV18, HPV19, HPV20, HPV21, HPV22, HPV23, HPV24, HPV25, HPV26, HPV27, HPV28, HPV29, HPV30, HPV31, HPV32, HPV33, HPV34, HPV35, HPV36, HPV37, HPV38, HPV39, HPV40, HPV41, HPV42, HPV43, HPV44, HPV45, HPV46, HPV47, HPV48, HPV49, HPV50, HPV51, HPV52, HPV53, HPV54, HPV55, HPV56, HPV57, HPV58, HPV59, HPV60, HPV61, HPV62, HPV63, HPV64, HPV65, HPV66, HPV67, HPV68, HPV69, HPV70, HPV71, HPV72, HPV73, HPV74, HPV75, HPV76, HPV77, HPV78, HPV79, HPV80, HPV81, HPV82, HPV83, HPV84, HPV85, HPV86, HPV87, HPV88, HPV89, HPV90, HPV91, HPV92, HPV93, HPV94, HPV95, HPV96, HPV97, HPV98, HPV99, HPV100 through HPV 127; and/or animal papillomaviruses: bovine papillomavirus type 1 (BPV1), bovine papillomavirus type 2 (BPV2), bovine papillomavirus type 4 (BPV4), cottontail rabbit papillomavirus (CRPV), deer papillomavirus (DPV), European elk papillomavirus (EEPV), canine oral papillomavirus (COPY), Rhesus monkey papillomavirus (RhPV) and rabbit oral papillomavirus (ROPV).

An HPV antigen or epitope or peptide of the invention can comprise a consecutive amino acid sequence from amino acid x to amino acid y of HPV16 L2 polypeptide SEQ ID NO:81, wherein in x is 12, 13, 14, 15, 16, 17, 18, 19, 20, 21 or 22, and y is amino acid 26, 27, 28, 29, 30, 31, 32, 33, 34, 35, 36, 37, 38, 39, 40, 41, 42, or 43. An HPV antigen or epitope or peptide of the invention can comprise about 20 amino acids, e.g., 15, 16, 17, 18, 19, 20, 21, 22, 23, 24 or 25 consecutive amino acids. In certain embodiments, the L2 peptide is an HPV16 epitope (SEQ ID NO:9), an HPV18 epitope (SEQ ID NO:10), or an HPV45 epitope (SEQ ID NO:11). In further aspects, the L2 peptide comprises amino acids 17-36 of SEQ ID NO:81 (HPV16 L2 17-36 (SEQ ID NO:9)). While this fragment is designated 17-36 based on HPV16 the actual amino acid position from other HPV types may differ but are easily identified by alignment with the HPV16 sequences disclosed herein ("equivalent" or "comparable" sequences). In certain aspects, the L2 peptide is at least or more than 50%, 60%, 70%, 80%, 85%, 90%, 91%, 92%, 93%, 94%, 95%, 96%, 97%, 98%, or 99% identical to SEQ ID NO:9. In certain embodiments the L2 peptide comprises the consensus amino acid sequence

```
                                          (SEQ ID NO: 1)
(D/Q/H/E)(L/I)Y(K/P/R/Q/S)(T/S/A/G)CK(Q/I/V/L/A)
(A/S/T)(G/N)(T/N)CPPD(I/V)(I/V/Q)(P/N/D)(K/R)
(V/I/L),
or
                                          (SEQ ID NO: 2)
abYcdCKefghCPPDijklm,
where a = (D/Q/H/E); b = (L/I); c = (K/P/R/Q/S);
d = (T/S/A/G); e = (Q/I/V/L/A); f = (A/S/T);
g = (G/N); h = (T/N); i = (I/V); j = (I/V/Q);
k = (P/N/D); l = (K/R); m = (V/I/L).
```

As used herein, the term "antigen" is a molecule capable of being bound by an antibody or T-cell receptor. An antigen is additionally capable of inducing a humoral immune response and/or cellular immune response leading to the stimulation of B- and/or T-lymphocytes. The structural aspect of an antigen that gives rise to a biological response is referred to herein as an "antigenic determinant" or "epitope" and are synonymous. B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant or epitope need not be a contiguous/consecutive sequence or segment of protein and may include various sequences that are not immediately adjacent to one another.

With regard to a particular amino acid sequence, an "epitope" is a set of amino acid residues which is involved in recognition by a particular immunoglobulin, or in the context of T-cells, those residues necessary for recognition by T-cell receptor proteins and/or Major Histocompatibility Complex (MHC) receptors. The amino acid residues of an epitope need not be contiguous/consecutive. In an immune system setting, in vivo or in vitro, an epitope is the collective features of a molecule, such as primary, secondary and tertiary peptide structure, and charge, that together form a site recognized by an immunoglobulin, T-cell receptor or HLA molecule. Throughout this disclosure, "epitope" and "peptide" are often used interchangeably.

As used herein, "B-cell epitope" or "target epitope" (e.g., HPV L2), refers to a feature of a peptide or protein that is recognized by a B-cell receptor in the immunogenic response to the peptide comprising that antigen (e.g., an HPV L2 epitope (immunogen or target epitope)).

As used herein "helper T-cell epitope" or "Th epitope" means a feature of a peptide or protein that is recognized by a T-cell receptor in the initiation of an immunologic response to the peptide comprising that antigen. Recognition of a T-cell epitope by a T-cell is generally believed to be via a mechanism wherein T-cells recognize peptide fragments of antigens which are bound to class I or class II Major Histocompatibility Complex (MHC) molecules expressed on antigen-presenting cells. In some embodiments of the present invention, the epitopes or epitopic fragments identified as described herein find use in the detection of antigen presenting cells having MHC molecules capable of binding and displaying the epitopes or fragments.

As used herein, "HPV" and "human papillomavirus" refer to the members of the family Papillomavirus that are capable of infecting humans. There are two major groups of HPVs defined by their tropism (genital/mucosal and cutaneous groups), each of which contains multiple virus "types" or "strains" (e.g., HPV 16, HPV 18, HPV 31, HPV 32, etc.). Of particular interest in the present invention are the HPV types that are associated with genital infection and malignancy, as well as those that produce benign papillomas, both at mucosa and skin, resulting in morbidity to the patient.

The term "vaccine" refers to a formulation which contains 1, 2, 3, 4, 5, or more VLP compositions of the present invention. The VLP compositions will typically be in a form that is capable of being administered to a subject and induces a protective or therapeutic immune response sufficient to induce immunity to prevent and/or ameliorate an infection and/or to reduce at least one symptom of an infection and/or to enhance the efficacy of another anti-HPV therapy or prophylactic. Typically, a vaccine comprises a conventional saline or buffered aqueous solution medium in which the composition of the present invention is suspended or dissolved, although administration of dry powder, for example by inhalation, and even formulation with an additional adjuvant, such as alum, is also contemplated. The composition of the present invention can be used conveniently to prevent, ameliorate, or otherwise treat an infection. Upon introduction into a host, an immunogenic composition of the invention (e.g., a vaccine) is able to provoke an immune response including, but not limited to, the production of antibodies and/or cytokines and/or the activation of cytotoxic T cells, antigen presenting cells, helper T cells, dendritic cells and/or other cellular responses. Typically, such a response will be cross reactive between various types of papillomavirus, including, but not limited to 2, 3, 4, 5, 6, 7, 8, 9, 10 or more of the HPV types described herein. Particular cross reactive HPV types are discussed elsewhere herein.

As used herein, "prophylactic" and "preventive" vaccines, antibodies or immune sera are vaccines, antibodies or immune sera that are designed and administered to prevent infection, disease, and/or any related sequela(e) caused by or associated with a pathogenic organism, particularly HPV.

As used herein, "therapeutic" vaccines are vaccines that are designed and administered to patients already infected with a pathogenic organism such as at least one HPV strain. Therapeutic vaccines (e.g., therapeutic HPV vaccines) are used to prevent and/or treat the development of benign or malignant tumors in these infected individuals.

The terms "inhibiting," "reducing," or "prevention," or any variation of these terms, when used in the claims and/or the specification includes any measurable decrease or complete inhibition to achieve a desired result, such as inhibiting, reducing, or preventing viral infection, viral spread, viral growth, or viral transmission.

Throughout this application, the term "about" is used to indicate that a value includes the standard deviation of error for the device or method being employed to determine the value.

It is contemplated that one or more members of a list provided herein may be specifically excluded from or included in a claimed invention.

A "subject," as used herein, includes any animal that has been infected with, or is at risk of being infected with, a papillomavirus. Suitable subjects (patients) include laboratory animals (such as mouse, rat, rabbit, guinea pig or pig), farm animals (such as cattle), sporting animals (such as dogs or horses) and domestic animals or pets (such as a horse, dog or cat). Non-human primates and human patients are included.

The terms "protein," "polypeptide," and "peptide," as used herein, are not restricted to any particular number of amino acids; these terms are sometimes used interchangeably herein. The properties and amino acid sequences of the proteins of the invention, and of the nucleic acids encoding them, are well-known and can be determined routinely, as well as downloaded from various known databases. See, e.g., the NCBI GenBank databases. Some sequences are provided herein. This information is accurate as of the date of filing of this application. However, some sequence information is routinely updated (e.g. to correct mistakes in the previous entries), so updated (corrected) information about the proteins and nucleic acids encoding them is included in this application. Information provided in the sequence databases discussed herein is incorporated by reference in the present application.

The chimeric proteins discussed herein are sometimes referred to herein as "proteins of the invention."

One aspect of the invention is a method for making a VLP (or the polypeptide component thereof) of the invention. In one embodiment of the invention, HPV epitopes are synthesized using conventional methods as modified for the particular amino acid sequences. Such techniques include, e.g., methods well known to those skilled in the art of peptide synthesis, e.g., solution phase synthesis [see Finn et al. in *Proteins*, 3$^{rd}$ Ed., Neurath and Hill (Eds), Academic Press, NY, 2, 105-253, 1976], or solid phase synthesis [see Barany et al. In: *The Peptides*, Gross and Meienhofer (Eds.), Academic Press, NY, 3-284, 1979], or stepwise solid phase synthesis as reported by Merrifield et al. (1963) *J. Am. Chem. Soc.* 85, 2149-2154], the contents of each of which are incorporated herein by reference. Other references to peptide synthesis techniques include peptides synthesized by the Fmoc-polyamide mode of solid-phase peptide synthesis as disclosed by Lu et al. (1981) *J. Org. Chem.* 46, 3433, peptides synthesized using an Fmoc/tBu procedure (Atherton et al. In: *Solid Phase Peptide Synthesis: A Practical Approach*, IRL Press, Oxford, 1989). Fmoc amino acids can be obtained from various vendors, e.g., Chem-Impex International (Wood Dale, Ill., USA), Merck Biosciences (Nottingham, UK), and Bachem UK Ltd. (St. Helens, UK).

Alternatively, a polypeptide of the invention can be prepared recombinantly. The present invention provides recombinant cloning and expression vectors containing DNA, as well as host cell containing the recombinant vectors. Expression vectors comprising DNA may be used to prepare the polypeptides or polypeptide fragments of the invention encoded by a DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell. Polypeptides of the invention can include various leader sequences that direct trafficking or assist in purification.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

Suitable host cells for expression of polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al In: *Cloning Vectors: A Laboratory Manual*, Elsevier, N.Y., 1985. Cell-free translation systems could also be employed to produce polypeptides using RNAs derived from DNA constructs disclosed herein. In general, molecular biology methods referred to herein are well-known in the art and are described, e.g., in Sambrook et al., Molecular Cloning: A Laboratory Manual, current edition, Cold Spring Harbor Laboratory, Cold Spring Harbor, N.Y., and Ausubel et al., Current Protocols in Molecular Biology, John Wiley & sons, New York, N.Y.

Methods for allowing polypeptides to assemble into VLPs are well-known and conventional, as are methods for purifying them for use in subjects. For "suitable conditions for self-assembly," see, e.g., the methods described in the Examples herein, or in Kirnbauer et al. (1993) *J Virol* 67, 6929-6936; Volpers et al. (1994) *Virology* 200, 504-512; or J Mol Biol 2001 Mar. 16; 307(1):173-82, all of which are incorporated by reference for the descriptions of such methods.

The methods of the present invention include prevention and/or treatment for a disease or condition caused by or related to papillomavirus infection (e.g., HPV infection). An immunogenic HPV peptide and/or antibody that binds the same, can be given to induce or provide a protective and/or therapeutic response in a subject infected with or suspected of having been exposed to or at risk of becoming infected with HPV. Methods may be employed with respect to individuals who have tested positive for exposure to HPV or who are deemed to be at risk for infection based on possible exposure.

In some embodiments, the treatment is administered in the presence of adjuvants or carriers or other antigens, either HPV antigens or antigens from other pathogens. Furthermore, in some examples, treatment comprises administration of other agents commonly used against viral infection, such as one or more anti-virals.

The immunogenicity of VLP compositions can be enhanced by the use of additional non-specific stimulators of the immune response, known as adjuvants. Suitable adjuvants include all acceptable immunostimulatory compounds, such as cytokines, toxins, or synthetic compositions such as alum.

A number of adjuvants can be used to enhance an antibody response against a VLP described herein. Adjuvants can be used to (1) trap the antigen in the body to cause a slow release; (2) attract cells involved in the immune response to the site of administration; (3) induce proliferation or activation of immune system cells; or (4) improve the spread of the antigen throughout the subject's body.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GM-CSF, BCG, aluminum salts, such as aluminum hydroxide or other aluminum compound, MDP compounds, such as thur-MDP and nor-MDP, CGP (MTP-PE), lipid A, and monophosphoryl lipid A (MPL), or inactivated microbial agents. RIBI, which contains three components extracted from bacteria, MPL, trehalose dimycolate (TDM), and cell wall skeleton (CWS) in a 2% squalene/Tween 80 emulsion. MHC antigens may even be used. Others adjuvants or methods are exemplified in U.S. Pat. Nos. 6,814,971, 5,084,269, 6,656,462, each of which is incorporated herein by reference).

Various methods of achieving adjuvant affect for the vaccine includes use of agents such as aluminum hydroxide or phosphate (alum), commonly used as about 0.05 to about 0.1% solution in phosphate buffered saline, admixture with synthetic polymers of sugars (CARBOPOL®) used as an about 0.25% solution, aggregation of a protein in the vaccine by heat treatment with temperatures ranging between about 70° to about 101° C. for a 30-second to 2-minute period, respectively. Aggregation by reactivating with pepsin-treated (Fab) antibodies to albumin; mixture with bacterial cells (e.g., *C. parvum*), endotoxins or lipopolysaccharide components of Gram-negative bacteria; emulsion in physiologically acceptable oil vehicles (e.g., mannide mono-oleate (Aracel A)); or emulsion with a 20% solution of a perfluorocarbon (FLUOSOL-DA®) used as a block substitute may also be employed to produce an adjuvant effect. A typical adjuvant is complete Freund's adjuvant (containing killed *Mycobacterium tuberculosis*), incomplete Freund's adjuvants, and aluminum hydroxide.

For administration to humans, a variety of suitable adjuvants will be evident to a skilled worker. These include, e.g., Alum-MPL as adjuvant, or the comparable formulation, ASO4, which is used in the approved HPV L1 vaccine Cervarix®, AS03, AS02, MF59, montanide, saponin-based adjuvants such as GPI-0100, CpG-based adjuvants, or imiquimod. In embodiments of the invention, an adjuvant is physically coupled to the VLP, or encapsulated by the VLP, rather than simply mixed with them.

In addition to adjuvants, it may be desirable to co-administer biologic response modifiers (BRM) to enhance immune responses. BRMs have been shown to upregulate T cell immunity or downregulate suppresser cell activity. Such BRMs include, but are not limited to, Cimetidine (CIM; 1200 mg/d) (Smith/Kline, PA); or low-dose Cyclophosphamide (CYP; 300 mg/m$^2$) (Johnson/Mead, NJ) and cytokines such as γ-interferon, IL-2, or IL-12 or genes encoding proteins involved in immune helper functions, such as B-7. In embodiments of the invention, these genes are encapsulated by the VLP to facilitate their delivery into a subject.

The manner of application may be varied widely. Any of the conventional methods for administration of a vaccine are applicable. These are believed to include oral application on a solid physiologically acceptable base or in a physiologically acceptable dispersion, parenterally by injection, inhalation of a powder, via transcutaneous patch, via vaginal instillation and the like. The dosage of the vaccine will depend on the route of administration and will vary according to the size and health of the subject.

The preparation of vaccines that contain polypeptide or peptide sequence(s) as active ingredients is generally well understood in the art, as exemplified by U.S. Pat. Nos. 4,608,251; 4,601,903; 4,599,231; 4,599,230; 4,596,792; and 4,578,770, all of which are incorporated herein by reference. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain amounts of auxiliary substances such as wetting or emulsifying agents, pH buffering agents, or adjuvants that enhance the effectiveness of the vaccines. In specific embodiments, vaccines are formulated with a combination of substances, as described in U.S. Pat. Nos. 6,793,923 and 6,733,754, which are incorporated herein by reference.

Vaccines may be administered by inhalation. In certain embodiments a vaccine can be administered as an aerosol. As used herein the term "aerosol" or "aerosolized composition" refers to a suspension of solid or liquid particles in a gas. The terms may be used generally to refer to a composition that has been vaporized, nebulized, or otherwise converted from a solid or liquid form to an inhalable form including suspended solid or liquid drug particles. Such aerosols can be used to deliver a vaccine via the respiratory system. As used herein, "respiratory system" refers to the system of organs in the body responsible for the intake of oxygen and the expiration of carbon dioxide. The system generally includes all the air passages from the nose to the pulmonary alveoli. In mammals it is generally considered to include the lungs, bronchi, bronchioles, trachea, nasal passages, and diaphragm. For purposes of the present disclosure, delivery of a vaccine to the respiratory system indicates that a drug is delivered to one or more of the air passages of the respiratory system, in particular to the lungs.

Additional formulations which are suitable for other modes of administration include suppositories (for anal or vaginal application) and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

The VLP compositions may be formulated into a vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In many instances, it will be desirable to have multiple administrations of the vaccine, usually at most, at least, or not exceeding 1, 2, 3, 4, 5, 6, 7, 8, 9, 10, 11, 12, 13, 14, 15, or more vaccinations including all ranges there between. The vaccinations will normally be at 1, 2, 3, 4, 5, 6, to 5, 6, 7, 8, 9, 10, 11, to 12 week/month/year intervals, including all values and ranges there between, more usually from three to five week intervals. Typically, periodic boosters at intervals of 1-15 years, usually ten years, will be desirable to maintain protective levels of the antibodies. The course of the immunization may be followed by assays for antibodies against the antigens, as described supra, U.S. Pat. Nos. 3,791,932; 4,174,384 and 3,949,064, which are illustrative of these types of assays.

The compositions and related methods of the present invention, particularly administration of a VLP comprising an HPV L2 epitope to a patient/subject, may also be used in combination with the administration of traditional HPV screening and/or other vaccines, including, e.g., antibodies or antibody fragments, Pap smears, PCR, Southern blotting, administering CERVARIX™, GARDASIL™, vaccines for HPV or other infectious agents, ablative therapy of HPV lesions, immunomodulatory therapies for HPV lesions (e.g. Aldara™) or the like.

In some embodiments, pharmaceutical compositions are administered to a subject. Different aspects of the present invention involve administering an effective amount of a composition to a subject. In some embodiments of the present invention, a VLP comprising an HPV L2 epitope is administered to the patient to protect against or treat infection by one or more HPV pathogens. Such compositions will generally be dissolved or dispersed in a pharmaceutically acceptable carrier or aqueous medium.

As used herein, the term "pharmaceutically acceptable" or "pharmacologically acceptable" refer to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent. Pharmaceutically acceptable carrier includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

The active compounds of the present invention can be formulated for parenteral administration, e.g., formulated for injection via the intravenous, intramuscular, sub-cutaneous, or even intraperitoneal routes. In addition to the compounds formulated for aerosol or parenteral administration, such as those for intravenous or intramuscular injection, other pharmaceutically acceptable forms include, e.g., tablets or other solids for oral administration; time release capsules.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The VLP compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions according to the present invention will typically be via any common route. This includes, but is not limited to oral, nasal, or buccal administration. Alternatively, administration may be by orthotopic, intradermal, subcutaneous, intramuscular, intraperitoneal, respiratory, or intravenous administration. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion (see for example, Remington's Pharmaceutical Sciences, 1990). Some variation in dosage will necessarily occur depending on the condition of the subject. The person responsible for administration will, in any event, determine the appropriate dose for the individual subject.

An effective amount of therapeutic or prophylactic composition is determined based on the intended goal. An "effective amount" is an amount that is effective to bring about a desired outcome (e.g., the induction of a measurable amount of an immune response, the immunization of a subject, etc.). The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

In one embodiment of the invention, VLPs are administered to subjects by administering an effective amount of a recombinant attenuated bacterium (such as a *salmonella bacterium*) which encodes a chimeric polypeptide of the invention. The VLPs are then produced by the gut in vivo, where the bacteria replicate. For guidance for carrying out methods using such bacterial vectors, see, e.g., Nardelli-Haefliger (2007) *Clin Vaccine Immunol* 14, 1285-1295, which is incorporated by reference specifically for such disclosure. Methods for generating recombinant constructs that can be expressed in bacteria (bacterial vectors) are conventional; some typical methods are described elsewhere herein. Lyophilized bacteria can be easily shipped to developing countries, where they can then be resuspended and administered to subjects. Such a mode of administration is advantageous in a country to lacks refrigeration capabilities that might be required for other formulations of VLPs. In another embodiment, VLPs are administered in an attenuated virus, such as an attenuated Adenovirus, or other viral vectors which are well-known to those of skill in the art. Methods for producing suitable recombinant nucleic acids that can be expressed in a viral host are conventional, and some such methods are discussed elsewhere herein.

The present invention includes compositions for preventing or ameliorating HPV infections. As such, the invention contemplates vaccines for use in both active and passive immunization embodiments.

One embodiment of the invention is a method of preparing an immunoglobulin for use in prevention or treatment of HPV infection comprising the steps of immunizing a recipient with a vaccine of the invention and isolating immunoglobulin or antibodies from the recipient, and/or recombinantly producing such immunoglobulins or fragments thereof. An immunoglobulin prepared by this method is a further aspect of the invention. A pharmaceutical composition comprising the immunoglobulin of the invention and a pharmaceutically acceptable carrier is a further aspect of the invention which could be used in the manufacture of a medicament for the treatment or prevention of HPV infection. A method for treatment or prevention of HPV infection comprising a step of administering to a patient an effective amount of the pharmaceutical preparation of the invention is a further aspect of the invention.

Inocula for polyclonal antibody production are typically prepared by dispersing the antigenic composition in a physiologically tolerable diluent such as saline or other adjuvants suitable for human use to form an aqueous composition. An immunostimulatory amount of inoculum is administered to a mammal, e.g., a human, and the inoculated subject is then maintained for a time sufficient for the antigenic composition to induce protective antibodies. The antibodies can be isolated to the extent desired by well known techniques such as affinity chromatography (Harlow and Lane, *Antibodies: A Laboratory Manual* 1988).

Antibodies can include antiserum preparations from a variety of commonly used animals, e.g., goats, primates, donkeys, swine, horses, guinea pigs, rats, or man. The animals are bled and serum recovered.

An immunoglobulin produced in accordance with the present invention can include whole antibodies, antibody fragments or subfragments. Antibodies can be whole immunoglobulins of any class, e.g., IgG, IgM, IgA, IgD or IgE, chimeric antibodies or hybrid antibodies with dual specificity to two or more antigens of the invention. They may also be fragments, e.g., F(ab')2, Fab', Fab, Fv and the like including hybrid fragments. An immunoglobulin can also include natural, synthetic, or genetically engineered proteins that act like an antibody by binding to specific antigens to form a complex.

An HPV composition or vaccine of the present invention can be administered to a recipient who then acts as a source of immunoglobulin, produced in response to challenge from the HPV composition. A subject thus treated would donate plasma from which hyperimmune globulin would be obtained via conventional plasma fractionation methodology. The hyperimmune globulin would be administered to another subject in order to impart resistance against or treat HPV infection. Hyperimmune globulins of the invention are particularly useful for treatment or prevention of HPV infection in infants, immune compromised individuals or where treatment is required and there is no time for the individual to produce antibodies in response to vaccination.

An additional aspect of the invention is a pharmaceutical composition comprising one or more monoclonal antibodies (or fragments thereof; preferably human or humanized) reactive against constituents of the immunogenic composition of the invention, which could be used to treat or prevent infection by multiple HPV types.

Methods of making monoclonal antibodies are well known in the art and can include the fusion of splenocytes with myeloma cells (Kohler et al. (1975) *Nature* 256, 495; Harlow et al. *Antibodies: A Laboratory Manual,* 1988). Alternatively, monoclonal Fv fragments can be obtained by screening a suitable phage display library (Vaughan et al. (1998) *Nat Biotech* 16, 535-539). Monoclonal antibodies may be human, humanized, or partly humanized by known methods.

Another aspect of the invention is a kit for vaccination or treatment according to the present invention. In one embodiment, the kit comprises a vial and optionally a package insert with administration instructions, the vial comprises a VLP composition or vaccine for administration according to the methods of the present invention.

Any of the compositions described herein may be included in a kit. In a non-limiting example, reagents for preparing a VLP and/or administering a VLP, or antibodies generated by vaccination with VLP can be included in a kit. The kit may further include reagents for assessing the activity of the VLP both in vitro and in vivo. The kits will thus comprise, in suitable container, a VLP composition. In certain aspects, the kit can include reagents and/or devices for administration, e.g., inhaler or nebulizer. It may also include one or more buffers, compounds, or devices for preparing the composition for administration.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container.

A kit may also include instructions for employing the kit components as well the use of any other reagent not included in the kit. Instructions may include variations that can be implemented.

It is contemplated that such reagents are embodiments of kits of the invention. Such kits, however, are not limited to the particular items identified above and may include any reagent used for the preparation and/or administration of a VLP vaccine of the invention.

Among other uses, kits of the invention can be used in experimental applications. A skilled worker will recognize components of kits suitable for carrying out a method of the invention.

In the foregoing and in the following examples, all temperatures are set forth in uncorrected degrees Celsius; and, unless otherwise indicated, all parts and percentages are by weight.

EXAMPLES

Example I

Materials and Methods

A. Baculovirus Expression of Chimeric L1-L2 Proteins

L2 peptides of HPV16 were genetically engineered into the DE-surface loops of BPV1 L1 (by insertion between aa 133/134) or HPV16 L1 (between aa 136/137). The primer pairs used in the constructions were as follows:

```
(1.)
                                          (SEQ ID NO: 58)
5'-ctg ttt gca tgt ttt ata aag ggt gac ttt tct
att cac att ttc tgc-3'
(encoding HPV16 L2 aa 18-24/BPV L1 aa 125-133)

(SEQ ID NO: 59)
5'-gca ggt aca tgt cca cct gac acc caa aca aca
gat gac agg-3'
(encoding HPV16 L2 aa 25-31/BPV L1 aa 134-140)

(2.)
                                          (SEQ ID NO: 60)
5'-ccg ctg aat tca ata tgg cgt tgt ggc aac
aag-3'
(encoding EcoRI-BPV L1 aa1-6)

(SEQ ID NO: 61)
5'-gca tga ggt acc gct ttt att tct ttt tct ttt
ttg cag gc-3'
(encoding Kpn1-stop-BPV L1 aa 489-495, thymidines
[nt] 1476 and [nt] 1482 of the wild type BPV1 L1
ORF sequence replaced by cytosines )

(3.)
                                          (SEQ ID NO: 62)
5'-gta taa tgt cag gtg gac atg tac ctg cct gtt
tgc atg ttt tat aaa gtt ggg tga ctt ttc tat
tca c-3'
(encoding HPV16 L2 aa 17-33/BPV L1 aa 128-133)

(SEQ ID NO: 63)
5'-cta agg tta ccc aaa caa cag atg aca gga aac
aaa cag gcc-3'
(encoding HPV16 L2 aa 34-36/BPV L1 aa 134-145)

(4.)
                                          (SEQ ID NO: 64)
5'-cgg ccg cgg ggt gac ttt tct att c-3'
(encoding SstII-BPV L1 aa 129-133)

(SEQ ID NO: 65)
5'-cgg ccg cgg acc caa aca aca gat g-3'
(encoding SstII-BPV L1 aa 134-138)

(5.)
                                          (SEQ ID NO: 66)
5'-ggc gac aca aac gtt ctg caa aac gca caa aac
gtg cat cgg cta ccc aac ttt ata aaa cat gcc
cgc-3'
(encoding HPV16 L2 aa 2-22-SstII)
```

-continued

```
                                        (SEQ ID NO: 67)
5'-ggg cat gtt tta taa agt tgg gta gcc gat gca
cgt ttt gtg cgt ttt gca gaa cgt ttg tgt cgc
cgc-3'
(encoding HPV16 L2 aa 2-22-SstII)
```

(6.)
```
                                        (SEQ ID NO: 68)
5'-gga agg ttg aag gca aaa cta ttg ctg atc aaa
tat tac aat atg gaa gta tgg gtg tat ttt ttg gtg
ggt tag gaa ttg gaa cag ggt cgg gta cag gcg gac
gca ctg ggt ata ttc cat tgc cgc-3'
(encoding HPV16 L2 aa 35-75-SstII)
```

```
                                        (SEQ ID NO: 69)
5'-ggc aat gga ata tac cca gtg cgt ccg cct gta
ccc gac cct gtt cca att cct aac cca cca aaa aat
aca ccc ata ctt cca tat tgt aat att tga tca gca
ata gtt ttg cct tca acc ttcc gc-3'
(encoding HPV16 L2 aa 35-75-SstII)
```

(7.)
```
                                        (SEQ ID NO: 70)
5'-gca tga ccg cgg ttg gga aca agg cct ccc aca
gct ac-3'
(encoding SstII-HPV16 L2 aa 75-83)
```

```
                                        (SEQ ID NO: 71)
5'-gca tga ccg cgg agt ttc ttc cac taa aga aac-3'
(encoding SstII-HPV16 L2 aa 106-112)
```

(8.)
```
                                        (SEQ ID NO: 72)
5'-gca tga ccg cgg att gat gct ggt gca cca ac-3'
(encoding SstII-HPV16 L2 aa 115-121)
```

```
                                        (SEQ ID NO: 73)
5'-gca tga ccg cgg agt agt aac agt att att aat
atc-3'
(encoding SstII-HPV16 L2 aa 147-154)
```

(9.)
```
                                        (SEQ ID NO: 74)
5'-gca tga ccg cgg aat aat act gtt act act gtt
act ac-3'
(encoding SstII-HPV16 L2 aa 149-156)
```

```
                                        (SEQ ID NO: 75)
5'-gca tga ccg cgg ttc tgc agg tgt tgg agg ctg
caa tac-3'
(encoding SstII-HPV16 L2 aa 167-175)
```

(10.)
```
                                        (SEQ ID NO: 76)
5'-gca tga ccg cgg cca aca cct gca gaa act gga
g-3'
(encoding SstII-HPV16 L2 aa 172-178)
```

```
                                        (SEQ ID NO: 77)
5'-gca tga ccg cgg tgt atc cat agg aat ttc ttc
ata att atg-3'
(encoding SstII-HPV16 L2 aa 191-200)
```

(11.)
```
                                        (SEQ ID NO: 78)
5'-gca tga ccg cgg gca tcg gct acc caa ctt tat
aaa ac-3'
(encoding SstII-HPV16 L2 aa 13-21)
```

```
                                        (SEQ ID NO: 79)
5'-gca tga ccg cgg aga aac tat aga agg atc aga
agg gc-3'
(encoding SstII-HPV16 L2 aa 99-107)
```

The sequences encoding HPV16L2 and BPVL1, from which these primers were generated, and the sequences of the encoded proteins are:

HPV16 (114) L2 nucleic acid
(SEQ ID NO: 80)
```
ATGCGACACAAACGTTCTGCAAAACGCACAAAACGTGCATCGGCTAC
CCAACTTTATAAAACATGCAAACAGGCAGGTACATGTCCACCTGACA
TTATACCTAAGGTTGAAGGCAAAACTATTGCTGATCAAATATTACAA
TATGGAAGTATGGGTGTATTTTTTGGTGGGTTAGGAATTGGAACAGG
GTCGGGTACAGGCGGACGCACTGGGTATATTCCATTGGGAACAAGGC
CTCCCACAGCTACAGATACACTTGCTCCTGTAAGACCCCCTTTAACA
GTAGATCCTGTGGGCCCTTCTGATCGTTCTATAGTTTCTTTAGTGGA
AGAAACTAGTTTTATTGATGCTGGTGCACCAACATCTGTACCTTCCA
TTCCCCCAGATGTATCAGGATTTAGTATTACTACTTCAACTGATACC
ACACCTGCTATATTAGATATTAATAATACTGTTACTACTGTTACTAC
ACATAATAATCCCACTTTCACTGACCCATCTGTATTGCAGCCTCCAA
CACCTGCAGAAACTGGAGGGCATTTTACACTTTCATCATCCACTATT
AGTACACATAATTATGAAGAAATTCCTATGGATACATTTATTGTTAG
CACAAACCCTAACACAGTAACTAGTAGCACACCCATACCAGGGTCTC
GCCCAGTGGCACGCCTAGGATTATATAGTCGCACAACACAACAAGTT
AAAGTTGTAGACCCTGCTTTTGTAACCACTCCCACTAAACTTATTAC
ATATGATAATCCTGCATATGAAGGTATAGATGTGGATAATACATTAT
ATTTTTCTAGTAATGATAATAGTATTAATATAGCTCCAGATCCTGAC
TTTTTGGATATAGTTGCTTTACATAGGCCAGCATTAACCTCTAGGCG
TACTGGCATAAGGTACAGTAGAATTGGTAATAAACAAACACTACGTA
CTCGTAGTGGAAAATCTATAGGTGCTAAGGTACATTATTATTATGAT
TTTAGTACCATTGATCCTGCAGAAGAAATAGAATTACAAACTATAAC
ACCTTCTACATATACTACCACTTCACATGCAGCCTCACCTACTTCTA
TTAATAATGGATTATATGATATTTATGCAGATGACTTTATTACAGAT
ACTTCTACAACCCCGGTACCATCTGTACCCTCTACATCTTTATCAGG
TTATATTCCTGCAAATACAACAATTCCTTTTGGTGGTGCATACAATA
TTCCTTTAGTATCAGGTCCTGATATACCCATTAATATAACTGACCAA
GCTCCTTCATTAATTCCTATAGTTCCAGGGTCTCCACAATATACAAT
TATTGCTGATGCAGGTGACTTTTATTTACATCCTAGTTATTACATGT
TACGAAAACGACGTAAACGTTTACCATATTTTTTTTCAGATGTCTCT
TTGGCT
```

HPV16 (114) L2 protein (SEQ ID NO: 81): (NC_001522)
```
MRHKRSAKRTKRASATQLYKTCKQAGTCPPDHPKVEGKTIADQILQY
GSMGVFFGGLGIGTGSGTGGRTGYIPLGTRPPTATDTLAPVRPPLTV
DPVGPSDPSIVSLVEETSFIDAGAPTSVPSIPPDVSGFSITTSTDTT
PAILDINNTVTTVTTHNNPTFTDPSVLQPPTPAETGGHFTLSSSTIS
THNYEEIPMDTFIVSTNPNTVTSSTPIPGSRPVARLGLYSRTTQQVK
VVDPAFVTTPTKLITYDNPAYEGIDVDNTLYFSSNDNSINIAPDPDF
LDIVALHRPALTSRRTGIRYSRIGNKQTLRTRSGKSIGAKVHYYYDF
STIDPAEEIELQTITPSTYTTTSHAASPTSINNGLYDIYADDFITDT
STTPVPSVPSTSLSGYIPANTTIPFGGAYNIPLVSGPDIPINITDQA
PSLIPIVPGSPQYTIIADAGDFYLHPSYYMLRKRRKRLPYFFSDVSL
AA
```

BPV1 L1 nucleic acid (SEQ ID NO: 82):
```
atggcgttgtggcaacaaggccagaagctgtatctccctccaacccct
gtaagcaaggtgctttgcagtgaaacctatgtgcaaagaaaaagcatt
attatcatgcagaaacggagcgcctgctaactataggacatcatatt
acccagtgtctatcggggccaaaactgttcctaaggtctctgcaaatc
agtataggtatttaaaatacaactacctgatcccaatcaatttgcac
tacctgacaggactgttcacaacccaagtaaagagcggctggtgtggg
cagtcataggtgtgcaggtgtccagagggcagcctcttggaggtactg
taactgggcaccccacttttaatgctttgcttgatgcagaaaatgtga
atagaaaagtcaccaccccaaacaacagatgacaggaaacaaacaggcc
tagatgctaagcaacaacagattctgttgctaggctgtaccctgctg
aagggggaatattggacaacagcccgtccatgtgttactgatcgtctag
aaaatggcgcctgccctcctcttgaattaaaaaacaagcacatagaag
atggggatatgatggaaatttgggttggtgcagccaacttcaaagaaa
ttaatgcaagtaaatcagatctacctcttgacattcaaaatgagatct
gcttgtacccagactacctcaaaatggctgaggacgctgctggtaata
gcatgttctttttgcaaggaaagaacaggtgtatgttagacacatct
ggaccagaggggctcggagaaagaagcccctaccacagatttttatt
taaagaataataaaggggatgccaccccttaaaatacccagtgtgcatt
ttggtagtcccagtggctcactagtctcaactgataatcaaatttta
atcggccctactggctattccgtgcccagggcatgaacaatggaattg
catggaataatttattgatttaacagtgggggacaatacacgtggtac
taatcttaccataagtgtagcctcagatggaaccccactaacagagta
tgatagctcaaaattcaatgtataccatagacatatggaagaatataa
gctagcctttatattagagctatgctctgtggaaatcacagctcaaac
tgtgtcacatctgcaaggacttatgccctctgtgcttgaaaattggga
aataggtgtgcagcctcctacctcatcgatattagaggacacctatcg
ctatatagatgtctcctgcaactaaatgtgcaagcaatgtaattcctgc
aaaagaagaccctatgcagggtttaagttttggaacatagatcttaa
agaaaagctttctttggacttagatcaatttccctgggaagaagatt
tttagcacagcaaggggcaggatgttcaactgtgagaaaacgaagaat
tagccaaaaaaacttccagtaagcctgcaaaaaaaaaaaaaaaataa
```

-continued

BPV1 L1 protein (SEQ ID NO: 83):
MALWQQGQKLYLPPTPVSKVLCSETYVQRKSIFYHAETERLLTIGHPY
YPVSIGAKTVPKVSANQYRVFKIQLPDPNQFALPDRTVHNPSKERLVW
AVIGVQVSRGQPLGGTVTGHPTFNALLDAENVNRKVTTQTTDDRKQTG
LDAKQQQILLLGCTPAEGEYWTTARPCVTDRLENGACPPLELKNKHIE
DGDMMEIGFGAANFKEINASKSDLPLDIQNEICLYPDYLKMAEDAAGN
SMEFFARKEQVYVRHIWTRGGSEKEAPTTDFYLKNNKGDATLKIPSVH
FGSPSGSLVSTDNQIENRPYWLFRAQGMNNGIAWNNLLFLTVGDNTRG
TNLTISVASDGTPLTEYDSSKENVYHRHMEEYKLAFILELCSVEITAQ
TVSHLQGLMPSVLENWEIGVQPPTSSILEDTYRYIESPATKCASNVIP
AKEDPYAGFKFWNIDLKEKLSLDLDQFPLGRRFLAQQGAGCSTVRKRR
ISQKTSSKPAKKKKK The sequence encoding HPV16 L1, which is used in the construction of construct J shown in FIG. 1, and the sequence of the encoded protein, are:

HPV16 (114K) L1 nucleic acid
(SEQ ID NO: 84)
ATGTCTCTTTGGCTGCCTAGTGAGGCCACTGTCTACTTGCCTCCTGTC
CCAGTATCTAAGGTTGTAAGCACGGATGAATATGTTGCACGCACAAAC
ATATATTATCATGCAGGAACATCCAGACTACTTGCAGTTGGACATCCC
TATTTTCCTATTAAAAAACCTAACAATAACAAATATTAGTTCCTAAA
GTATCAGGATTACAATACAGGGTATTTAGAATACATTTACCTGACCCC
AATAAGTTTGGTTTTCCTGACACCTCATTTTATAATCCAGATACACAG
CGGCTGGTTTGGGCCTGTGTAGGTGTTGAGGTAGGTCGTGGTCAGCCA
TTAGGTGTGGGCATTAGTGGCCATCCTTTATTAAATAAATTGGATGAC
ACAGAAAATGCTAGTGCTTATGCAGCAAATGCAGGTGTGGATAATAGA
GAATGTATATCTATGGATTACAAACAAACACAATTGTGTTTAATTGGT
TGCAAACCACCTATAGGGGAACACTGGGGCAAAGGATCCCCATGTACC
AATGTTGCAGTAAATCCAGGTGATTGTCCACCATTAGAGTTAATAAAC
ACAGTTATTCAGGATGGTGATATGGTTGATACTGGCTTTGGTGCTATG
GACTTTACTACATTACAGGCTAACAAAAGTGAAGTTCCACTGGCATATT
TGTACATCTATTTGCAAATATCCAGATTATATTAAAATGGTGTCAGAA
CCATATGGCGACAGCTTATTTTTTATTTACGAAGGGAACAAATGTTT
GTTAGACATTTATTTAATAGGGCTGGTACTGTTGGTGAAAATGTACCA
GACGATTTATACATTAAAGGCTCTGGGTCTACTGCAAATTTAGCCAGT
TCAAATTATTTTCCTACACCTAGTGGTTCTATGGTTACCTCTGATGCC
CAAATATTCAATAAACCTTATTGGTTACAACGAGCACAGGGCCACAAT
AATGGCATTTGTTGGGGTAACCAACTATTTGTTACTGTTGTTGATACT
ACACGCAGTACAAATATGTCATTATGTGCTGCCATATCTACTTCAGA
ACTACATATAAAAATACTAACTTTAAGGAGTACCTACGACATGGGGAG
GAATATGATTTACAGTTTATTTTTCAACTGTGCAAAATAACCTTAACT
GCAGACGTTATGACATACATACATTCTATGAATTCCACTATTTTGGAG
GACTGGAATTTTGGTCTACAACCTCCCCCAGGAGGCACACTAGAAGAT
ACTTATAGGTTTGTAACATCCCAGGCAATTGCTTGTCAAAAACATACA
CCTCCAGCACCTAAAGAAGATCCCCTTAAAAAATACACTTTTTGGGAA
GTAAATTTAAAGGAAAAGTTTTCTGCAGACCTAGATCAGTTTCCTTTA
GGACGCAAATTTTTACTACAAGCAGGATTGAAGGCCAAACCAAAATTT
ACATTAGGAAAACGAAAAGCTACACCCACCACCTCATCTACCTCTACA
ACTGCTAAACGCAAAAACGTAAGCTGTAA HPV16 (114K) L1 protein (SEQ ID NO: 85):
MSLWLPSEATVYLPPVPVSKVVSTDEYVARTNIYYHAGTSRLLAVGHP
YFPIKKPNNNKILVPKVSGLQYRVFRIHLPDPNKFGFPDTSFYNPDTQ
RLVWACVGVEVGRGQPLGVGISGHPLLNKLDDTENASAYAANAGVDNR
ECISMDYKQTQLCLIGCKPPIGEHWGKGSPCTNVAVNPGDCPPLELIN
TVIQDGDMVDTGFGAMDFTTLQANKSEVPLDICTSICKYPDYIKMVSE
PYGDSLFFYLRREQMFVRHLFNRAGTVGENVPDDLYIKGSGSTANLAS
SNYFPTPSGSMVTSDAQIFNKPYWLQRAQGHNNGICWGNQLFVTVVDT
TRSTNMSLCAAISTSETTYKNTNFKEYLRHGEEYDLQFIFQLCKITLT
ADVMTYIHSMNSTILEDWNFGLQPPPGGTLEDTYRFVTSQAIACQKHT
PPAPKEDPLKKYTFWEVNLKEKFSADLDQFPLGRKFLLQAGLKAKPKF
TLGKRKATPTTSSTSTTAKRKKRKL Reverse-orientated (back-to-back) synthetic oligonucleotides (1., see primer pairs above) encoding HPV16 L2 aa 18-31 were used for insertion into the BPV1 L1 ORF by an inverse-touchdown-PCR, using the baculovirus transfer vector BPV1 L1-pEVmod (Kirnbauer et al. (1992) Proc Natl Acad Sci USA 89, 12180-12184). To avoid non-specific products the annealing temperature was decreased by 1.5° C. over seven cycles, followed by additional 30 cycles at the final touchdown temperature. Subsequently, the inserted L2 sequences were joined by blunt-end ligation. Silent mutations were introduced into the C-terminal L1 ORF (poly-A tract) by (2.) to avoid mutations of the amplimer. The mutated L1-L2 sequence was recloned into vector pEVmod and inserted L2-epitopes were further elongated by reapplication of PCR (3.)

The following series of peptides spanning the N-terminus of HPV16 L2 were incorporated into BPV1 L1 pEVmod employing a newly established SstII (ccgcgg) restriction enzyme site inserted between aa 133/134 by inverse-touchdown PCR using primer pair (4.). Double-stranded oligonucleotides (with flanking SstII sites) encoding HPV16 L2 peptides aa 2-22 (5.), aa 35-75 (6.) were generated by synthetic oligonucleotide annealing, or by generating PCR-amplimers encoding HPV16 L2 aa 75-112 (7.), aa 115-154 (8.), aa 149-175 (9.), aa 172-200 (10.), aa 13-107 (11.), respectively and cloned into the SstII site of BPV L1 (aa 133/134). SstII (ccgcgg) encodes for proline (P)-arginine (R), added to both ends of L2 in the translated fusion proteins.

A plasmid encoding HPV16 L1 (derived from genomic clone 114K (27))-HPV16 L2 aa 17-36 (further referred to as 16L1-16L2 17-36) was generated by subcloning of codon-optimized synthetic oligos (Geneart, Germany) into the BglII to KpnI sites of baculovirus transfer vector pSynwtVI- (Kirnbauer et al. (1993) J Virol 67, 6929-36). Recombinant expression vectors were verified by bidirectional sequencing (VBC-Biotech; Vienna, Austria).

Recombinant baculoviruses were generated by co-transfection of Sf-9 insect cells with transfer vectors and linearized baculovirus DNA (BaculoGold, BD Biosciences). Expression and purification of VLP were performed as described previously in Kirnbauer et al. (1992) (supra). In brief, chimeric proteins were expressed by infection of insect cells with amplified baculovirus stocks for 3 days. Subsequently, harvested cells were lysed by sonication in PBS/0.8M NaCl/2 mM CaCl2/1 mM PMSF. Following addition of 0.5% Brij58, proteins were incubated over night at 4° C. High-molecular mass structures were purified by ultracentrifugation on sucrose/PBS cushions (35% wt/vol) and CsCl/PBS 29% (wt/wt) density gradients for at least 24 hours each.

Disassembly of VLP into pentameric capsomers was achieved under reducing conditions by extensive dialyzing into 10 mM TrisHCl pH 7.9/10 mM DTT/7.5% 2-mercaptoethanol (2-ME) (adapted by McCarthy et al. (1998) J Virol 72, 32-41) Immunizations were performed with pentamers redialyzed into equivalent buffer without 2-ME. For immunizations with denatured antigen, VLP were dialyzed against PBS (0.5 M NaCl/1 mM CaCl2/0.02% Tween-80) and boiled in 4% SDS.

B. Western Blot

Sf-9 cells were infected for 3 days, harvested, denatured in lysis buffer (2% 2-ME) and analyzed by SDS-Page and Western Blot. Expression of L1 proteins was verified by monoclonal antibody (mAb) AU1 recognizing the linear BPV L1 epitope DTYRYI (BAbCO) (SEQ ID NO:93), or Camvir-1 raised against HPV16 L1 (BD Pharmingen). To verify antigenicity of L2 peptides samples were probed with mAb RG-1 directed to HPV16 L2 aa 17-36 (Gambhira et al. (2007b) J Virol 81, 13927-31), or polyclonal rabbit sera raised against His-tagged HPV16 L2 aa 1-88 or His-tagged HPV16 L2 aa 11-200 (Pastrana et al. (2005a) Virology 337, 365-72).

C. Transmission Electron Microscopy (TEM)

Purified particles were loaded on glow-discharged carbon-coated copper grids, fixed on 2.5% glutaraldehyde, negatively stained with 1% uranylacetate, and visualyzed by JEOL 1010 electron microscope at 80 kV and ×30,000 magnification.

D Immunization

Proteins were extensively dialyzed against PBS containing 0.5 M NaCl/1 mM CaCl2/0.02% Tween-80. Two New Zealand White rabbits (NZW) were immunized with each 50

μg native or SDS-denatured particles in complete Freund's adjuvant (CFA), followed by three boosts four, six and eight weeks later in incomplete Freund's (IFA) (Charles River; Kisslegg, Germany). Alternatively, immunogens were administered in a 10:1 mixture of aluminium hydroxide gel (A8222, Sigma-Aldrich) and monophosphoryl lipid A (S6322, Sigma-Aldrich) (referred to as Alum-MPL) prepared according to the manufacturer's protocols. Balb/c mice were given 10 μg of antigen and boosted four, eight and ten weeks after the first injection. Sera were collected 14 days after the last boost and stored at −20° C.

E. ELISA

Specific antibody titers in antisera raised against BPV1 L1-HPV16 L2 (further referred to as BL1-16L2) aa 2-22, 75-112, 115-154, 149-175, 172-200 were determined by ELISA, using His-tagged HPV16 L2 aa 1-88 or HPV16 L2 aa 11-200 polypeptides to coat the microtiter plates.

These antigens were generated using the pET28A vector (Pastrana et al. (2005a) (supra)) transformed into *E. coli* Rosetta DE3 (Novagen), induced by IPTG and affinity purified on Ni-NTA columns (Qiagen). Eluted proteins were pooled, verified by Western Blotting, quantified via BCA Protein Assay Kit (Pierce) and stored at −20° C.

ELISA was performed as described previously (Gambhira et al. (2007b) *J Virol* 81, 13927-31). Maxisorb plates (Nunc) were coated overnight with 0.1 μg/well L2 peptide in carbonate buffer (pH 9.6) and blocked with 1% BSA-PBS. Ten-fold serial dilutions of antisera were incubated in triplicate wells in BSA/PBS/0.05% Tween-20 (Tw-20). Following 3 washes with PBS/0.05% Tween-20 peroxidase-conjugated antibody in BSA/PBS/0.05% Tween-20 (1:5000) was added and incubated for 1 hour at room temperature. Finally, plates were washed and developed by adding the substrate ABTS (Boehringer Mannheim). The optical density (OD) at 405 nm was determined using an ELISA reader (Dynatech).

F. ELISA Using Synthetic Biotinylated HPV16 L2 aa 18-31 Peptide

Antisera raised against BL1-16L2 aa 18-31, BL1-16L2 aa 17-36, 16L1-16L2 aa 17-36 were examined by ELISA using the biotinylated peptide HPV16 L2 aa 18-31 (LYKTCK-QAGTCPPD (SEQ ID NO:94); JPT Peptide Technologies; Berlin, Germany) as antigen (Slupetzky et al. (2007) *Vaccine* 25, 2001-10). One μg peptide/well was added to Nunc streptavidin plates overnight (as specified by Nunc Streptavidin general coating protocol). Plates were washed with PBS, blocked overnight with 0.5% non-fat dry milk-powder/PBS at 4° C., and incubated with serially diluted antisera for 1 hour at room temperature. Following three washes with PBS, a 1:10,000 dilution of conjugate was added, plates were washed, developed with ABTS and OD determined at 405 nm.

G. Pseudovirion Neutralization Assay

Pseudovirions were produced in 293TT cells and purified on Optiprep gradients (Sigma) as described by Buck et al. (see the world wide web syite:ccr.cancer.gov/lco/protocols.asp) with minor modifications. The following plasmids for expression of L1 and L2 capsid proteins or secreted alkaline phosphatase (SEAP) were used:

Packaging Plasmids:

HPV5: p5sheLL; HPV6: p6sheLL; HPV16: p16L1h, p16L2h; HPV18: peL1fB, peL2bhb; HPV45: p45shell, CRPV: pCRPVL1, pCRPVL2 (provided by J. Schiller, NIH, plasmid maps and references: see the world wide web site home.ccr.cancer.gov/Lco/plasmids.asp), HPV31: p31L1h, p31L2h (Konda et al. (2007) *Virology* 358, 266-72); HPV52: p52L1h, p52L2h (unpublished) HPV58: p58L1h, p58L2h (Konda et al. (2007) (supra)) (provided by Kanda, Tokyo)

HPV11: HPV11 L1, HPV11L2, HPV11 L1/L2, unpublished (provided by M. Müller, Heidelberg)

Target Plasmid:

pYSEAP (provided by J. Schiller, NIH)

Expression vectors for packaging capsid proteins were co-transfected with reporter plasmid pYSEAP and capsid yield was detected colorimetrically. Neutralization assays were performed according to an adapted protocol (see the world wide web site:ccr.cancer.gov/lco/neutralizationassay.htm). Pseudovirions were pre-incubated with 1:2 serial dilutions of sera starting at 1:100 in duplicate wells on ice for 1 hour. Following infection with pseudovirion solutions, 293TT cells were incubated for 72 hours at 37° C. and SEAP activity was determined in clarified cell supernatants colorimetrically at 405 nm (Alphs et al. (2008) *Proc Natl Acad Sci USA* 105, 5850-5). Neutralization titers were reported as the reciprocals of the highest dilution causing 50% reduction of SEAP activity in each assay, compared to pre-immune sera of the same dilution. When reduction of SEAP was close to 50% at 1:100 dilution, sera were re-evaluated at 1:50.

Example II

Results

Previous studies reported that immunization with peptide aa 1-88 of HPV16 L2 induced low titer humoral immune responses to homologous HPV16 and cross-neutralization of heterologous types in vitro (Pastrana et al. (2005a) (supra)) and that vaccination with peptides aa 11-200 of HPV16 L2 confers cross-protection in vivo against challenge by CRPV and ROPV (Gambhira et al. (2007a) *J Virol* 81, 11585-92). In order to enhance antibody titers generated by immunization, L2 peptides were incorporated into a surface displayed site of L1, presumably resulting in a 360-fold array of L2 on the capsid surface.

Figure 1:
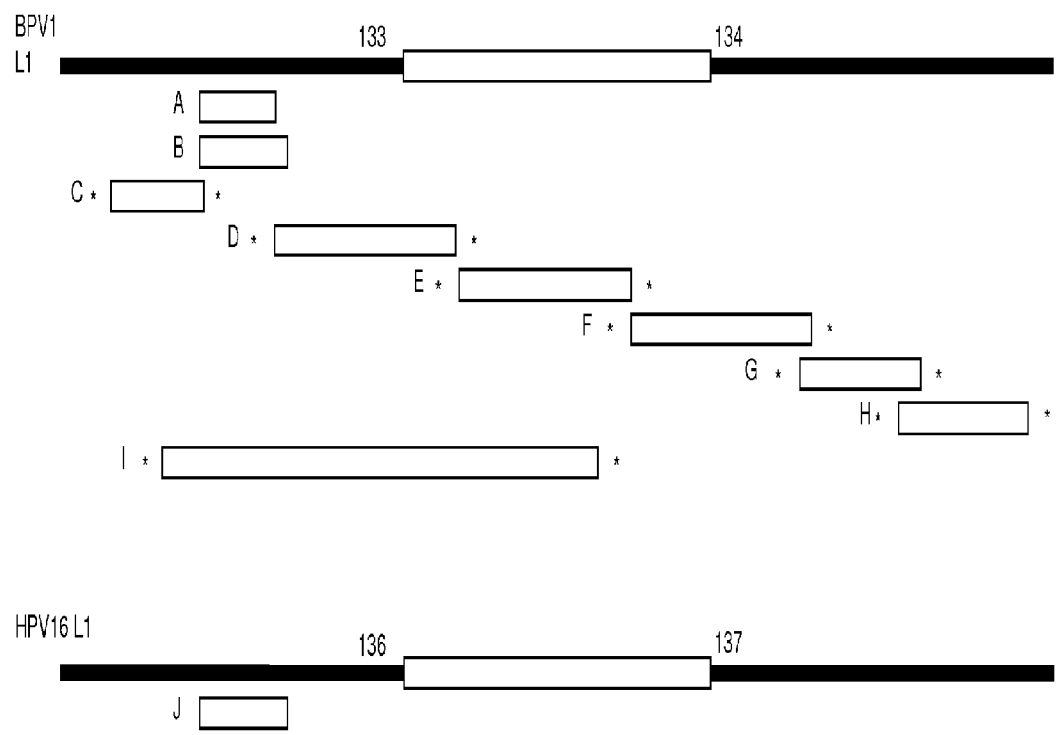
FIG. 1 shows a summary of chimeric L1-L2 fusion proteins A-J. HPV16 L2 peptides with indicated amino acid residues were inserted into the DE loop of BPV1 L1 protein (between residues 133/134), or HPV16 L1 protein (between residues 136/137). Solid lines indicate L1 proteins. Open bars indicate L2 peptides. * Indicates 2 amino acids (Pro and Arg) added N- and C-terminal to the respective peptide resulting from restriction enzyme sites used for cloning. Schemes are not drawn to scale.

Previously, peptides up to 9 aa in length have been successfully expressed by the DE-loop on the BPV1 VLP-surface without compromising the ability to assemble into immunogenic VLP (Handisurya et al. (2007) *FEBS J* 274, 1747-1758; Slupetzky et al. (2007) (supra)). Therefore, the DE loop of L1 was chosen for insertion to display the L2 peptide on the surface of the assembled chimeric BPV1 VLP (FIG. 1). The use of BPV1 capsids as carrier avoids induction of neutralizing anti HPV L1 antisera that might obscure detection of low-titer anti HPV16 L2 (cross-)neutralizing antibodies. Coding sequences for nine partially overlapping HPV16 L2 peptides aa 18-31 (A), aa 17-36 (B, corresponding to the epitope of mAb RG-1); aa 2-22 (C), aa 35-75 (D), aa 75-112 (E), aa 115-154 (F), aa 149-175 (G), aa 172-200 (H), aa 13-107 (I) were inserted between codons 133 and 134 of BPV1 L1. An expression vector for an additional chimeric L1-L2 fusion protein with insertion of HPV16 L2 aa 17-36 into HPV16 L1 (16L1-16L2 17-36) (J) was also generated. As HPV16 is the most important high-risk type causing 50% of cervical cancers worldwide, we reasoned that the use of HPV16 L1 VLP as carrier for HPV 16 L2 would enable induction of a combined high-titer anti HPV 16 L1 and a broadly cross-neutralizing anti L2 immune response. Here, insertion into the DE-loop of HPV16 L1 between codons 136 and 137 was chosen by sequence alignment.

Figure 2:
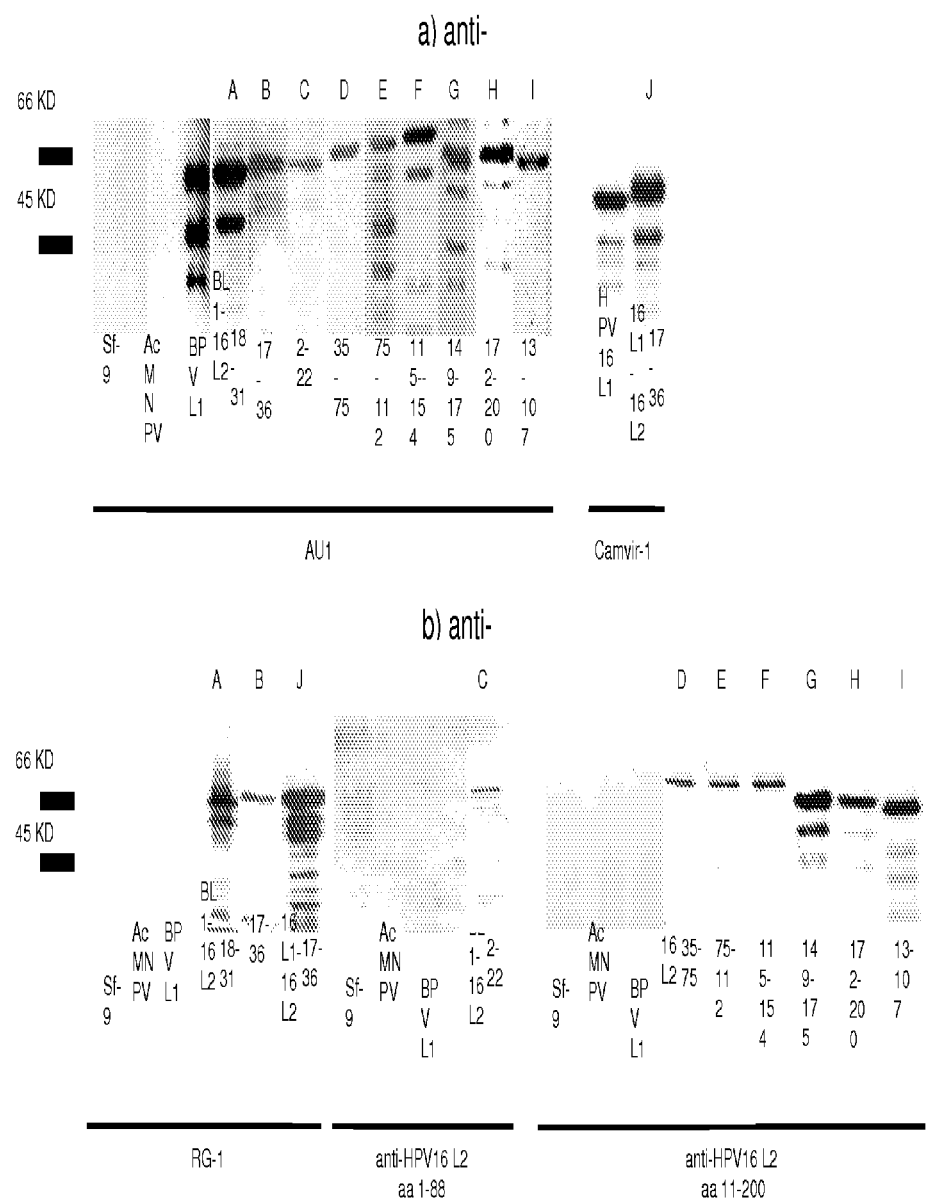
FIG. 2a shows an analysis of chimeric fusion proteins (by Western Blot of Sf-9 cell lysates infected by recombinant baculoviruses. MAb AU1 or Camvir-1 detected BPV1 L1 or HPV16 L1 of chimeric VLP as major bands within a range of 45-60 KD. Reactivity to lower MW bands is likely due to proteolytic degradation products. Both mAb were non-reactive with lysates of uninfected Sf-9 cells or wt baculovirus (AcMNPV) infected insect cells. Wild type BPV1 L1 or HPV16 L1 proteins were used as controls.
FIG. 2b shows antigenicity of incorporated L2 peptides was verified with mAb RG-1 (A, B, J) or polyclonal rabbit sera to HPV16 L2 aa 1-88 (C) and HPV16 L2 aa 11-200 (D, E, F, G, H, I) respectively. D, E, and F were used as gradient-purified fusion proteins.

Recombinant baculoviruses were generated and used for infection of Sf-9 insect cells. Three days later, cells were lysed and analyzed by SDS-PAGE. Western blotting of recombinant proteins with mAb AU1 (anti-BPV L1) and Camvir-1 (anti-HPV16 L1) showed migration within a range of 45-60 KD (FIG. 2a, A-J). As expected, migration of most L1-L2 fusion proteins was slightly slower compared to wild-type L1 proteins.

Antigenicity of inserted HPV 16 L2 peptides was verified by mAb RG-1 (anti-HPV 16 L2 aa 17-36) or polyclonal rabbit sera raised against HPV16 L2 aa 1-88 or HPV16 L2 aa 11-200 as appropriate (FIG. 2b). Several faster migrating bands are probably caused by protein degradation.

Native L1 VLP trigger higher titer neutralizing antibodies than subunit pentamers, and the pentamers are dramatically more immunogenic than monomeric, denatured L1 protein. Thus the assembly status of chimeric L1-L2 proteins was determined by TEM. In case of equivocal morphological formations, assembly into capsomers was further distinguished by ELISA performed with conformation-dependent mAb 5B6, whose binding is dependent on BPV1 L1 assembly into pentamers (Slupetzky et al. (2001) *J Gen Virol* 82, 2799-804).

Figure 3:
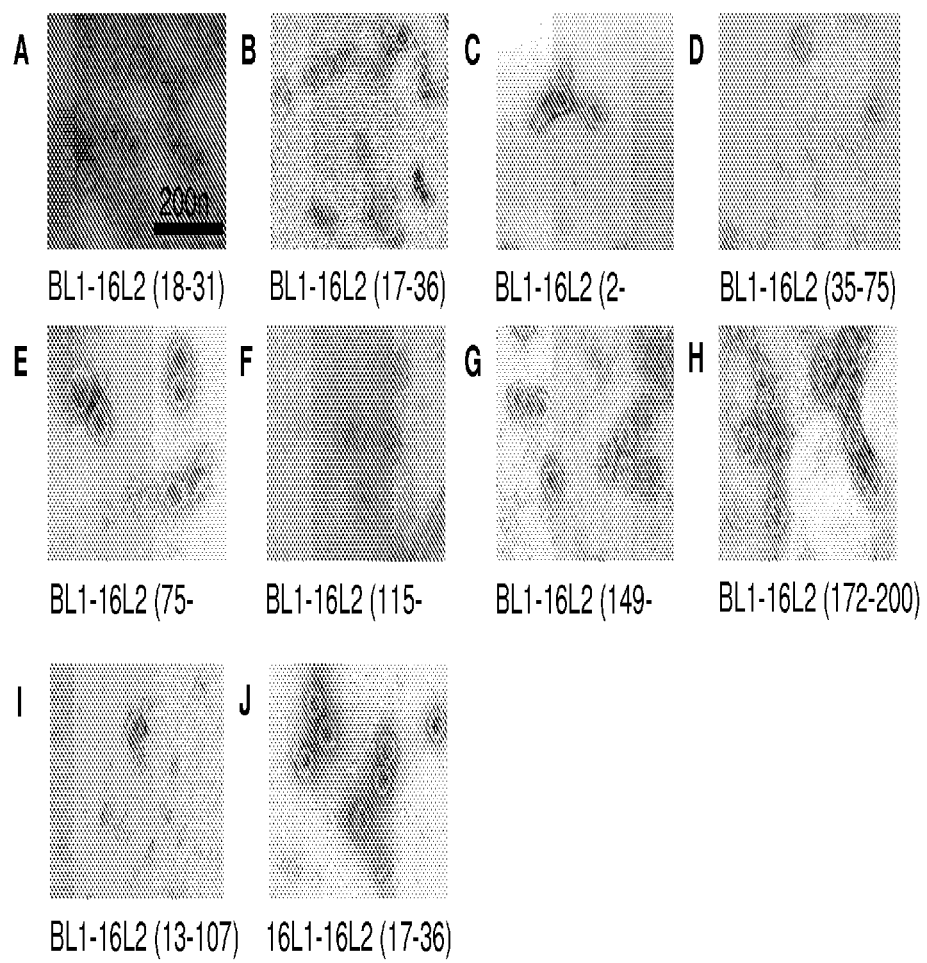
FIG. 3 shows transmission electron microscopy (TEM) of purified particle preparations, x 30,000: Chimeric proteins BL1-16L2 18-31 (A), 17-36 (B), 2-22 (C), 75-112 (E), 115-154 (F), 149-175 (G) and 172-200 (H) and 16L1-16L2 17-36 (J) assemble into VLP, with a size of approximately 50-60 nm. BL1-16L2 35-75 (D) and BL1-16L2 13-107 (I) do not unequivocally form capsomers or VLP.

As shown in FIG. 3, TEM demonstrated assembly into full-size VLP (approximately 50-60 nm diameter) of BL1-16L2 18-31 (A), 17-36 (B), 2-22 (C), 75-112 (E), 115-154 (F), 149-175 (G) and 172-200 (H), and 16L1-16L2 17-36 (J). Chimeric proteins BL1-16L2 35-75 (D) and BL1-16L2 13-107 (I) existed in less ordered conformations, suggesting the presence of L1 pentamers or protein aggregates. To further distinguish these possibilities, ELISAs using mAb 5B6 (38) and mAb AU1 were performed. Neither of the protein preparations that lacked VLP (D and I) reacted with 5B6, suggesting that chimeric proteins D and I were unable to assemble into pentamers. Moreover, results demonstrated enhanced binding of mAb AU1 with denatured BL1-16L2 13-107 (I), compared to native preparations, but not for BL1-16L2 35-75 (D), suggesting a partially conformation-dependent formation of the former (I) but not the latter protein (D) (data not shown). Consequently, we refrained from immunization with BL1-16L2 35-75.

Taken together eight out of ten chimeric proteins were able to assemble into VLP, presenting up to 44 aa of 16L2 (BL1-16L2 115-154 (F), plus four aa encoded by flanking restriction enzyme sites SstII) within the DE-surface loop of BPV1 L1, and 20 aa within HPV16 L1 (J), respectively (FIG. 1, 3).

L2—Specific Serum Antibodies

Immunogencity of chimeric L1-L2 VLP and humoral immune responses to displayed L2 peptides were determined by immunization of NZW rabbits. Each antigen was administered either as native particles or SDS-denatured antigen, in order to determine the impact of particle structure on immunogenicity Immunizations were performed using the potent adjuvant Freund's (CFA/IFA). Antigens that induced broadly cross-neutralizing antibody responses were further administered using human-applicable Alum-MPL as adjuvant. Moreover, inbred Balb/c mice were inoculated with antigen-Alum-MPL formulations in order to encompass an alternative mammalian system.

Two NZW rabbits were immunized in CFA/IFA with BL1-16L2 18-31 (A), 17-36 (B), 2-22 (C), 75-112 (E), 115-154 (F), 149-175 (G), 172-200 (H), each as native or SDS-denatured preparations. Due to its incomplete assembly, BL1-16L2 13-107 (I)-protein was inoculated as native preparation only.

By ELISA, L2-specific immune responses were detected using synthetic peptide HPV16 L2 aa 18-31, or bacterially expressed HPV16 L2 aa 1-88 or aa 11-200 proteins, respectively as antigens (Table 2). Apart from BL1-16L2 2-22 (C), all VLP preparations induced significant antibody responses (titers ranging from 2,500-312,500), while corresponding denatured proteins each elicited antibody levels that were typically five times lower (titers of 500-12,500). Preimmune sera were non-reactive in all cases.

These results demonstrate improved immunogenicity of epitopes present on native VLP, compared to analogous denatured proteins. The complete absence of a detectable humoral response to L2 by BL1-16L2 2-22 (C) immunization suggests that the N-terminal 20 aa of HPV16 L2 do not represent a B-cell epitope in rabbits. Moreover, the inability of BL1-16L2 13-107 (I) to assemble into VLP may be responsible for inducing only a modest anti-L2 immune response (titers of 500) (Table 2).

TABLE 2

| rabbit | antisera to BL1-16L2 (L2-ELISA) | | | | | | | |
|---|---|---|---|---|---|---|---|---|
| antisera CFA/IFA | 18-31 (A) | 17-36 (B) | 2-22 (C) | 75-112 (E) | 115-154 (F) | 149-175 (G) | 172-200 (H) | 13-107 (I) |
| native protein | | | | | | | | |
| NZW #1 | 62,500 | 62,500 | 0 | 2,500 | 62,500 | 62,500 | 312,500 | 500 |
| NZW #2 | 62,500 | 62,500 | 0 | 2,500 | 62,500 | 62,500 | 312,500 | 500 |
| denat. protein | | | | | | | | |
| NZW #3 | 12,500 | 2,500 | 0 | 500 | 2,500 | 12,500 | 12,500 | x |
| NZW #4 | 12,500 | 100 | 0 | 500 | 2,500 | 2,500 | 12,500 | x |

Evaluation of rabbit antisera by HPV16 L2 peptide ELISA. Two NZW rabbits each were vaccinated with indicated chimeric BL1-16L2 proteins, either as native VLP or SDS-disrupted preparations, using Freund's (CFA/IFA) as adjuvant. ELISA was performed using HPV16 L2 1-88 (for sera raised against BL1-16L2 2-22), HPV16 L2 aa 18-31 (BL1-16L2 18-31, BL1-16L2 17-36), HPV16 L2 aa 11-200 (BL1-16L2 75-112, BL1-16L2 115-154, BL1-16L2 149-175, BL1-16L2 172-200, BL1-16L2 13-107) as ELISA antigens. Sera were serially end-point diluted and tested in triplicates. SDS-disrupted protein BL1-16L2 13-107 has not been used as immunogen (X).

In Vitro Neutralization

Pseudovirion neutralization assays take advantage of papillomavirus-based gene transfer vectors (pseudovirions) to mimic papillomavirus infection and its inhibition in vitro (Buck et al. (2005) *Methods Mol Med* 119, 445-62). Infection of cell cultures with L1/L2 capsids, encapsidating the reporter plasmid pYSEAP, leads to expression of secreted alkaline phosphatase (SEAP), which can be measured in the supernatant, whereas preincubation of pseudovirions with neutralizing antibodies prevents infection and decreases the amount of SEAP. It has been shown that neutralizing antibodies correlate with protection of animals from viral challenge in vivo (Alphs et al. (2008) (supra); Gambhira et al. (2007b) (supra)).

Neutralization assays were performed with pseudovirions of L2-homologous type HPV16 and L2-divergent high-risk HPV18 (Table 3a). Sera unable to neutralize infection with either type were not further evaluated. All sera were tested in 10-fold serial dilutions from 1:100-1:100,000, evidence of lower antibody levels was reevaluated for serum dilutions of 1:50, whereas titers <50 were considered insignificant.

Immunization of rabbits with BL1-16L2 17-36 (B) VLP (comprising the RG-1 epitope) induced neutralizing antibodies against five high-risk HPV types, HPV16 (1,000/10,000), HPV18 (100-1,000/1,000), HPV45 (100/100-1,000), HPV52 (0/100), HPV58 (100/1,000), low-risk type HPV11 (0/50-

TABLE 3a a antisera to BL1-16L2 (neutralizing titer)

| pseudo-virions | 18-31 (A) native | 18-31 (A) denat. | 17-36 (B) native | 17-36 (B) denat. | 75-112 (E) native | 75-112 (E) denat. | 115-154 (F) native | 115-154 (F) denat. | 13-107 (I) native |
|---|---|---|---|---|---|---|---|---|---|
| HPV 16 | 0 | 100 | 1,000 | 100 | 100 | 50 | 1,000 | 100 | 100 |
|  | 100 | 100 | 10,000 | 100 | 0 | 0 | 100 | 50 | 0 |
| HPV 18 | 0 | 100 | 100-1,000 | 100 | 0 | 0 | 0 | 0 | 0 |
|  | 0 | 100 | 1,000 | 0 | 0 | 0 | 0 | 0 | 0 |
| HPV 31 | 0 | 0 | 0 | 0 | 0 | x | 0 | 0 | 0 |
|  | 0 | 0 | 0 |  | x | x | 0 | x | x |
| HPV 45 | 0 | 100 | 100 | 0 | 0 | x | 0 | 0 | 0 |
|  | 0 | 0 | 100-1,000 |  | x | x | 0 | x | x |
| HPV 52 | 0 | 0 | 0 | 0 | 0 | x | 0 | 0 | 0 |
|  | 0 | 100 | 100 |  | x | x | 0 | x | x |
| HPV 58 | 0 | 0 | 100 | 100 | 0 | x | 0 | 0 | 50 |
|  | 0 | 100 | 1,000 | 0 | x | x | 0 | x | x |
| HPV 6 | 0 | 0 | 0 | 0 | 0 | x | 0 | 0 | 0 |
|  | 0 | 0 | 0 |  | x | x | 0 | 0 | x |
| HPV 11 | 0 | 0 | 0 | 0 | 0 | x | 0 | 0 | 0 |
|  | 0 | 0 | 50-100 |  | x | x | 0 | 0 | x |
| HPV 5 | 0 | 1,000 | 100 | 100 | 0 | x | 0 | 0 | 0 |
|  | 100 | 100 | 10,000 | 0 | x | x | 0 | x | x |
| CRPV | 0 | 0 | 0 | 0 | 0 | x | 0 | 0 | 0 |
|  | 0 | 50 | 0 |  | x | x | 0 | x | x |

| pseudo-virions | 2-22 (C) native | 2-22 (C) denat. | 18-31 (A) pentamer | 149-175 (G) native | 149-175 (G) denat. | 172-200 (H) native | 172-200 (H) denat. |
|---|---|---|---|---|---|---|---|
| HPV 16 | 0 | 0 | 0 | 0 | 0 | 0 | 0 |
|  | 0 | 0 | 0 | 0 | 0 | 0 | 0 |
| HPV 18 | 0 | 0 | 0 | 0 | 0 | 0 | 0 |
|  | 0 | 0 | 0 | 0 | 0 | 0 | 0 |

Pseudovirion neutralization assays of rabbit sera raised against indicated native or denatured (denat.) BL1-16L2 proteins using Freund's (CFA/IFA) as adjuvant. Titers of two animals each are shown. Sera that neutralized neither HPV16 nor HPV18 were not tested (X) for remaining pseudovirion types. Assays were performed with serum dilutions ranging from 1:100 to 1:100,000. When a lower titer of neutralization was suspected sera were re-evaluated at dilution of 1:50.

TABLE 3b b antisera to BL1-16L2 (BPV1- neutralizing titer)

| pseudo-virions | 18-31 (A) native | 17-36 (B) native | 2-22 (C) native | 75-112 (E) native | 115-154 (F) native | 149-175 (G) native | 172-200 (H) native | BL1/L2 native |
|---|---|---|---|---|---|---|---|---|
| BPV1 | 1,000,000 | 100,000 | 10,000 | 1,000,000 | 100,000 | 100,000 | 1,000 | 100,000 |
|  | 100,000 | 1,000,000 | 10,000 | 100,000 | 100,000 | 1,000,000 | 10,000 |  |

Neutralization of BPV1 pseudovirions by sera raised against native BL1-16L2 chimeric VLP. Assays were performed with serum dilutions from 1:100 to 1:100,000. Rabbit serum BPV L1/L2 VLP has been raised against co-expressed wild type BPV L1 plus L2 VLP.

As expected from negative ELISA results, BL1-16L2 2-22 (C) anti-serum did not contain any detectable neutralizing antibodies. One of two rabbits immunized with BL1-16L2 18-31 (A) native VLP developed neutralizing antisera to HPV16 (titer 1:100) and non-related beta-HPV5 (1:100). On the contrary, SDS-denatured antigen induced neutralizing antibodies to those and 4 additional HPV types (titers of both animals given in parenthesis) HPV16 (100/100), HPV18 (100/100), HPV45 (100/0), HPV52 (0/100), HPV58 (0/100), HPV5 (1,000/100) as well as CRPV (0/50). Therefore it was concluded that presentation of peptide HPV16 L2 18-31 in chimeric VLP was disadvantageous to induction of neutralizing antibodies. In addition, animals immunized with BL1-16L2 aa 18-31 (A) disassembled into pentavalent capsomers were incapable of inducing neutralizing antibodies (not shown).

100) and beta-HPV type 5 (100/10,000) Immune sera to disrupted VLP caused less distinct titers to HPV16 (100/100), HPV18 (100/0), HPV58 (100/0) and HPV5 (100/0), and neutralization was undetectable for HPV45, HPV52 and HPV11.

Vaccination with chimeric particles BL1-16L2 75-112 (E) and BL1-16L2 115-154 (F) neutralized HPV16 pseudovirions with titers of (100/0) (E) and (1,000/100) (F) respectively, but did not cross-neutralize any other pseudovirions tested. Corresponding denatured antigens elicited modest titers of (50/0) (E) and (100/50) (F) respectively.

Although both native and denatured BL1-16L2 149-175 (G), BL1-16L2 172-200 (H) induced pronounced 16L2-specific immune responses by ELISA, antisera were non-neutralizing for HPV16 and HPV18. One of two animals, inoculated with BL1-16L2 13-107 (I) protein, evolved neutralizing antibodies against HPV16 (100/0) and HPV58 (50/0) (Table 3a).

Therefore, neutralization epitopes could be mapped within N-terminal HPV16 L2 aa 17-148. However, induction of cross-neutralization to closely related genital high-risk (HPV52, HPV58), as well as phylogenetically divergent high-risk types (HPV18, HPV45), genital low-risk (HPV11), beta-HPV (HPV5), and animal PV (CRPV) was restricted to previously reported HPV16 L2 residues aa 17-36 (the RG-1 epitope). The importance of flanking aa 17 and 32-36 is emphasized by insufficient neutralization of sera raised against construct 18-31. Moreover, presentation on VLP surfaces can improve immunogenicity of displayed epitopes as compared to linear fusion proteins. To determine whether chimeric VLP retained the capability of inducing neutralizing antibodies to conformation dependent epitopes of carrier protein L1, BPV1 pseudovirion neutralization assays were performed (Table 3b). Antisera induced by chimeric VLP (BL1-16L2 18-31 (A), 17-36 (B), 75-112 (E), 115-154 (F), 149-175 (G)) neutralized BPV1 pseudovirions with titers ranging from 100,000 to 1,000,000, whereas two chimeras (BL1-16L2 2-22 (C) and 172-200 (H)) raised lower titers of neutralizing antibodies (1,000 to 10,000). Therefore the insertion of four out of six peptides did not interfere with induction of high-titer neutralizing antibodies against L1, irrespective of the size of incorporated peptides.

Figure 4:
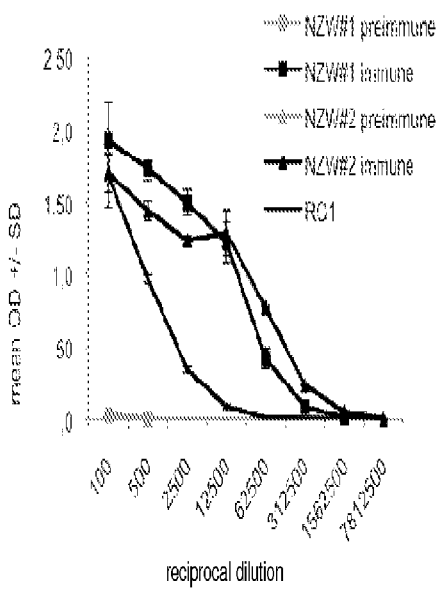
FIG. 4 shows BPV L1-HPV16 L2 (BL1-16L2) 17-36 immunizations of rabbits and mice, using Freund's or Alum-MPL adjuvant and HPV16 L1-HPV16 L2 (16L1-16L2) 17-36 immunizations of rabbits, using Alum-MPL adjuvant: Evaluation by L2-peptide ELISA. ELISAs were performed in triplicates for 5-fold serial serum dilutions from 100 to 7,812, 500. ELISA were performed using synthetic peptide HPV16 L2 aa 18-31 as antigen. Data of BL1-16L2 17-36 antisera indicate L2 specific antibody titers of 62,500-312,500 in NZW using Freund's as adjuvant (FIG. 4a), titers of 12,500 in NZW using Alum-MPL (FIG. 4b), and titers of 2,500-12,500 in Balb/c using Alum-MPL as adjuvant (FIG. 4c). Data of 16L1-16L2 17-36 antisera indicate L2 specific antibody titers of 12,500 in NZW using Alum-MPL (FIG. 4d). MAb RG-1 is directed against HPV16 L2 aa 17-36 (18). Data are shown as mean OD+/−SD.
Figure 4:
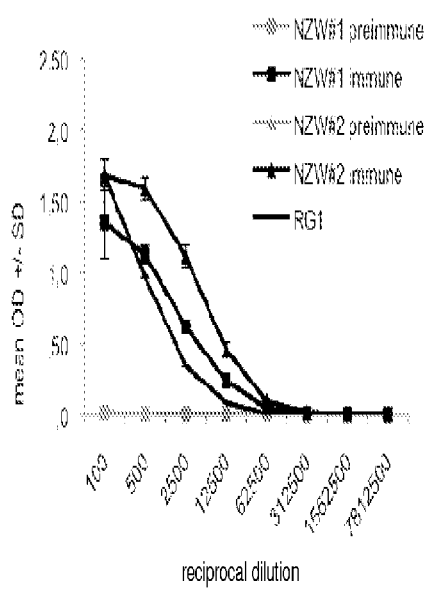
Figure 4:
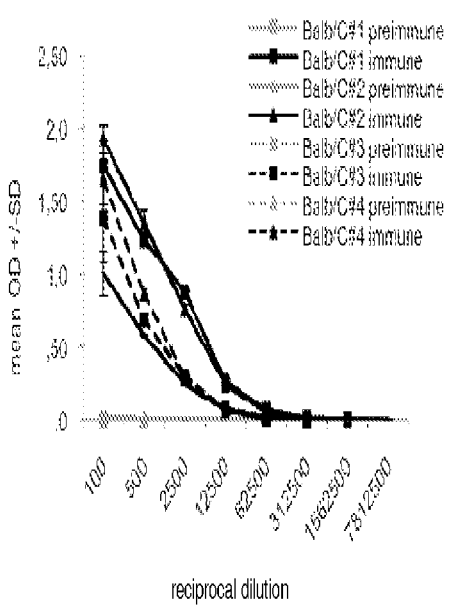
Figure 4:
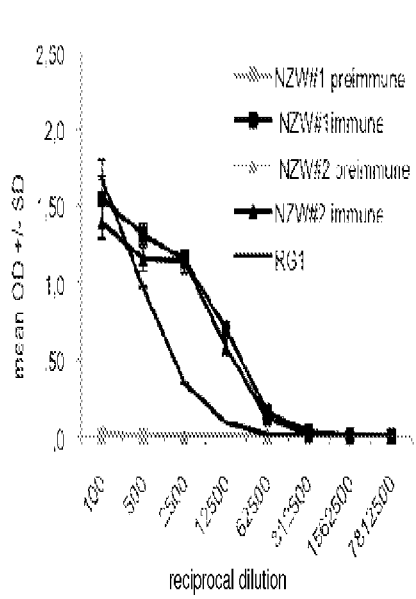

As Freund's is not approved for human use, two additional rabbits were immunized with BL1-16L2 17-36 (B) using Alum-MPL as adjuvant. A comparable formulation (ASO4) is used in the approved HPV L1 vaccine Cervarix®. In addition, four Balb/c mice were vaccinated with the same antigen-adjuvant formulation to further our observations of cross-neutralization to a different mammalian system. Peptide-ELISA detected L2-specific antibody responses with titers of 2,500-12,500 in both rabbits and mice (FIG. 4b, c). Chimeric VLP formulated on Freund's adjuvant (FIG. 4a) induced at least five times higher antibody titers as compared to Alum-MPL.

Both rabbits immunized with Alum-MPL formulation elicited antisera capable of neutralizing high-risk HPV16 (100/100), HPV18 (100/100) and HPV58 (100/100) and beta-type HPV5 (50/50) (Table 4a). In addition, one of the rabbits' sera neutralized high-risk type HPV45 (100) and low-risk HPV6 (titers from 50 to 100) and HPV11 (100). Thus with immunization schedules similar to those with Freund's adjuvant, VLP immunizations using Alum-MPL induced titers that were one or two orders of magnitude lower. Out of four mice immunized with BL1-16L2 17-36, one mouse developed neutralizing antibodies against HPV16 only (titer of 100), two mice elicited antibodies against HPV16 (1,000/50-100) and 18 (1,000/100) and one animal developed antibodies against HPV18 (100), 31 (100), 45 (100), 52 (100) and 58 (100) (Table 4a).

TABLE 4

| pseudo-virions | a BL1-16L2 17-36; Alum-MPL (neutralizing titer) | | b 16L1-16L2 17-36; Alum-MPL (neutralizing titer) |
|---|---|---|---|
| | NZW # 1/2 | Balb/c # 1/2/3/4 | NZW # 1/2 |
| HPV 16 | 100/100 | 0/1,000/100/50-100 | 100,000/100,000 |
| HPV 18 | 100/100 | 100/1,000/0/100 | 1,000/1,000 |
| HPV 31 | 0/0 | 100/0/0/0 | 10,000/1,000 |
| HPV 45 | 100/0 | 100/0/0/0 | 1,000/100 |
| HPV 52 | 0/0 | 100/0/0/0 | 100/50 |
| HPV 58 | 100/100 | 100/0/0/0 | 1,000/1,000 |
| HPV 6 | 50-100/0 | 0/0/0/0 | 100/50 |
| HPV 11 | 100/0 | 0/0/0/0 | 100/0 |
| HPV 5 | 50/50 | 0/0/0/0 | 100/50 |
| CRPV | 0/0 | 0/0/0/0 | 0/0 |

4a. Pseudovirion neutralization assays for antisera of two NZW rabbits and four Balb/c mice immunized with BL1-16L2 17-36 using Alum-MPL as adjuvant.
3b. Pseudovirion neutralization assays of two NZW rabbits' antisera raised against 16L1-16L2 17-36 using Alum-MPL as adjuvant. All assays were performed in duplicates for 10-fold serial serum dilutions of 1:100-1:100,000. When a lower titer of neutralization was suspected, sera were reevaluated at dilution of 1:50.

To further develop HPV capsids as potential vaccine carrier, we incorporated the cross-protective epitope HPV16 L2 aa 17-36 (RG-1) into HPV16 L1 (derived from the German HPV16 variant 114K (Kirnbauer et al. (1993) (supra)). Analogous to the insertion site for BPV1 L1 between aa 133/134, for HPV16 insertion between aa 136/137 was used. These aa are located within the DE-surface loop, adjacent to a hypervariable immunodominant segment of L1. Assembly into VLP was observed by TEM (FIG. 3J). Two NZW rabbits were vaccinated with native VLP adjuvanted by Alum-MPL. As examined by peptide ELISA, immunization induced L2-specific antibodies in both animals with titers of 1:12,500 (FIG. 4*d*).

When analyzed by pseudovirion neutralization assays, both rabbit sera neutralized HPV16 with titers of 100,000, which largely reflects the antibody response to the HPV16 L1 VLP carrier. Moreover, robust neutralization of heterotypic high-risk types HPV18 (1,000/1,000), HPV31 (10,000/1,000), HPV45 (1,000/100), HPV52 (100/50), and HPV58 (1,000/1,000) was observed. In addition, neutralization of low-risk types HPV6 (100/50), HPV11 (100) by one of the rabbits' sera, and beta-type HPV5 (100/50) was detected (Table 4b). As expected, rabbit antiserum #4835 (J. Schiller), raised against HPV16 L1-VLP, adjuvanted by Freund's neutralized HPV16 (1,000,000) and closely related HPV31 (1,000) only (data not shown). These results eliminate the impact of carrier L1 on the broad range of cross-neutralization and indicate that the insertion of L2 peptides does not interfere with high-titer antibody responses to L1.

Discussion

The impact of recently introduced HPV L1 VLP vaccines on the burden of HPV-associated ano-genital neoplasias and their cost-effectiveness are the subject of ongoing studies. Current vaccines target HPV types that cause 90% of ano-genital warts (HPV6, HPV11) and/or 70% of cervical cancers (HPV16, HPV18). Protection by L1 VLP vaccination is primarily type-restricted with partial cross-protection against some phylogenetically related mucosal. Thus cytological screening programs in vaccinated women cannot be abandoned, and the considerable costs for introduction of prophylactic immunization programs in the population must be borne in addition to screening costs. In addition, currently available vaccines are too costly at the moment for use in developing countries, where 80% of the global cervical cancer burden occurs.

Previous studies have demonstrated that vaccination with N-terminal or full-length L2 peptides or proteins can induce a low-titer, yet protective antibody response to a wide-range of divergent papillomavirus types and species. The HPV16 L1-HPV16 L2 VLP vaccination strategy described herein triggers with a single construct both high-titer conformation-dependent neutralizing antibodies similar to monovalent HPV16 L1-VLP vaccination, and significant levels of antibodies to a highly conserved region of L2 that cross-neutralize a broad spectrum of pathogenic HPV types.

Crystallization of small (T=1) L1 HPV16 VLP has revealed the atomic structure of the viral capsid, in particular the hypervariable surface loops that contain the immunodominant and conformation-dependent epitopes that are recognized by neutralizing antibodies and determine the viral serotype (Chen et al. (2000) *Molecular Cell* 5, 557-567). To augment immunogenicity of L2, peptides covering the N-terminus of HPV16 L2 were inserted into corresponding sites of the DE loop of BPV1 L1 and HPV16 L1. The tolerated length of inserted L2 peptide that still allowed for VLP assembly was 44 and 20 residues, respectively Amino acid sequence of the insert appears as additional limitation for VLP assembly. It is noteworthy that sequence analysis strongly predicts the presence of a transmembrane region at 45-67 which may account for the failure of the 35-75 and 13-107 L2 constructs to assemble, and its absence from all of the constructs that do assemble. These observations extend previous studies and confirm that the immunogenic DE-loop is a suitable site for antigen presentation in two different PV genera.

Papillomavirus VLP-based vaccinations induce strong humoral (Carter et al. (1994) *Virology* 199, 284-91; Christensen et al. (1994) *J Gen Virol* 75, 2271-6; Kirnbauer et al. (1992) (supra); Rose et al. (1994) *J Gen Virol* 75, 2445-9), and cell-mediated immune responses to L1 and incorporated antigens (Handisurya et al. (2007) *Feb J* 274, 1747-1758; Lenz et al. (2001) *J Immunol* 166, 5346-55; Pinto et al. (2003) *J Infect Dis* 188, 327-38; Rudolf et al. (2001) *J Immunol* 166, 5917-24; Slupetzky et al. (2001) *J Gen Virol* 82, 2799-804; Yang et al. (2004) *J Immunol* 173, 2624-31; Zamora et al. (2006) *Immunol* 177, 2662-70). Antibody response to VLP is strongly dependent on the density of surface-presented epitopes (Bachman et al. (1997) *Ann Rev Immunol* 15, 235-70; Chackerian et al. (2002) *Jornal of Immunology* (Baltimore, Md.: 1950) 169, 6120-6). We found that rabbits immunized with native chimeric VLP demonstrate robust immune responses to L2 by ELISA, with, on average, 5-fold higher titer as compared to vaccinations with SDS-disrupted proteins (Table 2). Assuming that this difference would likely be even greater in the absence of adjuvant, peptide display on L1 VLP surfaces appears to represent a useful strategy to overcome immune sub-dominance of L2 in its natural context.

A comprehensive examination of B-cell epitopes within the N-terminus of HPV16 L2 was conducted using overlapping peptides. As chimeric BL1-16L2 69-81 and 108-120 have been published previously (Slupetzky et al. (2007) (supra)), adjacent peptides were designed without overlap. Neutralization of homologous HPV16 pseudovirions was achieved by immunizations with chimeric proteins comprising HPV16 L2 aa 13-154 (Table 3a). These observations support previous findings that protective neutralizing antibody response to L2 of divergent PV types is mediated by N-terminal 150 aa of BPV4 L2 (Campo et al. (1997) *Virology* 234, 261-6; Chandrachud et al. (1995) *Virology* 211, 204-8); BPV1 L2 (Pastrana et al. (20005b) *Virology* 337, 365-72); CRPV-ROPV L2 (Embers et al. (2002) (supra)), HPV16 L2 (Embers et al. (2004) *Vaccine* 22, 670-80; Kawana et al. (1998) *Virology* 245, 353-9; Pastrana et al. (2005b) (supra)).

Efficient cross-neutralization of a larger panel of mucosal HPV types was restricted to sera raised against incorporated HPV16 L2 residues aa 17-36, the previously described RG-1 epitope (Gambhira et al. (2007b) (supra)). Residues within this highly conserved region between different PV genus and types were previously determined to interact with a secondary cell surface receptor, while its critical involvement in virus infectivity is allocated to a later stage of infection.

The use of Alum-MPL as the adjuvant narrowed the gap between immunization conditions of animal studies given herein and established L1-subunit vaccines. The formulation approximates the proprietary adjuvant ASO4 of Cervarix®, whose adjuvant characteristics have been attributed to the activation of innate immunity by pro-inflammatory cytokine-pathways as well as induction of memory B cells. Neutralizing antibody patterns between individual rabbits vaccinated with BL1-16L2 17-36 in Freund's or Alum-MPL differ considerably, showing 1-2 log differences in titer, or even negativity to some types, which might be due to antibodies below detection level, rather than different epitope-processing and presentation in individuals. Overall, cross-neutralization was induced in two different mammals and using Alum-MPL as adjuvant, which is applicable for human use.

Most importantly, the levels of neutralizing antibodies induced herein presumably are protective in vivo (Embers et al. (2002) (supra); Gambhira et al. (2007a) (supra); Gaukroger et al. (1996) (supra)). Sensitivity of papillomaviruses to neutralization by low titer antisera may in part be due to the unusually slow uptake kinetics into cells allowing prolonged access to neutralizing antibodies (Culp et al. (2004) *Virology* 319, 152-61). In addition, a vaginal challenge model of mice points to the fact that the virus initially binds to the basement membrane of mechanically disrupted epithelium and eventually adsorbs to the epithelial cells, while they regain contact to the basement membrane (Roberts et al. (2007) Nat Med 13, 857-61).

Despite modification of the L1 VLP surface by L2 insertion, immunization with chimeric BL1-16L2 VLP induced high-titer anti-BPV1 L1 antibodies, irrespective of inserted peptide length. Similarly, 16L1-16L2 17-36 VLP induced high titers of HPV16 neutralizing antibodies, similar to HPV16 wt L1 VLP vaccination, indicating that the major immunogenic epitopes of L1 are retained. It is noteworthy, that immunization of rabbits with native chimeric 16L1-16L2 17-36 VLP, adjuvanted by Alum-MPL induced robust neutralization of high-risk HPV types 16/18/31/45/52/58, low-risk types 6 and 11 and beta HPV type 5, with neutralization titers approximately 10- to 100-fold higher when compared to sera raised against the comparable BL1-16L2 17-36 VLP under identical vaccination conditions (Table 4). These results indicate a favourable presentation of the RG-1 epitope within the aa-composition of HPV16 L1 as carrier. It therefore is expected that cross-neutralization epitopes within the highly conserved region 17-36 of L2 of divergent HPV types can be displayed in an analogous manner.

Chimeric L1-L2 VLP allow for broad-spectrum HPV vaccines. Their potential use is based on L1 VLP as vaccine carrier, which are well tolerated and provide long-term protection of 8 years to date. As the obtained yield is similar to that of HPV16 wt L1 VLP (data not shown), the HPV16 L1-HPV16-L2 17-36 VLP vaccine described herein is expected to provide broad cross-protection to heterotypic HPV types, without increased costs, in addition to high-level and type-restricted protection against homologous HPV 16.

Example III

Further Characterization of the Spectrum of L2-Based Cross-Neutralization

Two NZW rabbits were immunized 4 times at weeks 0, 4, 6, 8 with RG1-VLP (HPV16L1-16L2 (17-36)) plus alum-MPL adjuvant (Charles River, Germany). Antisera were drawn 2 weeks after the 4th immunization and tested using newly established pseudovirion neutralization assays of HPV types 3, 32, 33, 38, 68, 76 (Helena Faust, Joakim Diliner, unpublished). Pre-immune sera of the same rabbits were used as controls. Antiserum of a NZW rabbit that had been immunized with wild-type HPV16L1 VLP plus Freund's adjuvant (first immunization with complete Freund's adjuvant (CFA), boosts with incomplete Freund's adjuvant (IFA)) was used as further control. Sera were diluted 1:100, 1:1000 and 1:10,000 and tested twice. Sera that were non-neutralizing at dilution 1:100 were further tested once at dilution 1:50.

The antisera to RG1-VLP cross-neutralized mucosal high-risk HPV types 33, 68, 76, mucosal type HPV32 (causing Heck's disease), and alpha-skin type HPV3, with titers from 50 to 1,000 (Table 5, columns 2, 4). In contrast, pre-immune sera of the same rabbits were non-neutralizing in all assays (columns 1, 3).

In addition, low-titer neutralization of HPV 32, 33, and 68 was detected for antiserum #4835 to HPV16 wild-type L1 VLP (column 5). Of note, the latter serum had been raised using the strong adjuvant Freund's.

TABLE 5

Pseudovirion neutralization assays.

| | 1 | 2 | 3 | 4 | 5 |
|---|---|---|---|---|---|
| HPV3 | no | 1000 | no | 1000 | no |
| HPV32 | no | 50 | no | 100 | 50 |
| HPV33 | no | 100 | no | 100 | 100 |
| HPV38 | no | no | no | no | no |
| HPV68 | no | 1000 | no | 100 | 50 |
| HPV76 | no | 100 | no | 100 | no |

Titers shown correspond to the highest reciprocal dilution of the indicated (pre-)immune rabbit sera to RG1-VLP, or HPV16 wt L1 VLP, that neutralized indicated HPV pseudovirion types.
1, NZW#1 pre-immunization
2, RG1-VLP + AlumMPL NZW#1 post 4th immunization
3, NZW#2 pre-immunization
4, RG1-VLP + AlumMPL NZW#2 post 4th immunization
5, HPV16 wt L1 VLP + CFA/IFA NZW#4835 post 4th immunization HPV2a Virion Neutralization Assay (RT-PCR)

We next determined the capacity of antisera to RG1-VLP to neutralize alpha skin-type HPV2a, which is closely related to HPV27 and 57. HPV1, 2, 27 and 57 are the most prevalent HPV types detected in 96% of HPV-positive cutaneous common warts (de Koning et al., *J Clin Microbiol*). In addition, a long duration of HPV2-related warts has been described (Rubben et al. (1997) *Arch Dermatol Res* 289, 337-340), and HPV2 and HPV57 have also been isolated from mucosal lesions. To develop an in vitro infectious virion-based neutralization assay, native HPV2a was isolated from a large plantar wart of a patient suffering from multiple extensive skin warts. To determine the HPV type, genomic DNA was isolated from wart tissue and PCR-amplified by 40 cycles using general primers CP4/CP5, or PPF1/CP5, targeting the E1 region:

PPF1
(SEQ ID NO: 86)
5'-(nt2082)-AAC-AAT-GTG-TAG-ACA-TTA-TAA-ACG-AGC-(nt 2108)-3'

CP4
(SEQ ID NO: 87)
5'-(nt1942)-ATG-GTA-CAR-TGG-GCA-TWT-GA-(nt1961)-3'

CP5
(SEQ ID NO: 88)
5'-(nt2400)-GAG-GYT-GCA-ACC-AAA-AMT-GRC-T-(nt2378)-3'

Amplimers were sequenced and nucleotide BLAST (ncbi.nlm.nih.gov) revealed 100% match to HPV2a (Accession number X55964, as of the date of filing the present application).

Wart tissue was removed using a razor blade and, following addition of an equal volume of PBS, frozen in liquid nitrogen. The tissue was thawed and mechanically homogenized using steel beads using Fast Prep-24 Instrument at 4.0 M/S, 2 times 20 sec (MP Biomedicals, LLC). Following a 5 min spin at 14,000 rpm in an Eppendorf microfuge, virion-containing supernatant was harvested and stored in aliquots at −80° C.

The neutralization assay was developed in analogy to a described method (Smith et al. (1995) *J. Invest. Dermatol.* 105, 438-444; Shafti-Keramat et al. (2003) *J Virol* 77, 13125-13135). Briefly, keratinocytes ($3 \times 10^5$ cells) were seeded into 60-mm-diameter tissue culture plates. The next day the culture medium was aspirated and cells were infected with 2 μl of HPV2 virion solution in 1 ml of DMEM (Invitrogen) pre-incubated with the indicated dilution of pre-immune or immune sera to RG1-VLP, or medium only as control, before being added to cells, incubated for 1 hour at room temperature with gentle rocking every 15 min, and then fed with 4 ml of fresh DMEM+10% FCS+1% antibiotic/antimycotic (Invitrogen). As specificity control, virions were incubated with antiserum raised against HPV2 L1-VLP (a kind gift of Tilo Senger, German Cancer Research Center, Heidelberg), or HPV16 wt-L1wt-L2 VLP. After 24 hours of incubation, total cellular RNA was harvested by using Tri Reagent (Molecular Research Center, Cincinnati, Ohio). For first-strand cDNA synthesis, oligop(dT)15 primers were used (Roche). Spliced HPV2 E1^E4 mRNA was detected by two rounds of 30-cycle nested PCR using the following primers: 1st round: HPV2 UO: 5'-GGGTGGTAACTACCTGCTG-3' (SEQ ID NO:89), HPV2 DO: 5'-CTCTTGTCAGGAACTCTGTACG-3' (SEQ ID NO:90); 2nd round: HPV2 UI: 5'-CAGAACCGTCCG-GCTGGTGG-3' (SEQ ID NO:91) HPV2 DI: 5'-CCCAC-CCGCCCAGTGCCAC-3' (SEQ ID NO:92). The expected final sizes of the PCR amplicons were 556 by for spliced HPV2 mRNA and 429 by for spliced beta-actin mRNA.

Figure 5:
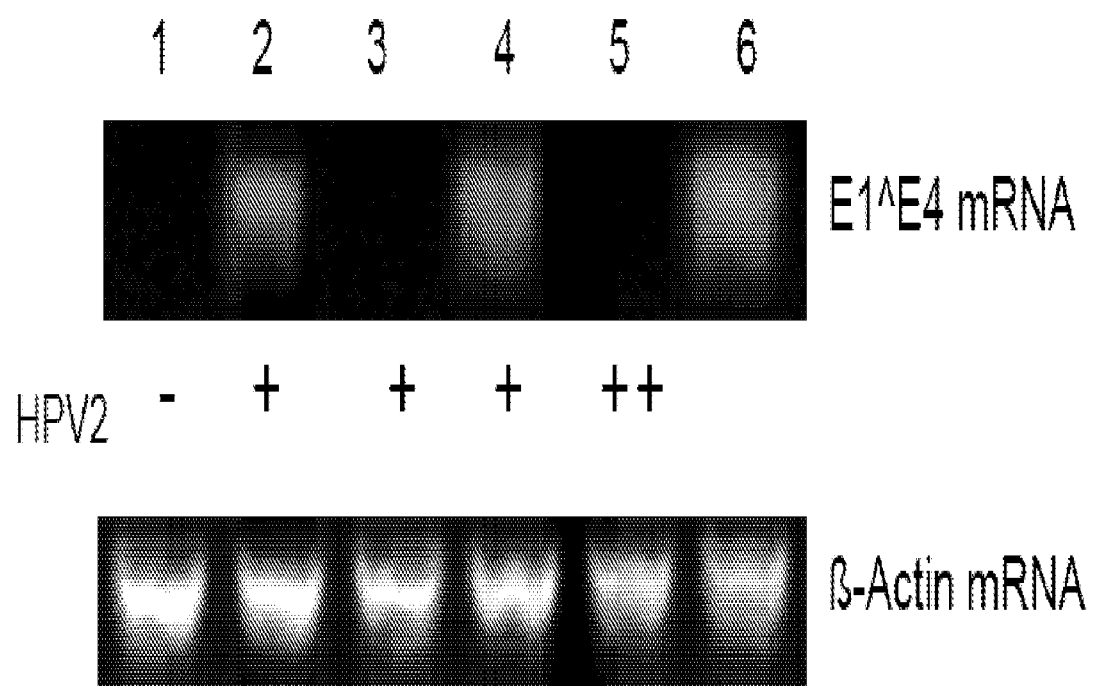
FIG. 5 shows neutralization of native HPV2a virions by antisera to RG1-VLP (HPV16 L1/L2 (17-36)) (RT-PCR Neutralization Assay). HPV2a virions were isolated from a human plantar wart, incubated in the presence or absence of indicated sera at final dilution 1:400, and added to HaCaT cells (lanes 2-6). RNA was reverse transcribed into cDNA and spliced viral RNA was detected by two rounds of nested PCR, and beta-actin RNA was detected by one round of PCR as a control. Lane 1, HaCaT cells only; lane 2, only HPV2, no serum added; lane 3, anti-HPV2 L1-VLP; lane 4, pre-immune anti-RG1-VLP; lane 5, immune anti-RG1-VLP; lane 6, anti-HPV16 wt L1/wt L2-VLP. Sera were tested at final dilution of 1:400.

As shown in FIG. 5, the anti-RG1-antiserum neutralized HPV2a virions as indicated by the absence of detectable viral RNA (lane 5), whereas the no-serum control (lane 2), the pre-immune serum (lane 4), and a serum raised against HPV16 wt-L1/wt-L2 VLP (lane 6) were non-neutralizing. As appropriate controls, no viral RNA was detected when no virus was added to cells (lane 1), or when a neutralizing anti-HPV2 L1 VLP serum was used (lane 3).

To determine neutralization titers over time, two rabbits were immunized with RG1-VLP plus Alum-MPL at 0, 4, 6, 8 weeks and sera analyzed 10 months following the third boost. The titers of (cross-)neutralizing antisera were detectable with a 10 to 100-fold decrease or had became undetectable, when compared to titers of sera drawn two weeks after the third boost (Table 6, compare column '10 months' with column '3nd boost'). Importantly, an additional RG1-VLP plus Alum-MPL boost of rabbits at month 10 increased titers of sera drawn two weeks later to former levels at the minimum (See Table 6, column '4th boost'). These data indicate a functional B-cell memory response to the (cross-)neutralization epitopes of RG1-VLP.

TABLE 6

Booster immunization of two NZW rabbits with RG1-VLP (HPV16L1-16L2 (17-36)) 10 months after primary immunization]

| | neutralizing titer | | | | | |
|---|---|---|---|---|---|---|
| | NZW # 1 | | | NZW # 2 | | |
| Pseudo-virions | 3rd boost | 10 months follow-up | 4th boost | 3rd boost | 10 months follow-up | 4th boost |
| HPV 16 | 100,000 | 1,000 | 100,000 | 100,000 | 1,000 | 100,000 |
| HPV 18 | 1,000 | 50 | 1,000 | 1,000 | 100 | 1,000 |
| HPV 31 | 10,000 | 100 | 1,000 | 1,000 | 100 | 10,000 |
| HPV 45 | 1,000 | 0 | 1,000 | 100 | 100 | 1,000 |
| HPV 52 | 100 | 0 | 1,000 | 50 | 0 | 50 |
| HPV 58 | 1,000 | 0 | 10,000 | 1,000 | 100 | 1,000 |
| HPV 6 | 100 | 0 | 1000 | 50 | 0 | 100 |
| HPV 11 | 100 | ? | ? | 0 | ? | ? |
| HPV 5 | 100 | 0 | 1,000 | 50 | 0 | 100 |

Table 6: Two NZW rabbits were immunized with RG1-VLP plus Alum-MPL as described above, and sera drawn 2 weeks after the fourth immunization (3$^{rd}$ boost). 10 month later, sera were drawn (10 months follow uo) and both rabbits received an additional boost of RG1-VLP plus Alum-MPL adjuvant and sera were drawn again two weeks later (4$^{th}$ boost). Sera were analyzed by end-point 10-fold serial dilutions in indicated pseudovirion neutralization assays. Neutralization titers are shown. The question mark (?) indicates that respective neutralizing titer has not been determined.

Conclusion: Immunization with chimeric HPV16L1-RG1 VLP in adjuvant applicable for human use can induce long-lasting broad-spectrum antibody responses to mucosal high-risk, low-risk and divergent cutaneous alpha and beta papillomaviruses.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications (including provisional patent application 61/168,445, filed Apr. 10, 2009) cited above and in the figures are hereby incorporated in their entirety by reference.

We claim:

1. A capsomere composition, assembled from a chimeric polypeptide comprising a papillomavirus (PV) L1 protein, into the DE loop of which is inserted a surface-displayed peptide consisting of one of the following sequences from a HPV16 L2 protein:
   a) QLYKTCKQAGTCPPDIIPKV (SEQ ID NO:9), or
   b) QLYKTCKQAGTCPPDIIPKVEG (SEQ ID NO: 56), or
   c) LYKTCKQAGTCPPDIIPKVEG (SEQ ID NO:57).

2. A virus-like particle (VLP) composition, assembled from a chimeric polypeptide comprising a papilloma virus (PV) L1 protein into which is inserted into a DE loop of the L1 protein a surface-displayed peptide consisting of the following sequence from a papillomavirus L2 protein, wherein the inserted L2 peptide is from the HPV 16 L2 (17-36) peptide, and has the amino acid sequence QLYKTCKQAGTCPPDIIPKV (SEQ ID NO:9).

3. The VLP of claim 2, wherein the L1 protein is from HPV16, and the L2 peptide is inserted between amino acids 136 and 137 in the DE loop of the L1 protein (SEQ ID NO:85); or the L1 protein is from BPV1, and the L2 peptide is inserted between amino acids 133 and 134 in the DE loop of the L1 protein (SEQ ID NO:83).

4. The VLP composition of claim 2, which is an immunogenic composition.

5. The VLP composition of claim 4, which is immunogenic against mucosal high-risk or low-risk, cutaneous low risk, and/or cutaneous beta-type papillomaviruses.

6. A vaccine, comprising a VLP composition of claim 2 and an adjuvant.

7. The vaccine of claim 6, which is effective against human papillomaviruses.

8. The vaccine of claim 6, wherein the composition is formulated for administration by inhalation, ingestion, or intramuscular injection.

9. A nucleic acid encoding the chimeric polypeptide of claim 2.

10. A method for making a VLP or a capsomere composition, comprising incubating a chimeric polypeptide of claim 2 under suitable conditions for self-assembly.

11. A method for immunizing or vaccinating a subject against a PV, comprising administering to the subject an effective amount of a VLP composition of claim 2.

12. A method for inducing an immune response against HPV in a subject, comprising administering to the subject an effective amount of a VLP composition of claim 2.

13. A method for treating a PV infection in a subject having a PV infection or at risk of being exposed to PV, comprising administering to the subject an effective amount of a VLP composition of claim 2.

14. A method for preventing cervical, anogenital, oropharyngeal cancer, or a precancer, in a subject, comprising administering to the subject an effective amount of a VLP composition of claim 2.

15. A kit comprising a VLP composition of claim 2.

16. A virus-like particle (VLP) composition, assembled from a chimeric polypeptide comprising a papilloma virus (PV) L1 protein into which is inserted into the DE loop of the L1 protein a surface-displayed peptide consisting of the following sequence from a papillomavirus L2 protein, wherein the inserted L2 peptide is from the HPV 16 L2 (17-38) peptide, and has the amino acid sequence QLYKTCKQAGTCPPDIIPKVEG (SEQ ID NO: 56).

17. The VLP of claim 16, wherein the L1 protein is from HPV16, and the L2 peptide is inserted between amino acids 136 and 137 in the DE loop of the L1 protein (SEQ ID NO:85); or the L1 protein is from BPV1, and the L2 peptide is inserted between amino acids 133 and 134 in the DE loop of the L1 protein (SEQ ID NO:83).

18. The VLP composition of claim 16, which is an immunogenic composition.

19. The VLP composition of claim 18, which is immunogenic against mucosal high-risk or low-risk, cutaneous low risk, and/or cutaneous beta-type papillomaviruses.

20. A vaccine, comprising a VLP composition of claim 16 and an adjuvant.

21. The vaccine of claim 20, which is effective against human papillomaviruses.

22. The vaccine of claim 20, wherein the composition is formulated for administration by inhalation, ingestion, or intramuscular injection.

23. A nucleic acid encoding the chimeric polypeptide of claim 16.

24. A method for making a VLP or a capsomere composition, comprising incubating a chimeric polypeptide of claim 16 under suitable conditions for self-assembly.

25. A method for immunizing or vaccinating a subject against a PV, comprising administering to the subject an effective amount of a VLP composition of claim 16.

26. A method for inducing an immune response against HPV in a subject, comprising administering to the subject an effective amount of a VLP composition of claim 16.

27. A method for treating a PV infection in a subject having a PV infection or at risk of being exposed to PV, comprising administering to the subject an effective amount of a VLP composition of claim 16.

28. A method for preventing cervical, anogenital, oropharyngeal cancer, or a precancer, in a subject, comprising administering to the subject an effective amount of a VLP composition of claim 16.

29. A kit comprising a VLP composition of claim 16.

30. A virus-like particle (VLP) composition, assembled from a chimeric polypeptide comprising a papilloma virus (PV) L1 protein into which is inserted into the DE loop of the L1 protein a surface-displayed peptide consisting of the following sequence from a papillomavirus L2 (18-38) peptide, wherein the inserted L2 peptide is from the HPV 16 L2 protein, and has the amino acid sequence LYKTCKQAGTCPPDIIPKVEG (SEQ ID NO:57).

31. The VLP of claim 30, wherein the L1 protein is from HPV16, and the L2 peptide is inserted between amino acids 136 and 137 in the DE loop of the L1 protein (SEQ ID NO:85); or the L1 protein is from BPV1, and the L2 peptide is inserted between amino acids 133 and 134 in the DE loop of the L1 protein (SEQ ID NO:83).

32. The VLP composition of claim 30, which is an immunogenic composition.

33. The VLP composition of claim 32, which is immunogenic against mucosal high-risk or low-risk, cutaneous low risk, and/or cutaneous beta-type papillomaviruses.

34. A vaccine, comprising a VLP composition of claim 30 and an adjuvant.

35. The vaccine of claim 34, which is effective against human papillomaviruses.

36. The vaccine of claim 34, wherein the composition is formulated for administration by inhalation, ingestion, or intramuscular injection.

37. A nucleic acid encoding the chimeric polypeptide of claim 30.

38. A method for making a VLP or a capsomere composition, comprising incubating a chimeric polypeptide of claim 30 under suitable conditions for self-assembly.

39. A method for immunizing or vaccinating a subject against a PV, comprising administering to the subject an effective amount of a VLP composition of claim 30.

40. A method for inducing an immune response against HPV in a subject, comprising administering to the subject an effective amount of a VLP composition of claim 30.

41. A method for treating a PV infection in a subject having a PV infection or at risk of being exposed to PV, comprising administering to the subject an effective amount of a VLP composition of claim 30.

42. A method for preventing cervical, anogenital, oropharyngeal cancer, or a precancer, in a subject, comprising administering to the subject an effective amount of a VLP composition of claim 30.

43. A kit comprising a VLP composition of claim 30.

* * * * *